US007060248B2

(12) United States Patent
Carpenter, Jr. et al.

(10) Patent No.: US 7,060,248 B2
(45) Date of Patent: Jun. 13, 2006

(54) MATRIX METALLOPROTEINASE INHIBITORS

(75) Inventors: Alan P. Carpenter, Jr., Carlisle, MA (US); Milind Rajopadhye, Westford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 375 days.

(21) Appl. No.: 10/645,272

(22) Filed: Aug. 21, 2003

(65) Prior Publication Data

US 2005/0047999 A1 Mar. 3, 2005

Related U.S. Application Data

(63) Continuation of application No. 09/783,249, filed on Feb. 14, 2001, now Pat. No. 6,656,448
(60) Provisional application No. 60/182,712, filed on Feb. 15, 2000.

(51) Int. Cl.
*A61K 49/00* (2006.01)

(52) U.S. Cl. .................... 424/9.1; 424/1.11; 424/1.65
(58) Field of Classification Search ............. 424/1.11, 424/1.65, 1.69, 9.1, 9.2, 9.3, 9.4, 9.5, 9.6, 424/9.7, 9.8, 1.37; 534/7, 10–16; 206/223, 206/569, 570

See application file for complete search history.

(56) References Cited

U.S. PATENT DOCUMENTS

| | | | |
|---|---|---|---|
| 4,859,777 A | 8/1989 | Toner | 546/256 |
| 4,988,827 A | 1/1991 | Bergstein et al. | 549/451 |
| 5,064,956 A | 11/1991 | Kruper, Jr. | 540/474 |
| 5,087,440 A | 2/1992 | Cacheris et al. | 424/9 |
| 5,155,215 A | 10/1992 | Ranney | 534/16 |
| 5,281,704 A | 1/1994 | Love et al. | 540/465 |
| 5,412,148 A | 5/1995 | Keana | 560/35 |
| 5,417,959 A | 5/1995 | Wallace | 424/9.363 |
| 5,520,904 A | 5/1996 | Nosco et al. | 424/9.322 |
| 5,567,411 A | 10/1996 | Keana et al. | 424/9.1 |
| 5,674,754 A | 10/1997 | Ahrens et al. | 436/518 |
| 5,679,810 A | 10/1997 | Love et al. | 556/1 |
| 5,739,789 A | 4/1998 | Kronhamn | 342/465 |
| 5,750,088 A | 5/1998 | Sworin et al. | 424/1.69 |
| 5,760,191 A | 6/1998 | Snow et al. | 534/10 |
| 5,801,228 A | 9/1998 | Hollister et al. | 534/15 |
| 5,804,161 A | 9/1998 | Long et al. | 424/9.42 |
| 5,879,659 A | 3/1999 | Edwards et al. | 424/1.69 |
| 6,057,336 A | 5/2000 | Duan et al. | 514/312 |
| 6,172,057 B1 | 1/2001 | Venkatesan et al. | 514/212.01 |
| 6,254,852 B1 | 7/2001 | Glajch et al. | 424/9.52 |
| 6,268,379 B1 | 7/2001 | Xue et al. | 514/307 |
| 6,365,587 B1 | 4/2002 | Voss et al. | 514/227.5 |
| 6,429,213 B1 | 8/2002 | Xue et al. | 514/312 |
| 6,455,522 B1 | 9/2002 | Duan et al. | 514/221 |
| 6,495,548 B1 | 12/2002 | Duan | 514/231.5 |
| 6,576,664 B1 | 6/2003 | Yao et al. | 514/533 |
| 6,656,448 B1 * | 12/2003 | Carpenter, Jr. et al. | 424/9.1 |

FOREIGN PATENT DOCUMENTS

| | | |
|---|---|---|
| EP | 0 107 734 | 5/1984 |
| EP | 0 727 225 A2 | 8/1996 |
| WO | WO 91/14460 | 10/1991 |
| WO | WO 92/17215 | 10/1992 |
| WO | WO 94/22496 | 10/1994 |
| WO | WO 97/36619 | 10/1997 |
| WO | WO 98/47541 | 10/1998 |
| WO | WO 99/40947 | 8/1999 |
| WO | WO 99/64406 | 12/1999 |

OTHER PUBLICATIONS

Anthony, et al., *Gastroenterology*, 1992, Abstract 591.
Armstrong, P.W., et al., *Can. J. Cardiol.*, 1994, 10, 214–220.
Beckett, et al., *Research Focus*, 1996, 1, 16–26.
Beckett, et al., *Curr. Opin. Ther. Patents*, 1994, 4(1), 7–16.
Bond, B.R., et al., *Circulation*, 1999, 100(Suppl.), 1–12.
Brown, et al., *Circulation*, 1995, 91, 2125–2131.
Coker, et al., *Am. J. Physiol.*, 1998, 274, H1516–H1523.
Davidsen, et al., *Exp. Opin. Ther. Patents*, 1995, 5(2), 1087–1100.
Davies, M.J., *Circulation*, 1996, 94, 2013–2020.
Dollery, et al., *Circ. Res.*, 1995, 77, 863–868.
Falk, et al., *Circulation*, 1994, 90, 775–778
Falk, et al., *Circulation*,1995, 92, 657–671.
Galis, et al., *J. Clim. Invest.*, 1994, 94, 2493–2503.
Garbisa, et al., *Cancer Res.*, 1992, 52, 4548.
Henney, et al., *Proc. Natl. Sci.*, 1991, 88, 8154–8158.
Libby, P., *Circulation*, 1995, 91, 2844–2850.
Lu, et al., *Circulation*, 1999, 100 (Suppl. 1), 1–12.
Matthes, et al., *Gastroenterology*, 1992, Abstract 661.
Murphy, et al., *Curr. Medicinal Chem.*, 1995, 2, 743–762.
Porter, et al., *Exp. Opinion Ther. Patents*, 1995, 5(12), 1287–1196.
Rohde, et al., *JACC*, 1999, 33, 835–842.
Walakovits, et al., *Arth. Rheum.*, 1992, 35, 35.
Whittaker, et al., *Chem. Rev.*, 1999, 99, 2735–2776.
Zucker, et al., *Cancer Res.*, 1993, 53, 140.

(Continued)

*Primary Examiner*—Dameron Jones
(74) *Attorney, Agent, or Firm*—Woodcock Washburn LLP

(57) ABSTRACT

Thus the present invention describes diagnostic agents comprising a diagnostic metal and a compound, wherein the compound comprises: 1–10 targeting moieties; a chelator; and 0–1 linking groups between the targeting moiety and chelator; wherein the targeting moiety is a matrix metalloproteinase inhibitor; and wherein the chelator is capable of conjugating to the diagnostic metal. The present invention also provides novel compositions of the compounds of the invention, kits, and their uses in diagnosis of diseases associated with MMPs.

53 Claims, No Drawings

OTHER PUBLICATIONS

Andrews D.R., et al., "Reaction of aziridinium iions with organometallic reagents: optimization of the key step step of ecopipam synthesis," *Tetrahedron Letts.*, 2002, 43, 6121–6124.

Antunes, M.L., et al., "Diagnosis of right ventricular acute myocardial infarction by dual isotope thallium–201 and indium–111 antimyosin SPECT imaging," *Am. J. Cardiol.*, August 15, 1992, 70, 426–431.

Babine, R.E., et al., "Molecular recognition of protein— ligand complexes: applications to drug design,"*Chem. Rev.*, 1997, 97, 1359–1472.

Beckett, R.P., et al., "Recent advances in matrix metalliproteinase inhibitor research," *Drug Discovery Today*, Jan. 1996, 1(1), 16–26.

Bousquet, J.—C., "Gd–DOTA: characterization of a new paramagnetic complex," *Radiology*, 1988, 166, 693–698.

Brechbiel, M.W., et al., "Synthesis of C–functionalized *trans*–cyclohexyldiethylenetriaminepenta–acetic acids for labeling of monoclonal antibodies with the bismuth–212 α–particle emitter," *J.Chem. Soc. Perkin Trans.*, 1992, 1, 1173–1178.

Brechbiel, M.W., et al., "Backbone–substituted DTPA ligands for $^{90}$Y radioimmunotherapy," *Bioconjugate Chem.*, 1991, 2(3), 187–194.

Brinkley, M., "A brief survey of methods for preparing protein conjugates with dyes haptens, and cross–linking reagents," *Bioconjugate Chem.*, 1992, 3, 2–13.

Cheung, S.T., et al., "N–methylamino acids in peptide sunthesis. VI. A method for determining the enantiomeric purity of N–methylamino acids and their derivatives by ion–exchange chromatography as their C–terminal lysyl dipeptied," *Can. J. Chem.*, 1977, 55, 911–915.

Davidsen, S.K., et al., "Pulmonary–allergy, dermatological, gastrointestinal & arthritis; inhibitors of TNFα synthesis" *Exp. Opin. Ther. Patents*, 1995, 5(10), 1087–1110.

De, B., et al., "The next generation of MMP inhibitors," *Ann. N.Y. Acad. Sci.*, 1999, 878, 40–60.

DeGrado, W.F., et al., "Polymer–bound oxime esters as supports for solid–phase peptide synthesis. Preparation of protected peptide fragments," *Am. Chem. Soc.*, 1980, 45, 1295–1300.

Deshpande, S.V., et al., "Yttrium–90–labeled monoclonal antibody for therapy: labeling by a new macrocyclic bifunctional chelating agent," *J. Nucl. Med.*, 1990, 31, 473–479.

Hubbuch, A., et al., "Synthesis of N–protected cysteic acid derivatives and their activated esters," *Liebigs Ann. Chem.*, 1979, 776–783 (English Abstract included).

Johnson, W.H., et al., "Collagenase inhibitors: their design and potential therapeutic use," J. Enz. Inhib., 1987, 2, 1–22.

Levin, J.I., et al., "The asymmetric synthesis and *in vitro*-characterization of succinyl mercaptoalcohol and mercaptoketone inhibitors of matrix metalloproteinases," *Bioorg. & Med. Chem. Lett.*, 1998, 8, 1163–1168.

Lovejoy, B., et al., "Crystal structures of MMP–1 and –13 reveal the structural basis for selectivity of collagenase inhibitors," *Nature Struct. Biol.*, Mar. 1999, 6(3), 217–221.

MacPherson, L.J., et al., "Discovery of CGS 27023A, a non–peptidic, potent, and orally active stromelysin inhibitor that blocks cartilage in rabbits," *J. Med.Chem.*, 1997, 40, 2525–2532.

Margerstadt, M., et al., "Gd(DOTA): an alternative to Gd(DTPA) as a $T_{1,2}$ relaxation agent for NMR imaging or spectroscopy," *Magn. Reson. in Med.*, 1986, 3, 808–812.

Merrifield, R.B., "Solid phase peptide sysnthesis. I. The synthesis of a tetrapeptide," *J. Am. Chem. Soc.*, 1963, 85, 2149–2154.

Miller, A., et al., "Inhibition of matrix metalloproteinases: an examination of the S1'pocket," *Bioorg. & Med. Chem. Lett.*, 1997, 7(2), 193–198.

Morphy, J.R., et al., "Matrix metalloproteinase inhibitors: current status," *Curr. Medicinal Chem.*, 1995, 2, 743–762.

Porter, J.R., "Oncologic, Ondocrine & Metabolic; recent developments in matrix metalloproteinase inhibitors," *Exp. Opin. Ther. Patents*, 1995, 5(12), 1287–1296.

Roberts, D.C., et al., "Unusual amino acids in peptide synthesis," *The Peptides, Academic Press*, New York, 1983, vol. 5, Chapter 6, 342–449.

Remington's Pharmaceutical Science, 17$^{th}$ Ed., 1985, *Mack Publishing Co.*, Easton, PA, p. 1418.

Runge, V.M., et al., "MR imaging of rat brain glioma: Gd–DTPA versus Gd–DOTA$^1$," *Radiology*, 1988, 166, 835–838.

Sahoo, S.P., et al., "Inhibition of martrix metalloptoyrinses by N–carboxyalkyl dipeptides: enhanced potency and selectivity with substituded $P_1$' homophenylalanines," *Bioorg. & Med. Chem. Lett.*, 1995, 5(20), 2441–2446.

Santos, O., et al., "Rodent pharomacokinetic and anti–tumor effiacy studies with a series of synthethic inhibitors of matrix metalloproteinases," *Clin. Exp. Metastasis* 1997, 15, 499–508.

Sheppard, G.S., et al., "Aryl ketones as novel replacements for the C–terminal amide bond of succinyl hydroxamate MMP inhibitors," *Bioorg. & Med. Chem. Lett.*, 1998, 8, 3251–3256.

Steinman, D.H., et al., "The design, synthesis, and structure–activity relationships of a series of macrocyclic MMP inhibitors," *Bioorg. & Med. Chem. Lett.*, 1998, 8, 2087–2092.

Summers, J.B., et al., "Matrix metalloproteinase inhibitors and cancer," *Annual Reports in Med. Chem.*, 1998, 33, 131–140.

Xue, C–B., et al., "Design and synthesis of cyclic inhibitors of matrix metalloproteinases and TNF–α production," *J. Med. Chem.*, 1998, 41, 1745–1748.

\* cited by examiner

MATRIX METALLOPROTEINASE INHIBITORS

CROSS REFERENCE TO RELATED APPLICATIONS

This a application is a continuation of U.S. application Ser. No. 09/783,249 filed Feb. 14, 2001 now U.S. Pat. No. 6,656,448, which claims the benefit to provisional application No. 60/182,712, filed Feb. 15, 2000.

FIELD OF THE INVENTION

The present invention provides novel compounds useful for the diagnosis of cardiovascular pathologies associated with extracellular matrix degradation, such as atherosclerosis, heart failure, and restenosis, methods of imaging these pathologies in a patient, and pharmaceutical compositions comprising the compounds. The pharmaceuticals are comprised of a targeting moiety that inhibits a matrix metalloproteinase that is expressed in these pathologies, an optional linking group, and a diagnostically effective imageable moiety. The imageable moiety is a gamma ray or positron emitting radioisotope, a magnetic resonance imaging contrast agent, an X-ray contrast agent, or an ultrasound contrast agent.

BACKGROUND OF THE INVENTION

The ability to detect increased levels of matrix metalloproteinases (MMPs) in the heart would be extremely useful for the detection of tissue degradation which occurs in many heart conditions. The composition and vulnerability of atheromatous plaque in the coronary arteries has recently been recognized as a key determinant in thrombus-mediated acute coronary events, such as unstable angina, myocardial infarction and death (Falk E, Shah P K and Fuster V; Circulation 1995; 92: 657–671). Among the many components involved in the inflammatory atheromatous plaque are macrophages which secrete the matrix metalloproteinases (Davies M J; Circulation 1996; 94: 2013–2020). The MMPs are a family of enzymes which specialize in the cleavage of the usually protease-resistant fibrillar extracellular matrix components of the heart, such as collagen. These extracellular matrix proteins confer strength to the fibrous cap of atheroma (Libby P, Circulation 1995; 91: 2844–2850).

Macrophages which accumulate in areas of inflammation such as atherosclerotic plaques release these MMPs which degrade connective tissue matrix proteins (Falk, 1995). In fact, studies have demonstrated that both the metalloproteinases and their mRNA are present in atherosclerotic plaques (Coker M L, Thomas C V, Clair M J, et al.; Am. J. Physiol. 1998; 274:H1516–1523; Dollery C M, McEwan J R, Henney A., et al.; Circ. Res. 1995; 77:863–868; Henney A., Wakeley P., Davies M., et al.; Proc Natl Acad Sci 1991; 88:8154–8158), particularly in the vulnerable regions of human atherosclerotic plaques (Galis Z, Sukhova G, Lark M. and Libby P.; J Clin Invest. 1994; 94: 2493–2503). Amongst the metalloproteinases that may be released by macrophages present at the site of human atheroma are interstitial collagenase (MMP-1), gelatinases A and B (MMP-2 and MMP-9, respectively) and stromelysin (MMP-3 Moreno P R, Falk E., Palacious I F et al.; Circulation 1994; 90: 775–778). Although all MMPs may be elevated at the site of human atheroma, it has been suggested that gelatinase B may be one of the most prevalent MMPs in the plaque because it can be expressed by virtually all activated macrophages (Brown D., Hibbs M, Kerney M., et al.; Circulation 1995; 91: 2125–2131). The MMP-9 has also been shown to be more prevalent in atherectomy material from unstable angina relative to stable angina patients (Brown, 1995).

The left ventricular extracellular matrix, containing a variety of collagens and elastin, are also proposed to participate in the maintenance of left ventricle (LV) geometry. Therefore, alterations in these extracellular components of the myocardium may influence LV function and be a marker of progressive changes associated with LV degeneration and ultimately heart failure (Coker, 1998).

In the situation of congestive heart failure (CHF), the relationship of CHF state to MMP activity in the LV remains somewhat unclear, at least in the clinical setting. In preclinical models of CHF, however, the functional changes in the LV have been correlated with increased MMP activity. For example, in a pig model of CHF, the decrease in LV function was observed to coincide with a marked increase in MMP-1 (~300%), MMP-2 (~200%), and MMP-3 (500%) (Coker, 1998). Moderate ischemia and reperfusion in a pig model has been demonstrated to selectively activate MMP-9 (Lu L, et al., Circulation, 1999, 100 Suppl. 1, I-12). Similarly in a dog model of CHF the levels of gelatinases (e.g. MMP-2 and MMP-9) were found to be elevated in severe heart failure (Armstrong P W, Moe G W, et al., Can J Cardiol 1994; 10: 214–220). The levels of MMP-2 and MT1-MMP (membrane type MMP, MMP-14) were found to be increased in biopsy samples of human myocytes from patients suffering from dilated cardiomyopathy (Bond B R, et al., Circulation, 1999, 100 Suppl. 1, I-12).

Ahrens, et al. U.S. Pat. No. 5,674,754 discloses methods for the detection of Matrix Metallo-Proteinase No. 9, using antibodies which selectively recognize pro-MMP-9 and complexes of pro-MMP-9 with tissue inhibitor of matrix metallo proteinase-1 (TIMP-1), with no substantial binding to active MMP-9. Venkatesan, et al. U.S. Pat. No. 6,172,057 discloses non-peptide inhibitors of matrix metalloproteinases (MMPs) and TNF-.alpha. converting enzyme (TACE) for the treatment of arthritis, tumor metastasis, tissue ulceration, abnormal wound healing, periodontal disease, bone disease, diabetes (insulinresistance) and HIV infection.

Pathologically, MMPs have been identified as associated with several disease states. For example, anomalous MMP-2 levels have been detected in lung cancer patients, where it was observed that serum MMP-2 levels were significantly elevated in stage IV disease and in those patients with distant metastases as compared to normal sera values (Garbisa et al., 1992, Cancer Res., 53: 4548, incorporated herein by reference.). Also, it was observed that plasma levels of MMP-9 were elevated in patients with colon and breast cancer (Zucker et al., 1993, Cancer Res. 53: 140 incorporated herein by reference).

Elevated levels of stromelysin (MMP-3) and interstitial collagenase (MMP-1) have been noted in synovial fluid derived from rheumatoid arthritis patients as compared to post-traumatic knee injury (Walakovits et al., 1992, Arth. Rheum., 35: 35) incorporated herein by reference. Increased levels of mRNA expression for collagenase type I (MMP-1) and collagenase type IV (MMP-2) have been shown to be increased in ulcerative colitis as compared to Crohn's disease and controls (Matthes et al., 1992, Gastroenterology, Abstract 661, incorporated herein by reference). Furthrmore, Anthony et al., 1992, Gastroenterology, Abstract 591, demonstrated increased immuno-histochemical expression of the gelatinase antigen in arabbit model of chronic inflammatory colitis.

It has been shown that the gelatinase MMPs are most intimately involved with the growth and spread of tumors. It is known that the level of expression of gelatinase is elevated in malignancies, and that gelatinase can degrade the basement membrane which leads to tumor metastasis. Angiogenesis, required for thegrowth of solid tumors, has also recently been shown to have a gelatinase component to its pathology. Furthermore, there is evidence to suggest that gelatinase is involved in plaque rupture associated with atherosclerosis. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing,bone disease, proteinuria, aneurysmal aortic disease, degenerative cartilage loss following traumatic joint injury, demyelinating diseases of the nervous system,cirrhosis of the liver, glomerular disease of the kidney, premature rupture of fetal membranes, inflammatory bowel disease, periodontal disease, age relatedmacular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection. For recent reviews, see: (1) Recent Advances in Matrix Metalloproteinase Inhibitor Research, R. P. Beckett, A. H. Davidson, A. H. Drummond, P. Huxley and M. Whittaker, Research Focus, Vol. 1, 16–26,(1996), (2) Curr. Opin. Ther. Patents (1994) 4(1): 7–16, (3) Curr. Medicinal Chem. (1995) 2: 743–762, (4) Exp. Opin. Ther. Patents (1995) 5(2): 1087–110, (5) Exp. Opin. Ther. Patents (1995) 5(12): 1287–1196, all of which are incorporated herein by reference.

Therefore, the present imaging agents targeted to one or more MMP's would be very useful for detecting and monitoring the degree of extracellular matrix degradation in CHF, atherosclerosis and other degradative disease processes. These imaging agents, containing a ligand directed at one or more MMP's (e.g. MMP-1, MMP-2, MMP-3, MMP-9), will localize a diagnostic imaging probe to the site of pathology for the purpose of non-invasive imaging of these diseases. The imaging agent may be a MMP inhibitor linked to radioisotopes which are known to be useful for imaging by gamma scintigraphy or positron emission tomography (PET). Alternatively, the MMP targeting ligand could be bound to a single or multiple chelator moieties for attachment of one or more paramagnetic metal atoms, which would cause a local change in magnetic properties, such as relaxivity or susceptibility, at the site of tissue damage, which could then be imaged with magnetic resonance imaging systems. Alternatively, the MMP inhibitor can be bound to a phospholipid or polymer material which would be used to encapsulate/stabilize microspheres of gas which would be detectable by ultrasound imaging following localization at the site of tissue injury.

Therefore, imaging agents based on MMP inhibitors would be extremely useful in the detection, staging and monitoring of cardiovascular diseases such as atherosclerosis (especially unstable arterial plaque) and various cardiomyopathies including congestive heart failure. Compounds of the present invention, which localize in areas of MMP activity in the heart, will allow detection and localization of these cardiac diseases which are associated with altered MMP levels relative to normal myocardial tissue.

These imaging agents, whether for gamma scintigraphy, positron emission tomography, MRI, ultrasound or x-ray image enhancement, have utility to detect and monitor changes in cardiovascular diseases over time. Since the degree of overexpression of MMPs is related to the degradation of cardiac or vascular tissue (Rohde L E, Aikawa M, Cheng G C, et al., JACC 1999; 33: 835–842) it is possible to assess the severity and current activity of cardiovascular disease lesions (i.e. plaques) by quantitating the degree of localization of these imaging agents at the diseased sites of interest. Moreover, with these imaging agents it is possible to monitor changes in MMP activity associated with the institution of pharmaceutical therapies which slow the progression or cause a reversal of atheroschlerotic changes in the vascular system or a reversal of myocardial degradation associated with congestive heart failure.

Therefore, it can be appreciated that the imaging of MMPs in the heart would be generally useful for the detection, localization and monitoring the progression/regression of a variety of cardiac diseases which are associated with alterations in the MMP content of cardiac tissues.

SUMMARY OF THE INVENTION

It is one object of the present invention to provide imaging agents for cardiovascular pathologies associated with extracellular matrix degradation, such as atherosclerosis, heart failure, and restenosis, comprised of matrix metalloproteinase inhibiting compounds conjugated to an imageable moiety, such as a gamma ray or positron emitting radioisotope, a magnetic resonance imaging contrast agent, an X-ray contrast agent, or an ultrasound contrast agent.

Another aspect of the present invention are diagnostic kits for the preparation of radiopharmaceuticals useful as imaging agents for cardiovascular pathologies associated with extracellular matrix degradation, such as atherosclerosis, heart failure, and restenosis. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention contemplates a method of imaging cardiovascular pathologies associated with extracellular matrix degradation, such as atherosclerosis, heart failure, and restenosis in a patient involving: (1) synthesizing a diagnostic radiopharmaceutical of the present invention, using a reagent of the present invention, capable of localizing at the loci of the cardiovascular pathology; (2) administering said radiopharmaceutical to a patient by injection or infusion; (3) imaging the patient using planar or SPECT gamma scintigraphy, or positron emission tomography.

Another aspect of the present invention contemplates a method of imaging cardiovascular pathologies associated with extracellular matrix degradation, such as atherosclerosis, heart failure, and restenosis in a patient involving: (1) administering a paramagnetic metallopharmaceutical of the present invention capable of localizing the loci of the cardiovascular pathology to a patient by injection or infusion; and (2) imaging the patient using magnetic resonance imaging.

Another aspect of the present invention contemplates a method of imaging cardiovascular pathologies associated with extracellular matrix degradation, such as atherosclerosis, heart failure, and restenosis in a patient involving: (1) administering a X-ray contrast agent of the present invention capable of localizing in tumors to a patient by injection or infusion; and (2) imaging the patient using X-ray computed tomography.

Another aspect of the present invention contemplates a method of imaging cardiovascular pathologies associated with extracellular matrix degradation, such as atherosclerosis, heart failure, and restenosis in a patient involving: (1) administering a ultrasound contrast agent of the present invention capable of localizing in tumors to a patient by injection or infusion; and (2) imaging the patient using sonography.

DETAILED DESCRIPTION

Thus the present invention includes the following embodiments:

(1) A diagnostic agent comprising a diagnostic metal and a compound, wherein the compound comprises:
i) 1–10 targeting moieties;
ii) a chelator; and
iii) 0–1 linking groups between the targeting moiety and chelator;
wherein the targeting moiety is a matrix metalloproteinase inhibitor; and
wherein the chelator is capable of conjugating to the diagnostic metal.

(2) A diagnostic agent according to embodiment 1, wherein the targeting moiety is a matrix metalloproteinase inhibitor having an inhibitory constant $K_i$ of <1000 nM.

(3) A diagnostic agent according to any of embodiments 1–2, wherein the targeting moiety is a matrix metalloproteinase inhibitor having an inhibitory constant $K_i$ of <100 nM.

(4) A diagnostic agent according to any of embodiments 1–3, comprising 1–5 targeting moieties.

(5). A diagnostic agent according to any of embodiments 1–4, comprising one targeting moiety.

(6) A diagnostic agent any of embodiments 1–5, wherein the targeting moiety is an inhibitor of one or more matrix metalloproteinases selected from the group consisting of MMP-1, MMP-2, MMP-3, MMP-9, and MMP-14.

(7) A diagnostic agent of any one of embodiments 1–6, wherein the targeting moiety is an inhibitor of one or more matrix metalloproteinases selected from the group consisting of MMP-2, MMP-9, and MMP-14.

(8) A diagnostic agent according to any one of embodiments 1–7 wherein the targeting moiety is a matrix metalloproteinase inhibitor of the formulae (Ia) or (Ib):

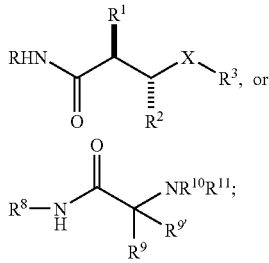

wherein,
R is independently OH or —$CH_2SH$;
$R^1$ is independently selected at each occurrence from the group: H, OH, $C_{1-3}$ alkyl, $C_{2-3}$ alkenyl, $C_{2-3}$ alkynyl, and heterocycle-S—$CH_2$—;

$R^2$ is independently $C_{1-20}$ alkyl;
X is independently C=O or $SO_2$, provided when X is C=O, $R^3$ is

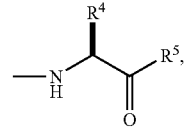

and when X is $SO_2$, $R^3$ is independently selected from the group: aryl substituted with 0–2 $R^6$, and heterocycle substituted with 0–2 $R^6$;
$R^4$ is independently selected at each occurrence from the group: $C_{1-6}$ alkyl, phenyl, and benzyl;
$R^5$ is independently at each occurrence from the group: NH($C_{1-6}$ alkyl), NH-phenyl, and NH-heterocycle; wherein said alkyl, phenyl and heterocycle groups are optionally substituted with a bond to the linking group or a bond to the chelator;
$R^6$ is independently aryloxy substituted with 0–3 $R^7$;
$R^7$ is independently halogen or methoxy;
or alternatively,
$R^1$ and $R^4$ may be taken together to form a bridging group of the formula —$(CH_2)_3$—O-phenyl-$CH_2$—, optionally substituted with a bond to the linking group or a bond to the chelator;
or alternatively,
$R^1$ and $R^2$ may be taken together to form a bridging group of the formula —$(CH_2)_3$—NH—, optionally substituted with a bond to the linking group or a bond to the chelator; or
$R^1$ and $R^2$ taken together with the nitrogen and carbon atom through which they are attached form a $C_{5-7}$ atom saturated ring system substituted with one or more substituents selected from the group consisting of: a bond to Ln, a bond to Ch, and —C(=O)—$NR^{29}R^{30}$;
$R^8$ is independently at each occurrence OH or phenyl, optionally substituted with a bond to the linking group or a bond to the chelator, provided that when $R^8$ is phenyl, $R^{10}$ is —C(=O)—$CR^{12}$—NH—CH($CH_3$)—COOH;
$R^9$ and $R^{9'}$ are independently H, $C_{1-6}$ alkyl optionally substituted with a bond to the linking group or a bond to the chelator, or are taken together with the carbon atom to which $R^9$ and $R^{9'}$ are attached to form a 5–7 atom saturated, partially unsaturated or aromatic ring system containing 0–3 heteroatoms selected from O, N, $SO_2$ and S, said ring system substituted with $R^6$ and optionally substituted with a bond to the linking group or a bond to the chelator;
$R^{10}$ and $R^{11}$ are independently H, or $C_{1-6}$ alkyl optionally substituted with a bond to the linking group or a bond to the chelator, or are taken together with the nitrogen atom to which they are attached to form a 5–7 atom saturated, partially unsaturated or aromatic ring system containing 0–3 heteroatoms selected from O, N, $SO_2$ and S, said ring system optionally substituted with 0–3 $R^{27}$, a bond to the linking group or a bond to the chelator;
or alternatively,
$R^9$ and $R^{10}$ are taken together with the carbon atom to which they are attached to form a 5–7 atom saturated, partially unsaturated or aromatic ring system containing 0–3 heteroatoms selected from O, N, $SO_2$ and S, said ring system optionally substituted with a bond to the linking group or a bond to the chelator; and
$R^{12}$ is independently $C_{1-20}$ alkyl;
$R^{27}$ is =O, $C_{1-4}$ alkyl, or phenyl substituted with $R^{28}$;

$R^{28}$ is a phenoxy group substituted with 0–2 OCH$_3$ groups;
$R^{29}$ and $R^{30}$ taken together with the nitrogen atom through which they are attached form a C5–7 atom saturated ring system substituted with $R^{31}$; and
$R^{31}$ is a benzyloxy group substituted with C1–4 alkyl.

(9). A diagnostic agent according to any one of embodiments 1–8 wherein the targeting moiety is a matrix metalloproteinase inhibitor of the formulae (Ia) or (Ib):

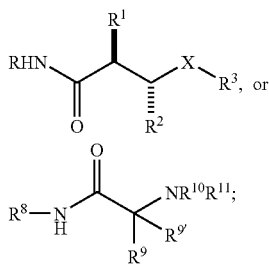

wherein,
R is OH;
$R^1$ is independently selected at each occurrence from the group: H, OH, C$_{1-3}$ alkyl, C$_{2-3}$ alkenyl, C$_{2-3}$ alkynyl, and heterocycle-S—CH$_2$—;
$R^2$ is independently C$_{1-6}$ alkyl;
X is C=O;
$R^4$ is independently selected at each occurrence from the group: C$_{1-6}$ alkyl, phenyl, and benzyl;
$R^5$ is independently at each occurrence from the group: NH(C$_{1-6}$ alkyl), NH-phenyl, and NH-heterocycle; wherein said alkyl, phenyl and heterocycle groups are optionally substituted with a bond to the linking group or a bond to the chelator;
$R^6$ is independently aryloxy substituted with 0–3 $R^7$;
$R^7$ is independently halogen or methoxy;
or alternatively,
$R^1$ and $R^4$ may be taken together to form a bridging group of the formula —(CH$_2$)$_3$—O-phenyl-CH$_2$—, optionally substituted with a bond to the linking group or a bond to the chelator;
or alternatively,
$R^1$ and $R^2$ may be taken together to form a bridging group of the formula —(CH$_2$)$_3$—NH—, optionally substituted with a bond to the linking group or a bond to the chelator; or
$R^1$ and $R^2$ taken together with the nitrogen and carbon atom through which they are attached form a C$_{5-7}$ atom saturated ring system substituted with one or more substituents selected from the group consisting of: a bond to Ln, a bond to Ch, and —C(=O)—NR$^{29}$R$^{30}$;
$R^8$ is OH;
$R^9$ and $R^{9'}$ are independently H, C$_{1-6}$ alkyl optionally substituted with a bond to the linking group or a bond to the chelator, or are taken together with the carbon atom to which $R^9$ and $R^{9'}$ are attached to form a 5–7 atom saturated, partially unsaturated or aromatic ring system containing 0–1 heteroatoms selected from O, N, said ring system optionally substituted with a bond to the linking group or a bond to the chelator;
$R^{10}$ and $R^{11}$ are independently H, or C$_{1-6}$ alkyl optionally substituted with a bond to the linking group or a bond to the chelator, or are taken together with the nitrogen atom to which they are attached to form a 5–7 atom saturated, partially unsaturated or aromatic ring system containing 0–1 heteroatoms selected from O, N, said ring system optionally substituted with 0–3 $R^{27}$, a bond to the linking group or a bond to the chelator;

or alternatively,
$R^9$ and $R^{10}$ are taken together with the carbon atom to which they are attached to form a 5–7 atom saturated, partially unsaturated or aromatic ring system containing, 0–1 heteroatoms selected from O, N, said ring system optionally substituted with a bond to the linking group or a bond to the chelator; and
$R^{12}$ is independently C$_{1-6}$ alkyl;
$R^{27}$ is =O, C1–4 alkyl, or phenyl substituted with $R^{28}$;
$R^{28}$ is a phenoxy group substituted with 0–2 OCH$_3$ groups;
$R^{29}$ and $R^{30}$ taken together with the nitrogen atom through which they are attached form a C5–7 atom saturated ring system substituted with $R^{31}$; and
$R^{31}$ is a benzyloxy group substituted with C1–4 alkyl.

(10). A diagnostic agent according to any one of embodiments 1–9 wherein the targeting moiety is a matrix metalloproteinase inhibitor of the formulae (Ia) or (Ib):
wherein:
R is —OH;
$R^2$ is C$_{1-6}$ alkyl;
X is C=O;
$R^3$ is

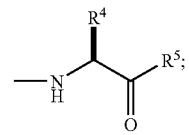

$R^1$ and $R^4$ are taken together to form a bridging group of formula —(CH$_2$)$_3$—O-phenyl-CH$_2$—;
$R^5$ is NH(C1–6alkyl), substituted with a bond to the linking group or a bond to the chelator.

(11) A diagnostic agent according to any one of embodiments 1–10, wherein:
R is —OH;
$R^9$ is C$_1$ alkyl substituted with a bond to Ln;
$R^{10}$ and $R^{11}$ taken together with the nitrogen atom to which they are attached form a 5 atom saturated ring system, said right system is substituted with 0–3 $R^{27}$;
$R^{27}$ is =O, C1–4 alkyl, or phenyl substituted with $R^{28}$; and
$R^{28}$ is a phenoxy group substituted with 0–2 OCH$_3$ groups.

(12) A diagnostic agent according to any one of embodiments 1–11 wherein the
R is —OH;
$R^1$ and $R^2$ taken together with the nitrogen and carbon atom through which they are attached form a C$_{5-7}$ atom saturated ring system substituted with one or more substituents selected from the group consisting of: a bond to Ln, a bond to Ch, and —C(=O)—NR$^{29}$R$^{30}$;
$R^{29}$ and $R^{30}$ taken together with the nitrogen atom through which they are attached form a C5–7 atom saturated ring system substituted with $R^{31}$; and
$R^{31}$ is a benzyloxy group substituted with C1–4 alkyl.

(13) A diagnostic agent according to any one of embodiments 1–12 wherein the linking group is of the formula:

$$((W^1)_h-(CR^{13}R^{14})_g)_x-(Z)_k-((CR^{13a}R^{14a})_{g'}-(W^2)_{h'})_{x'};$$

$W^1$ and $W^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$)$_{s''}$, (CH$_2$CH$_2$CH$_2$O)$_t$, and (aa)$_{t'}$;
aa is independently at each occurrence an amino acid;
Z is selected from the group: aryl substituted with 0–3 $R^{16}$, C$_{3-10}$ cycloalkyl substituted with 0–3 $R^{16}$, and a 5–10 membered heterocyclic ring system containing 1–4 heteroatoms independently selected from N, S, and O and substituted with 0–3 $R^{16}$;

$R^{13}$, $R^{13a}$, $R^{14}$, $R^{14a}$, and $R^{15}$ are independently selected at each occurrence from the group: H, =O, COOH, $SO_3H$, $PO_3H$, $C_1$–$C_5$ alkyl substituted with 0–3 $R^{16}$, aryl substituted with 0–3 $R^{16}$, benzyl substituted with 0–3 $R^{16}$, and $C_1$–$C_5$ alkoxy substituted with 0–3 $R^{16}$, NHC(=O)$R^{17}$, C(=O)NHR$^{17}$, NHC(=O)NHR$^{17}$, NHR$^{17}$, $R^{17}$, and a bond to the chelator;

$R^{16}$ is independently selected at each occurrence from the group: a bond to the chelator, COOR$^{17}$, C(=O)NHR$^{17}$, NHC(=O)R$^{17}$, OH, NHR$^{17}$, $SO_3H$, $PO_3H$, —OPO$_3H_2$, —OSO$_3H$, aryl substituted with 0–3 $R^{17}$, $C_{1-5}$ alkyl substituted with 0–1 $R^{18}$, $C_{1-5}$ alkoxy substituted with 0–1 $R^{18}$ and a 5–10 membered heterocyclic ring system containing 1–4 heteroatoms independently selected from N, S, and O and substituted with 0–3 $R^{17}$;

$R^{17}$ is independently selected at each occurrence from the group: H, alkyl substituted with 0–1 $R^{18}$, aryl substituted with 0–1 $R^{18}$; a 5–10 membered heterocyclic ring system containing 1–4 heteroatoms independently selected from N, S, and O and substituted with 0–1 $R^{18}$, $C_{3-10}$ cycloalkyl substituted with 0–1 $R^{18}$, polyalkylene glycol substituted with 0–1 $R^{18}$, carbohydrate substituted with 0–1 $R^{18}$, cyclodextrin substituted with 0–1 $R^{18}$, amino acid substituted with 0–1 $R^{18}$, polycarboxyalkyl substituted with 0–1 $R^{18}$, polyazaalkyl substituted with 0–1 $R^{18}$, peptide substituted with 0–1 $R^{18}$, wherein the peptide is comprised of 2–10 amino acids, 3,6-O-disulfo-B-D-galactopyranosyl, bis(phosphonomethyl)glycine, and a bond to the chelator;

$R^{18}$ is a bond to the chelator;
k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5; and
x' is selected from 0, 1, 2, 3, 4, and 5.

(14) A diagnostic agent according to any one of embodiments 1–13 wherein $W^1$ and $W^2$ are independently selected at each occurrence from the group: O, NH, NHC(=O), C(=O)NH, NR$^{15}$C(=O), C(=O)NR$^{15}$, C(=O), C(=O)O, OC(=O), NHC(=S)NH, NHC(=O)NH, $SO_2$, —(CH$_2$CH$_2$O)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–1 $R^{16}$, $C_{3-10}$ cycloalkyl substituted with 0–1 $R^{16}$, and a 5–10 membered heterocyclic ring system containing 1–4 heteroatoms independently selected from N, S, and O and substituted with 0–1 $R^{16}$;

$R^{13}$, $R^{13a}$, $R^{14}$, $R^{14a}$, and $R^{15}$ are independently selected at each occurrence from the group: H, =O, COOH, $SO_3H$, $C_1$–$C_5$ alkyl substituted with 0–1 $R^{16}$, aryl substituted with 0–1 $R^{16}$, benzyl substituted with 0–1 $R^{16}$ and $C_1$–$C_5$ alkoxy substituted with 0–1 $R^{16}$, NHC(=O)R$^{17}$, C(=O)NHR$^{17}$, NHC(=O)NHR$^{17}$, NHR$^{17}$, $R^{17}$, and a bond to the chelator;

k is 0 or 1;

s is selected from 0, 1, 2, 3, 4, and 5;
s' is selected from 0, 1, 2, 3, 4, and 5;
s" is selected from 0, 1, 2, 3, 4, and 5; and
t is selected from 0, 1,.2, 3, 4, and 5.

(15) A diagnostic agent according to embodiment 13 wherein wherein:
$W^1$ is C(=O)NR$^{15}$;
h is 1;
g is 3;
$R^{13}$ and $R^{14}$ are independently H;
x is 1;
k is 0;
g' is 0;
h' is 1;
$W^2$ is NH; and
x' is 1.

(16) A diagnostic agent according to embodiment 13 wherein
x is 0;
k is 1;
Z is aryl substituted with 0–3 $R^{16}$;
g' is 1;
$W^2$ is NH;
$R^{13a}$ and $R^{14a}$ are independently H;
h' is 1; and
x' is 1.

(17) A diagnostic agent according to embodiment 13 wherein
$W^1$ is C(=O)NR$^{15}$;
h is 1;
g is 2;
$R^{13}$ and $R^{14}$ are independently H;
x is 1;
k is 0;
g' is 1;
$R^{13a}$ and $R^{14a}$ are independently H; or C1–5 alkyl substituted with 0–3 $R^{16}$;
$R^{16}$ is $SO_3H$;
$W^2$ is NHC(=O) or NH;
h' is 1; and
x' is 2.

(18). A diagnostic agent according to embodiment 13 wherein
$W^1$ is C(=O)NH;
h is 1;
g is 3;
$R^{13}$ and $R^{14}$ are independently H;
k is 0;
g' is 0;
x is 1;
$W^2$ is —NH(C=O)— or —(OCH$_2$CH$_2$)$_{76-84}$—;
h' is 2; and
x' is 1.

(19) A diagnostic agent according to embodiment 13 wherein
x is 0;
k is 0;
g' is 3;
h' is 1;
$W^2$ is NH; and
x' is 1.

(20) A diagnostic agent according to embodiment 13 wherein
x is 0;
Z is aryl substituted with 0–3 $R^{16}$;
k is 1;
g' is 1;

$R^{13a}R^{14a}$ are independently H;

$W^2$ is NHC(=O) or —(OCH2CH2)$_{76-84}$—; and x' is 1.

(21) A diagnostic agent according to embodiment 13 wherein $W^1$ is C=O;

g is 2;

$R^{13}$ and $R^{14}$ are independently H;

k is 0;

g' is 0;

h' is 1;

$W^2$ is NH; and x' is 1.

(22) A compound according to embodiment 1 wherein the linking group is absent.

(23) A diagnostic agent according to any one of embodiments 1–22 wherein the chelator is a metal bonding unit having a formula selected from the group:

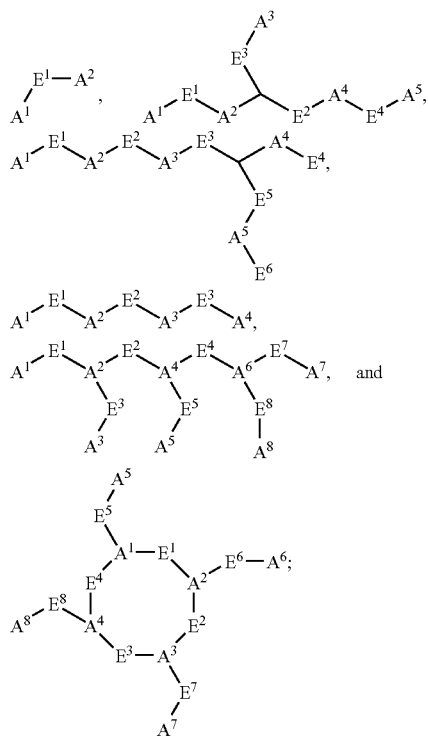

$A^1, A^2, A^3, A^4, A^5, A^6, A^7$, and $A^8$ are independently selected at each occurrence from the group: N, NR$^{26}$, NR$^{19}$, NR$^{19}$R$^{20}$, S, SH, —S(Pg), O, OH, PR$^{19}$, PR$^{19}$R$^{20}$, —O—P(O)(R$^{21}$)—O—, P(O)R$^{21}$R$^{22}$, a bond to the targeting moiety and a bond to the linking group;

Pg is a thiol protecting group;

$E^1, E^2, E^3, E^4, E^5, E^6, E^7$, and $E^8$ are independently a bond, CH, or a spacer group independently selected at each occurrence from the group: $C_1$–$C_{16}$ alkyl substituted with 0–3 $R^{23}$, aryl substituted with 0–3 $R^{23}$, $C_{3-10}$ cycloalkyl substituted with 0–3 R23, heterocyclo-$C_{1-10}$ alkyl substituted with 0–3 $R^{23}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{23}$, $C_{1-10}$ alkyl-$C_{6-10}$ aryl-substituted with 0–3 $R^{23}$, and a 5–10 membered heterocyclic ring system containing 1–4 heteroatoms independently selected from N, S, and O and substituted with 0–3 $R^{23}$;

$R^{19}$ and $R^{20}$ are each independently selected from the group: a bond to $L_n$, a bond to Q, hydrogen, $C_{1-10}$alkyl substituted with 0–3 $R^{23}$, aryl substituted with 0–3 $R^{23}$, $C_{3-10}$cycloalkyl substituted with 0–3 $R^{23}$, heterocyclo-$C_{1-10}$alkyl substituted with 0–3 $R^{23}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{23}$, $C_{1-10}$alkyl-$C_{6-10}$aryl-substituted with 0–3 $R^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{21}$ and $R^{22}$ are each independently selected from the group: a bond to the linking group, a bond to the targeting moiety, —OH, $C_1$–$C_{10}$ alkyl substituted with 0–3 $R^{23}$, $C_1$–$C_{10}$ alkyl substituted with 0–3 $R^{23}$, aryl substituted with 0–3 $R^{23}$, $C_{3-10}$ cycloalkyl substituted with 0–3 $R^{23}$, heterocyclo-$C_{1-10}$ alkyl substituted with 0–3 $R^{23}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{23}$, $C_{1-10}$ alkyl-$C_{6-10}$ aryl-substituted with 0–3 $R^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a bond to the linking group, a bond to the targeting moiety, =O, F, Cl, Br, I, —CF$_3$, —CN, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24a}$, —OR$^{24}$, —OC(=O)N(R$^{24}$)$_2$, —NR$^{25}$C(=O)R$^{24}$, —NR$^{25}$C(=O)OR$^{24a}$, —NR$^{25}$C(=O)N(R$^{24}$)$_2$, —NR$^{25}$SO$_2$N(R$^{24}$)$_2$, —NR$^{25}$SO$_2$R$^{24a}$, —SO$_3$H, SO$_2$R$^{24}$, —SR$^{24}$, —S(=O) R$^{24a}$, —SO$_2$N(R$^{24}$)$_2$, —N(R$^{24}$)$_2$, —NHC(=S)NHR$^{24}$, =NOR$^{24}$, NO$_2$, —C(=O)NHOR$^{24}$, C(=O) NHNR$^{24}$R$^{24a}$, —OCH$_2$CO$_2$H, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{24}$, and a 5–10 membered heterocyclic ring system containing 1–4 heteroatoms independently selected from N, S, and O; and wherein at least one of $A^1, A^2, A^3, A^4, A^5, A^6, A^7, A^8$ or $R^{23}$ is a bond to the linking group or targeting moiety;

$R^{24}$, $R^{24a}$, and $R^{25}$ are independently selected at each occurrence from the group: a bond to the linking group, a bond to the targeting moiety, H, $C_1$–$C_6$ alkyl, phenyl, benzyl, $C_1$–$C_6$ alkoxy, halide, nitro, cyano, and trifluoromethyl; and $R^{26}$ is a co-ordinate bond to a metal or a hydrazine protecting group; or a pharmaceutically acceptable salt thereof.

(24) A diagnostic agent according to any one of embodiments 1–23 wherein:

$A^1, A^2, A^3, A^4, A^5, A^6, A^7$, and $A^8$ are independently selected at each occurrence from the group: NR$^{19}$, NR$^{19}$R$^{20}$, S, SH, OH, a bond to the targeting moiety and a bond to the linking group;

$E^1, E^2, E^3, E^4, E^5, E^6, E^7$, and $E^8$ are independently a bond, CH, or a spacer group independently selected at each occurrence from the group: $C_1$–$C_{10}$ alkyl substituted with 0–3 $R^{23}$, aryl substituted with 0–3 $R^{23}$, $C_{3-10}$ cycloalkyl substituted with 0–3 $R^{23}$, and a 5–10 membered heterocyclic ring system containing 1–4 heteroatoms independently selected from N, S, and O and substituted with 0–3 $R^{23}$;

wherein at least one of $A^1, A^2, A^3, A^4, A^5, A^6, A^7, A^8$ and $R^{23}$ is a bond to the linking group or the targeting moiety;

$R^{19}$, and $R^{20}$ are each independently selected from the group: a bond to the targeting moiety, a bond to the linking group, hydrogen, $C_1$–$C_{10}$ alkyl substituted with 0–3 $R^{23}$, aryl substituted with 0–3 $R^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{23}$ is independently selected at each occurrence from the group: a bond to the targeting moiety, a bond to the linking group, =O, F, Cl, Br, I, —$CF_3$, —CN, —$CO_2R^{24}$, —C(=O)$R^{24}$, —C(=O)N($R^{24}$)$_2$, —$CH_2OR^{24}$, —OC(=O)$R^{24}$, —OC(=O)O$R^{24a}$, —O$R^{24}$, —OC(=O)N($R^{24}$)$_2$, —$NR^{25}$C(=O)$R^{24}$, —$NR^{25}$C(=O)O$R^{24a}$, —$NR^{25}$C(=O)N($R^{24}$)$_2$, —$NR^{25}SO_2N(R^{24})_2$, —$NR^{25}SO_2R^{24a}$, —$SO_3H$, —$SO_2R^{24a}$, —S(=O)$R^{24a}$, —$SO_2N(R^{24})_2$, —N($R^{24}$)$_2$, —NHC(=S)NH$R^{24}$, =NO$R^{18}$, —C(=O)NHN$R^{18}R^{18a}$, —OCH$_2$CO$_2$H, and 2-(1-morpholino)ethoxy; and $R^{24}$, $R^{24a}$, and $R^{25}$ are independently selected at each occurrence from the group: a bond to the linking group, H, and $C_1$–$C_6$ alkyl.

(25) A diagnostic agent according to any one of embodiments 1–24 wherein the chelator is of the formula:

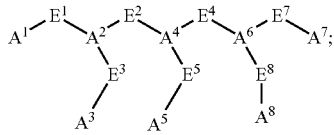

$A^1$ is a bond to the linking group;
$A^2$, $A^4$, and $A^6$ are each N;
$A^3$, $A^5$, $A^7$ and $A^8$ are each OH;
$E^1$, $E^2$, and $E^4$ are C2 alkyl;
$E^3$, $E^5$, $E^7$, and $E^8$ are $C_2$ alkyl substituted with 0–1 $R^{23}$;
$R^{23}$ is =O.

(26) A diagnostic agent according to any one of embodiments 1–25 wherein the chelator is of the formula:

$C_h$ is

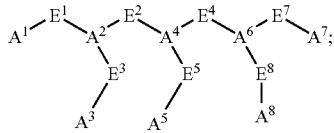

wherein:
A5 is a bond to Ln;
$A^1$, $A^3$, $A^7$ and $A^8$ are each OH;
$A^2$, $A^4$ and $A^6$ are each NH;
$E^1$, $E^3$, $E^5$, $E^7$, and $E^8$ are $C_2$ alkyl substituted with 0–1 $R^{23}$;
$E^2$, and $E^4$, are $C_2$ alkyl;
$R^{23}$ is =O.

(27) A diagnostic agent according to any one of embodiments 1–26 wherein the chelator is of the formula:

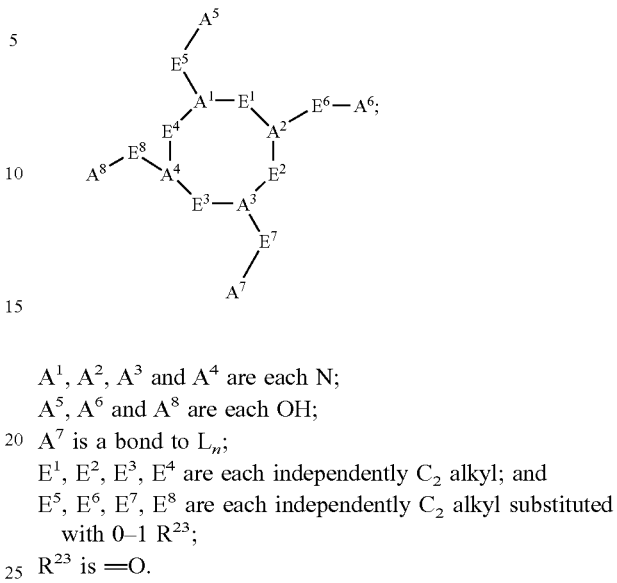

$A^1$, $A^2$, $A^3$ and $A^4$ are each N;
$A^5$, $A^6$ and $A^8$ are each OH;
$A^7$ is a bond to $L_n$;
$E^1$, $E^2$, $E^3$, $E^4$ are each independently $C_2$ alkyl; and
$E^5$, $E^6$, $E^7$, $E^8$ are each independently $C_2$ alkyl substituted with 0–1 $R^{23}$;
$R^{23}$ is =O.

(28) A diagnostic agent according to any one of embodiments 1–27 wherein the chelator is of the formula:

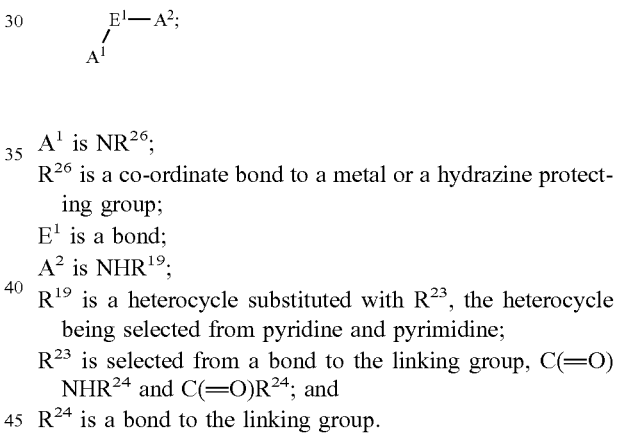

$A^1$ is $NR^{26}$;
$R^{26}$ is a co-ordinate bond to a metal or a hydrazine protecting group;
$E^1$ is a bond;
$A^2$ is $NHR^{19}$;
$R^{19}$ is a heterocycle substituted with $R^{23}$, the heterocycle being selected from pyridine and pyrimidine;
$R^{23}$ is selected from a bond to the linking group, C(=O)NH$R^{24}$ and C(=O)$R^{24}$; and
$R^{24}$ is a bond to the linking group.

(29) A diagnostic agent according to any one of embodiments 1–28 wherein the chelator is of the formula:

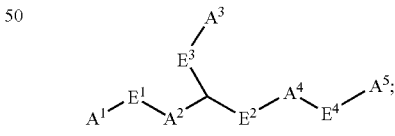

wherein:
$A^1$ and $A^5$ are each —S(Pg);
Pg is a thiol protecting group;
$E^1$ and $E^4$ are $C_2$ alkyl substituted with 0–1 $R^{23}$;
$R^{23}$ is =O;
$A^2$ and $A^4$ are each —NH;
$E^2$ is $CH_2$;
$E^3$ is $C_{1-3}$ alkyl substituted with 0–1 $R^{23}$;
$A^3$ is a bond to Ln.

(30) A diagnostic agent according to any one of embodiments 1–29 wherein the chelator is of the formula:

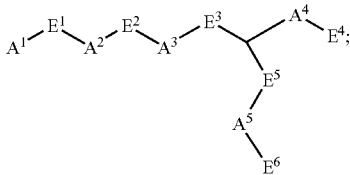

wherein:
$A^1$ is a bond to Ln;
$E^1$ is $C_1$ alkyl substituted by $R^{23}$;
A is NH;
$E^2$ is $C_2$ alkyl substituted with 0–1$R^{23}$;
$A^3$ is —O—P(O)($R^{21}$)—O;
$E^3$ is $C_1$ alkyl;
$A^4$ and $A^5$ are each —O—;
$E^4$ and $E^6$ are each independently $C_{1-16}$ alkyl substituted with 0–1$R^{23}$;
$E^5$ is $C_1$ alkyl;
$R^{21}$ is —OH; and
$R^{23}$ is =O.

(31) A diagnostic agent according to embodiment 1 having the formula:

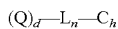

(Q)$_d$—L$_n$—C$_h$ wherein, Q is a compound of Formulae (Ia) or (Ib):

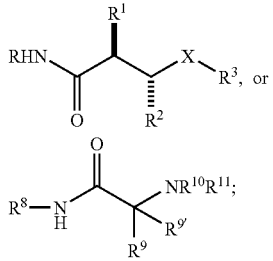

wherein,
R is independently OH or —CH$_2$SH;
$R^1$ is independently selected at each occurrence from the group: H, OH, $C_{1-3}$ alkyl, $C_{2-3}$ alkenyl, $C_{2-3}$ alkynyl, and heterocycle-S—CH$_2$—;
$R^2$ is independently $C_{1-20}$ alkyl;
X is independently C=O or SO$_2$, provided when X is C=O, $R^3$ is

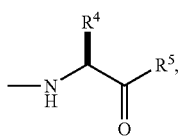

and when X is SO$_2$, $R^3$ is independently selected from the group: aryl substituted with 0–2 $R^6$, and heterocycle substituted with 0–2 $R^6$;
$R^4$ is independently selected at each occurrence from the group: $C_{1-6}$ alkyl, phenyl, and benzyl;
$R^5$ is independently at each occurrence from the group: NH($C_{1-6}$ alkyl), NH-phenyl, and NH-heterocycle; wherein said alkyl, phenyl and heterocycle groups are optionally substituted with a bond to $L_n$;
$R^6$ is independently aryloxy substituted with 0–3 $R^7$;

$R^7$ is independently halogen or methoxy;
or alternatively,
$R^1$ and $R^4$ may be taken together to form a bridging group of the formula —(CH$_2$)$_3$—O-phenyl-CH$_2$—, optionally substituted with a bond to $L_n$;
or alternatively,
$R^1$ and $R^2$ may be taken together to form a bridging group of the formula —(CH$_2$)$_3$—NH—, optionally substituted with a bond to $L_n$; or
$R^1$ and $R^2$ taken together with the nitrogen and carbon atom through which they are attached form a $C_{5-7}$ atom saturated ring system substituted with one or more substituents selected from the group consisting of: a bond to Ln, a bond to Ch, and —C(=O)—NR$^{29}$R$^{30}$;
$R^8$ is independently at each occurrence OH or phenyl, optionally substituted with a bond to $L_n$, provided that when $R^8$ is phenyl, $R^{10}$ is —C(=O)—CR$^{12}$—NH—CH(CH$_3$)—COOH;
$R^9$ and $R^{9\prime}$ are independently H, $C_{1-6}$ alkyl optionally substituted with a bond to $L_n$, or are taken together with the carbon atom to which they are attached to form a 5–7 atom saturated, partially unsaturated or aromatic ring system containing 0–3 heteroatoms selected from O, N, SO$_2$ and S, said ring system substituted with $R^6$ and optionally substituted with a bond to $L_n$;
$R^{10}$ and $R^{11}$ are independently H, or $C_{1-6}$ alkyl optionally substituted with a bond to Ln, or are taken together with the nitrogen atom to which they are attached to form a 5–7 atom saturated, partially unsaturated or aromatic ring system containing 0–3 heteroatoms selected from O, N, SO$_2$ and S, said ring system optionally substituted with 0–3 $R^{27}$ or a bond to $L_n$;
or alternatively,
$R^9$ and $R^{10}$ are taken together with the carbon atom to which they are attached to form a 5–7 atom saturated, partially unsaturated or aromatic-ring system containing 0–3 heteroatoms selected from O, N, SO$_2$ and S, said ring system optionally substituted with a bond to $L_n$;
$R^{12}$ is independently $C_{1-20}$ alkyl;
d is selected from 1, 2, 3, 4, 5, 6, 7, 8, 9, and 10;
$L_n$ is a linking group having the formula:

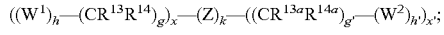

$W^1$ and $W^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;
aa is independently at each occurrence an amino acid;
Z is selected from the group: aryl substituted with 0–3 $R^{16}$, $C_{3-10}$ cycloalkyl substituted with 0–3 $R^{16}$, and a 5–10 membered heterocyclic ring system containing 1–4 heteroatoms independently selected from N, S, and O and substituted with 0–3 $R^{16}$;
$R^{13}$, $R^{13a}$, $R^{14}$, $R^{14a}$, and $R^{15}$ are independently selected at each occurrence from the group: H, =O, COOH, SO$_3$H, PO$_3$H, $C_1$–$C_5$ alkyl substituted with 0–3 $R^{16}$, aryl substituted with 0–3 $R^{16}$, benzyl substituted with 0–3 $R^{16}$, and $C_1$–$C_5$ alkoxy substituted with 0–3 $R^{16}$, NHC(=O)R$^{17}$, C(=O)NHR$^{17}$, NHC(=O)NHR$^{17}$, NHR$^{17}$, R$^{17}$, and a bond to C$_h$;
$R^{16}$ is independently selected at each occurrence from the group: a bond to C$_h$, COOR$^{17}$, C(=O)NHR$^{17}$, NHC(=O)R$^{17}$, OH, NHR$^{17}$, SO$_3$H, PO$_3$H, —OPO$_3$H$_2$, —OSO$_3$H, aryl substituted with 0–3 $R^{17}$, $C_{1-5}$ alkyl substituted with 0–1 $R^{18}$, $C_{1-5}$ alkoxy substituted with 0–1

R¹⁸, and a 5–10 membered heterocyclic ring system containing 1–4 heteroatoms independently selected from N, S, and O and substituted with 0–3 R¹⁷;

R¹⁷ is independently selected at each occurrence from the group: H, alkyl substituted with 0–1 R¹⁸, aryl substituted with 0–1 R¹⁸, a 5–10 membered heterocyclic ring system containing 1–4 heteroatoms independently selected from N, S, and O and substituted with 0–1 R¹⁸, $C_{3-10}$ cycloalkyl substituted with 0–1 R¹⁸, polyalkylene glycol substituted with 0–1 R¹⁸, carbohydrate substituted with 0–1 R¹⁸, cyclodextrin substituted with 0–1 R¹⁸, amino acid substituted with 0–1 R¹⁸, polycarboxyalkyl substituted with 0–1 R¹⁸, polyazaalkyl substituted with 0–1 R¹⁸, peptide substituted with 0–1 R¹⁸, wherein the peptide is comprised of 2–10 amino acids, 3,6-O-disulfo-B-D-galactopyranosyl, bis(phosphonomethyl)glycine, and a bond to $C_h$;

R¹⁸ is a bond to $C_h$;

k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5;
x' is selected from 0, 1, 2, 3, 4, and 5;

$C_h$ is a metal bonding unit having a formula selected from the group:

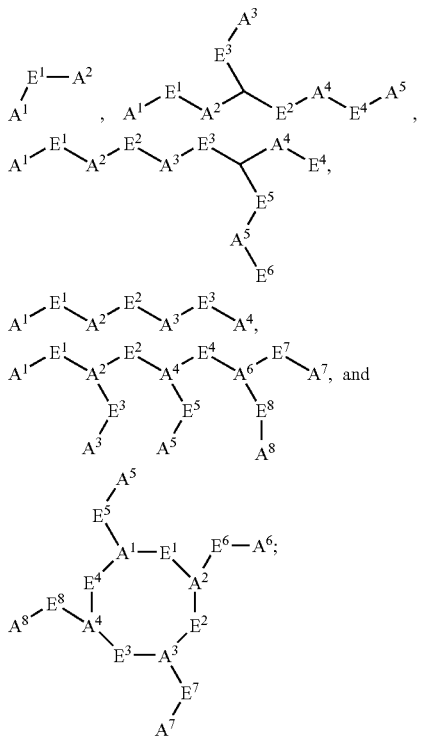

$A^1, A^2, A^3, A^4, A^5, A^6, A^7$, and $A^8$ are independently selected at each occurrence from the group: N, NR²⁶, NR¹⁹, NR¹⁹R²⁰, S, SH, —S(Pg), O, OH, PR¹⁹, PR¹⁹R²⁰, —O—P(O)(R²¹)—O—, P(O)R²¹R²², a bond to the targeting moiety and a bond to the linking group;

Pg is a thiol protecting group;

$E^1, E^2, E^3, E^4, E^5, E^6, E^7$, and $E^8$ are independently a bond, CH, or a spacer group independently selected at each occurrence from the group: $C_1$–$C_{16}$ alkyl substituted with 0–3 R²³, aryl substituted with 0–3 R²³, $C_{3-10}$ cycloalkyl substituted with 0–3 R²³, heterocyclo-$C_{1-10}$ alkyl substituted with 0–3 R²³, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 R²³, $C_{1-10}$ alkyl-$C_{6-10}$ aryl-substituted with 0–3 R²³, and a 5–10 membered heterocyclic ring system containing 1–4 heteroatoms independently selected from N, S, and O and substituted with 0–3 R²³;

R¹⁹ and R²⁰ are each independently selected from the group: a bond to the linking group, a bond to the targeting moiety, hydrogen, $C_1$–$C_{10}$ alkyl substituted with 0–3 R²³, aryl substituted with 0–3 R²³, $C_{3-10}$cyclalkyl substituted with 0–3 R²³, heterocyclo-$C_{1-10}$alkyl substituted with 0–3 R²³, wherein the heterocyclo group is a 5–10 membered heterocyclic ring system containing 1–4 heteroatoms independently selected from N, S, and O, $C_{6-10}$aryl-$C_{1-10}$alkyl substituted with 0–3 R²³; $C_{1-10}$alkyl-$C_{6-10}$aryl-substituted with 0–3 R²³, a 5–10 membered heterocyclic ring system containing 1–4 heteroatoms independently selected from N, S, and O and substituted with 0–3 R²³, and an electron, provided that when one of R¹⁹ or R²⁰ is an electron, then the other is also an electron;

R²¹ and R²² are each independently selected from the group: a bond to the linking group, a bond to the targeting moiety, —OH, $C_1$–$C_{10}$ alkyl substituted with 0–3 R²³, $C_1$–$C_{10}$ alkyl substituted with 0–3 R²³, aryl substituted with 0–3 R²³, $C_{3-10}$ cycloalkyl substituted with 0–3 R²³, heterocyclo-$C_{1-10}$ alkyl substituted with 0–3 R²³, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 R²³, $C_{1-10}$ alkyl-$C_{6-10}$ aryl-substituted with 0–3 R²³, and a 5–10 membered heterocyclic ring system containing 1–4 heteroatoms independently selected from N, S, and O and substituted with 0–3 R²³;

R²³ is independently selected at each occurrence from the group: a bond to the linking group, a bond to the targeting moiety, =O, F, Cl, Br, I, —CF₃, —CN, —CO₂R²⁴, —C(=O)R²⁴, —C(=O)N(R²⁴)₂, —CHO, —CH₂OR²⁴, —OC(=O)R²⁴, —OC(=O)OR²⁴ᵃ, —OR²⁴, —OC(=O)N(R²⁴)₂, —NR²⁵C(=O)R²⁴, —NR²⁵C(=O)OR²⁴ᵃ, —NR²⁵C(=O)N(R²⁴)₂, —NR²⁵SO₂N(R²⁴)₂, —NR²⁵SO₂R²⁴ᵃ, —SO₃H, —SO₂R²⁴ᵃ, —SR²⁴, —S(=O)R²⁴ᵃ, —SO₂N(R²⁴)₂, —N(R²⁴)₂, —NHC(=S)NHR²⁴, =NOR²⁴, NO₂, —C(=O)NHOR²⁴, —C(=O)NHNR²⁴R²⁴ᵃ, —OCH₂CO₂H, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 R²⁴, and a 5–10 membered heterocyclic ring system containing 1–4 heteroatoms independently selected from N, S, and O; and wherein at least one of $A^1, A^2, A^3, A^4, A^5, A^6, A^7, A^8$ or R²³ is a bond to the linking group or targeting moiety;

R²⁴, R²⁴ᵃ, and R²⁵ are independently selected at each occurrence from the group: a bond to the linking group, a bond to the targeting moiety, H, $C_1$–$C_6$ alkyl, phenyl, benzyl, $C_1$–$C_6$ alkoxy, halide, nitro, cyano, and trifluoromethyl; and R²⁶ is a, co-ordinate bond to a metal or a hydrazine protecting group; or a pharmaceutically acceptable salt thereof.

(32) A diagnostic agent according to Embodiment 31, wherein:
h' is 1;
W² is NH; and
x' is 1.
(33) A diagnostic agent according to any one of embodiments 1–32, wherein:
x is 0;
Z is aryl substituted with 0–3 R¹⁶;
k is 1;
g' is 1;
R¹³ᵃR¹⁴ᵃ are independently H;
W² is NHC(=O) or —(OCH2CH2)₇₆₋₈₄—; and
x' is 1.
(34) A diagnostic agent according to any one of embodiments 31–33, wherein:
W¹ is C=O;
g is 2;
R¹³ and R¹⁴ are independently H;
k is 0;
g' is 0;
h' is 1;
W² is NH; and
x' is 1.
(35) A diagnostic agent according to to any one of embodiments 31–34, wherein:
2-{[5-(3-{2-[(6-Hydroxycarbamoyl-7-isobutyl-8-oxo-2-oxa-9-aza-bicyclo[10.2.2]hexadeca-1(15),12(16),13-triene-10-carbonyl)-amino]-acetylamino}-propylcarbamoyl)-pyridin-2-yl]-hydrazonomethyl}-benzenesulfonic acid;
2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzenesulfonic acid;
2-[7-({N-[3-(2-{[7-(N-hydroxycarbamoyl)(3S,6R,7S)-4-aza-6-(2-methylpropyl)-11-oxa-5-oxobicyclo[10.2.2] hexadeca-1(15),12(16),13-trien-3-yl] carbonylamino}acetylamino)propyl]carbamoyl}methyl)-1,4,7,10-tetraaza-4,10-bis(carboxymethyl)cyclododecyl] acetic acid;
2-{7-[(N-{[4-({[7-(N-hydroxycarbamoyl)(3S,6R,7S)-4-aza-6-(2-methylpropyl)-11-oxa-5-oxobicyclo[10.2.2] hexadeca-1(15),12(16),13-trien-3-yl]-carbonylamino}methyl)phenyl]methyl}carbamoyl)methyl]-1,4,7,10-tetraaza-4,10-bis(carboxymethyl) cyclododecyl}acetic acid;
2-(7-{[N-(1-{N-[3-(2-{[7-(N-hydroxycarbamoyl)(3S,6R, 7S)-4-aza-6-(2-methylpropyl)-11-oxa-5-oxobicyclo[10.2.2] hexadeca-1(15),12(16),13-trien-3-yl] carbonylamino}acetylamino)propyl]carbamoyl}-2-sulfoethyl)carbamoyl]methyl}-1,4,7,10-tetraaza-4,10-bis (carboxymethyl)cyclododecyl)acetic acid;
2-[7-({N-[1-(N-{[4-({[7-(N-hydroxycarbamoyl)(3S,6R, 7S)-4-aza-6-(2-methylpropyl)-11-oxa-5-oxobicyclo[10.2.2] hexadeca-1(15),12(16),13-trien-3-yl]-carbonylamino}methyl)phenyl]methyl}carbamoyl)-2-sulfoethyl]carbamoyl}methyl)-1,4,7,10-tetraaza-4,10-bis (carboxymethyl)cyclododecyl]acetic acid;
2-({2-[({N-[3-(2-{[7-(N-hydroxycarbamoyl)(3S,6R,7S)-4-aza-6-(2-methylpropyl)-11-oxa-5-oxobicyclo[10.2.2] hexadeca-1(15),12(16),13-trien-3-yl] carbonylamino}acetylamino)propyl]carbamoyl}methyl), (carboxymethyl)amino}ethyl){2-[bis(carboxymethyl) amino]ethyl}amino]acetic acid;
2-[(2-{[(N-{[4-({[7-(N-hydroxycarbamoyl)(3S,6R,7S)-4-aza-6-(2-methylpropyl)-11-oxa-5-oxobicyclo[10.2.2] hexadeca-1(15),12(16),13-trien-3-yl]-carbonylamino}methyl)phenyl]methyl}carbamoyl)methyl] (carboxymethyl)amino}ethyl){2-[bis(carboxymethyl) amino]ethyl}amino]acetic acid;
N-[3-(2-{[7-(N-hydroxycarbamoyl)(3S,6R,7S)-4-aza-6-(2-methylpropyl)-11-oxa-5-oxobicyclo[10.2.2]hexadeca-1 (15),12(16),13-trien-3-yl]carbonylamino}acetylamino) propyl]-4,5-bis[2-(ethoxyethylthio)acetylamino] pentanamide;
N-{[4-({[7-(N-hydroxycarbamoyl)(3S,6R,7S)-4-aza-6-(2-methylpropyl)-11-oxa-5-oxobicyclo[10.2.2]hexadeca-1 (15),12(16),13-trien-3-yl]carbonylamino}methyl)-phenyl] methyl}-4,5-bis[2-(ethoxyethylthio)acetylamino]-pentanamide;
1-(1,2-Dipalmitoyl-sn-glycero-3-phosphoethanolamino)-α, ω-dicarbonylPEG₃₄₀₀₋₂-{[7-(N-hydroxycarbamoyl)(3S,6R, 7S)-4-aza-6-(2-methylpropyl)-11-oxa-5-oxobicyclo[10.2.2] hexadeca-1(15),12(16),13-trien-3-yl]carbonylamino}-N-(3-aminopropyl)acetamide;
1-(1,2-Dipalmitoyl-sn-glycero-3-phosphoethanolamino)-α, ω-dicarbonylPEG₃₄₀₀-[7-(N-hydroxycarbamoyl)(3S, 6R, 7S)-4-aza-6-(2-methylpropyl)-11-oxa-5-oxobicyclo[10.2.2] hexadeca-1(15), 12(16), 13-trien-3-yl]-N-{[4-(aminomethyl)phenyl]methyl}carboxamide conjugate;
2-[2-({5-[N-(5-(N-hydroxycarbamoyl)(5R)-5-{3-[4-(3,4-dimethoxyphenoxy)phenyl]-3-methyl-2-oxopyrrolidinyl}pentyl)carbambyl](2-pyridyl)}amino)(1Z)-2-azavinyl]benzenesulfonic acid;
2-(2-{[5-N-{3-[3-(N-hydroxycarbamoyl)(4S)-4-({4-[(4-methylphenyl)methoxy]piperidyl}carbonyl)piperidyl]-3-oxopropyl}carbamoyl)(2-pyridyl)]amino}(1Z)-2-azavinyl) benzenesulfonic acid; and

(36) A diagnostic agent according to to any one of embodiments 31–35 wherein the diagnostic metal is selected from the group consisting of: a paramagnetic metal, a ferromagnetic metal, a gamma-emitting radioisotope, or an x-ray absorber.
(37) A diagnostic agent according to to any one of embodiments 31–36 wherein the diagnostic metal is radioisotope selected from the group consisting of $^{99m}$Tc, $^{95}$Tc, $^{111}$In, $^{62}$Cu, $^{64}$Cu, $^{67}$Ga, and $^{68}$Ga.
(38). A diagnostic agent according to to any one of embodiments 31–37 further comprising a first ancillary ligand and a second ancillary ligand capable of stabilizing the radioisotope.
(39) A diagnostic agent according to Embodiment 37, wherein the radioisotope is $^{99m}$Tc.
(40) A diagnostic agent according to Embodiment 37, wherein the radioisotope is $^{111}$In.
(41) A diagnostic agent according to embodiment 36 wherein the paramagnetic metal ion is selected from the group consisting of Gd(III), Dy(III), Fe(III), and Mn(II).
(42). A diagnostic agent according to embodiment 36 wherein the x-ray absorber is a metal is selected from the group consisting of: Re, Sm, Ho, Lu, Pm, Y, Bi, Pd, Gd, La, Au, Au, Yb, Dy, Cu, Rh, Ag, and Ir.
(43) A diagnostic composition comprising a compound according to any one of embodiments 1–42 or a pharmaceutically acceptable salt thereof, and a pharmaceutically acceptable carrier.
(44) A kit comprising a compound of to any one of embodiments 1–42, or a pharmaceutically acceptable salt form thereof and a pharmaceutically acceptable carrier.
(45) A kit according to Embodiment 44, wherein the kit further comprises one or more ancillary ligands and a reducing agent.
(46) A kit according to Embodiment 45, wherein the ancillary ligands are tricine and TPPTS.
(47) A kit according to Embodiment 45, wherein the reducing agent is tin(II).
(48) A diagnostic agent comprising an echogenic gas and a compound, wherein the compound comprises:
i) 1–10 targeting moieties;
ii) a surfactant (Sf); and
iii) 0–1 linking groups between the targeting moiety and surfactant;
wherein the targeting moiety is a matrix metalloproteinase inhibitor; and
wherein the surfactant is capable of forming an echogenic gas filled lipid sphere or microbubble.
(49) A diagnostic agent according to embodiment 48, wherein the. targeting moiety is a matrix metalloproteinase inhibitor having an inhibitory constant $K_i$ of <1000 nM.
(50) A diagnostic agent according to any one of embodiments 48–49, wherein the targeting moiety is a matrix metalloproteinase inhibitor having an inhibitory constant $K_i$ of <100 nM.
(51) A diagnostic agent according to embodiment 48, comprising 1–5 targeting moieties.
(52). A diagnostic agent according to embodiment 48, comprising one targeting moiety.
(53) A diagnostic agent according to any one of embodiments 48–52, wherein the targeting moiety is an inhibitor of one or more matrix metalloproteinases selected from the group consisting of MMP-1, MMP-2, MMP-3, MMP-9, and MMP-14.
(54) A diagnostic agent according to any one of embodiments 48–53, wherein the targeting moiety is an inhibitor of one or more matrix metalloproteinases selected from the group consisting of MMP-2, MMP-9, and MMP-14.

(55) A diagnostic agent according to embodiment 48, wherein the targeting moiety is of the formulae (Ia) or (Ib):

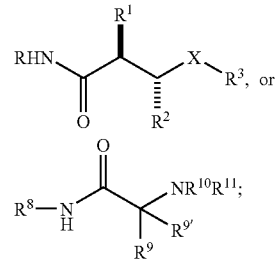

wherein,
R is independently OH or —CH$_2$SH;
R$^1$ is independently selected at each occurrence from the group: H, OH, C$_{1-3}$ alkyl, C$_{2-3}$ alkenyl, C$_{2-3}$ alkynyl, and heterocycle-S—CH$_2$—;
R$^2$ is independently C$_{1-20}$ alkyl;
X is independently C=O or SO$_2$, provided when X is C=O, R$^3$ is

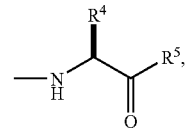

and when X is SO$_2$, R$^3$ is independently selected from the group: aryl substituted with 0–2 R$^6$, and heterocycle substituted with 0–2 R$^6$;
R$^4$ is independently selected at each occurrence from the group: C$_{1-6}$ alkyl, phenyl, and benzyl;
R$^5$ is independently at each occurrence from the group: NH(C$_{1-6}$ alkyl), NH-phenyl, and NH-heterocycle; wherein said alkyl, phenyl and heterocycle groups are optionally substituted with a bond to the linking group or a bond to the surfactant;
R$^6$ is independently aryloxy substituted with 0–3 R$^7$;
R$^7$ is independently halogen or methoxy;
or alternatively,
R$^1$ and R$^4$ may be taken together to form a bridging group of the formula —(CH$_2$)$_3$—O-phenyl-CH$_2$—, optionally substituted with a bond to the linking group or a bond to the surfactant;
or alternatively,
R$^1$ and R$^2$ may be taken together to form a bridging group of the formula —(CH$_2$)$_3$—NH—, optionally substituted with a bond to the linking group or a bond to the surfactant; or
R$^1$ and R$^2$ taken together with the nitrogen and carbon atom through which they are attached form a C$_{5-7}$ atom saturated ring system substituted with one or more substituents selected from the group consisting of: a bond to Ln, a bond to Sf, and —C(=O)—NR$^{29}$R$^{30}$;
R$^8$ is independently at each occurrence OH or phenyl, optionally substituted with a bond to the linking group or a bond to the surfactant, provided that when R$^8$ is phenyl, R$^{10}$ is —C(=O)—CR$^{12}$—NH—CH(CH$_3$)—COOH;
R$^9$ and R$^{9'}$ are independently H, C$_{1-6}$ alkyl optionally substituted with a bond to the linking group or a bond to the surfactant, or are taken together with the carbon atom to which R$^9$ and R$^{9'}$ are attached to form a 5–7 atom saturated, partially unsaturated or aromatic ring system containing 0–3 heteroatoms selected from O, N, SO$_2$ and S, said ring system substituted with R$^6$ and optionally substituted with a bond to the linking group or a bond to the surfactant;

$R^{10}$ and $R^{11}$ are independently H, or $C_{1-6}$ alkyl optionally substituted with a bond to the linking group or a bond to the surfactant, or are taken together with the nitrogen atom to which they are attached to form a 5–7 atom saturated, partially unsaturated or aromatic ring system containing 0–3 heteroatoms selected from O, N, $SO_2$ and S, said ring system optionally substituted with 0–3 $R^{27}$, a bond to the linking group or a bond to the surfactant;

or alternatively, $R^9$ and $R^{10}$ are taken together with the carbon atom to which they are attached to form a 5–7 atom saturated, partially unsaturated or aromatic ring system containing 0–3 heteroatoms selected from O, N, $SO_2$ and S, said ring system optionally substituted with a bond to the linking group or a bond to the surfactant; and $R^{12}$ is independently $C_{1-20}$ alkyl;

$R^{27}$ is =O, $C_{1-4}$ alkyl, or phenyl substituted with $R^{28}$;

$R^{28}$ is a phenoxy group substituted with 0–2 $OCH_3$ groups;

$R^{29}$ and $R^{30}$ taken together with the nitrogen atom through which they are attached form a C5–7 atom saturated ring system substituted with $R^{31}$; and $R^{31}$ is a benzyloxy group substituted with C1–4 alkyl.

(56) A diagnostic agent according to embodiment 55 wherein wherein the targeting moiety is a matrix metalloproteinase inhibitor of the formulae (Ia) or (Ib):

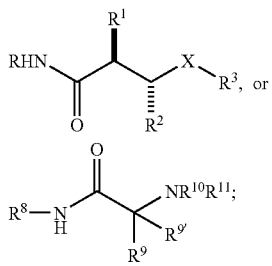

wherein,

R is OH;

$R^1$ is independently selected at each occurrence from the group: H, OH, $C_{1-3}$ alkyl, $C_{2-3}$ alkenyl, $C_{2-3}$ alkynyl, and heterocycle-S—$CH_2$—;

$R^2$ is independently $C_{1-6}$ alkyl;

X is C=O;

$R^4$ is independently selected at each occurrence from the group: $C_{1-6}$ alkyl, phenyl, and benzyl;

$R^5$ is independently at each occurrence from the group: NH($C_{1-6}$ alkyl), NH-phenyl, and NH-heterocycle; wherein said alkyl, phenyl and heterocycle groups are optionally substituted with a bond to the linking group or a bond to the surfactant;

$R^6$ is independently aryloxy substituted with 0–3 $R^7$;

$R^7$ is independently halogen or methoxy;

or alternatively, $R^1$ and $R^4$ may be taken together to form a bridging group of the formula —$(CH_2)_3$—O-phenyl-$CH_2$—, optionally substituted with a bond to the linking group or a bond to the surfactant;

or alternatively, $R^1$ and $R^2$ may be taken together to form a bridging group of the formula —$(CH_2)_3$—NH—, optionally substituted with a bond to the linking group or a bond to the surfactant; or $R^1$ and $R^2$ taken together with the nitrogen and carbon atom through which they are attached form a $C_{5-7}$ atom saturated ring system substituted with one or more substituents selected from the group consisting of: a bond to Ln, a bond to Sf, and —C(=O)—$NR^{29}R^{30}$;

$R^8$ is OH;

$R^9$ and $R^{9'}$ are independently H, $C_{1-6}$ alkyl optionally substituted with a bond to the linking group or a bond to the surfactant, or are taken together with the carbon atom to which $R^9$ and $R^{9'}$ are attached to form a 5–7 atom saturated, partially unsaturated or aromatic ring system containing 0–1 heteroatoms selected from O, N, said ring system optionally substituted with a bond to the linking group or a bond to the surfactant;

$R^{10}$ and $R^{11}$ are independently H, or $C_{1-6}$ alkyl optionally substituted with a bond to the linking group or a bond to the surfactant, or are taken together with the nitrogen atom to which they are attached to form a 5–7 atom saturated, partially unsaturated or aromatic ring system containing 0–1 heteroatoms selected from O, N, said ring system optionally substituted with 0–3 $R^{27}$, a bond to the linking group or a bond to the surfactant;

or alternatively, $R^9$ and $R^{10}$ are taken together with the carbon atom to which they are attached to form a 5–7 atom saturated, partially unsaturated or aromatic ring system containing 0–1 heteroatoms selected from O, N, said ring system optionally substituted with a bond to the linking group or a bond to the surfactant; and $R^{12}$ is independently $C_{1-6}$ alkyl;

$R^{27}$ is =O, C1–4 alkyl, or phenyl substituted with $R^{28}$;

$R^{28}$ is a phenoxy group substituted with 0–2 $OCH_3$ groups;

$R^{29}$ and $R^{30}$ taken together with the nitrogen atom through which they are attached form a C5–7 atom saturated ring system substituted with $R^{31}$; and $R^{31}$ is a benzyloxy group substituted with C1–4 alkyl.

(57) A diagnostic agent according to any one of embodiments 55–57 wherein the targeting moiety is a matrix metalloproteinase inhibitor of the formulae (Ia) or (Ib): wherein:

R is —OH;

$R^2$ is $C_{1-6}$ alkyl;

X is C=O;

$R^3$ is $$\begin{array}{c} R^4 \\ | \\ -N-\underset{\underset{O}{\|}}{C}-R^5; \\ H \end{array}$$

$R^1$ and $R^4$ are taken together to form a bridging group of formula —$(CH_2)_3$—O-phenyl-$CH_2$—;

$R^5$ is NH(C1–6alkyl), substituted with a bond to the linking group or a bond to the surfactant.

(58) A diagnostic agent according to any one of embodiments 55–57 wherein:

R is —OH;

$R^9$ is $C_1$ alkyl substituted with a bond to Ln;

$R^{10}$ and $R^{11}$ taken together with the nitrogen atom to which they are attached form a 5 atom saturated ring system, said right system is substituted with 0–3 $R^{27}$;

$R^{27}$ is =O, C1–4 alkyl, or phenyl substituted with $R^{28}$; and $R^{28}$ is a phenoxy group substituted with 0–2 $OCH_3$ groups.

(59) A diagnostic agent according to any one of embodiments 55–58 wherein

R is —OH;

$R^1$ and $R^2$ taken together with the nitrogen and carbon atom through which they are attached form a $C_{5-7}$ atom saturated ring system substituted with one or more substituents selected from the group consisting of: a bond to Ln, a bond to Sf, and —C(=O)—NR$^{29}$R$^{30}$;

R$^{29}$ and R$^{30}$ taken together with the nitrogen atom through which they are attached form a C5–7 atom saturated ring system substituted with R$^{31}$; and R$^{31}$ is a benzyloxy group substituted with C1–4 alkyl.

(60) A diagnostic agent according to any one of embodiments 48–59 wherein the linking group is of the formula:

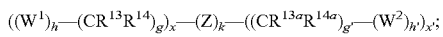

W$^{1}$ and W$^{2}$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–3 R$^{16}$, C$_{3-10}$ cycloalkyl substituted with 0–3 R$^{16}$, and a 5–10 membered heterocyclic ring system containing 1–4 heteroatoms independently selected from N, S, and O and substituted with 0–3 R$^{16}$;

R$^{13}$, R$^{13a}$, R$^{14}$, R$^{14a}$, and R$^{15}$ are independently selected at each occurrence from the group: H, =O, COOH, SO$_3$H, PO$_3$H, C$_1$–C$_5$ alkyl substituted with 0–3 R$^{16}$, aryl substituted with 0–3 R$^{16}$, benzyl substituted with 0–3 R$^{16}$, and C$_1$–C$_5$ alkoxy substituted with 0–3 R$^{16}$, NHC(=O)R$^{17}$, C(=O)NHR$^{17}$, NHC(=O)NHR$^{17}$, NHR$^{17}$, R$^{17}$, and a bond to the surfactant;

R$^{16}$ is independently selected at each occurrence from the group: a bond to the surfactant, COOR$^{17}$, C(=O)NHR$^{17}$, NHC(=O)R$^{17}$, OH, NHR$^{17}$, SO$_3$H, PO$_3$H, —OPO$_3$H$_2$, —OSO$_3$H, aryl substituted with 0–3 R$^{17}$, C$_{1-5}$ alkyl substituted with 0–1 R$^{18}$, C$_{1-5}$ alkoxy substituted with 0–1 R$^{18}$, and a 5–10 membered heterocyclic ring system containing 1–4 heteroatoms independently selected from N, S, and O and substituted with 0–3 R$^{17}$;

R$^{17}$ is independently selected at each occurrence from the group: H, alkyl substituted with 0–1 R$^{18}$, aryl substituted with 0–1 R$^{18}$, a 5–10 membered heterocyclic ring system containing 1–4 heteroatoms independently selected from N, S, and O and substituted with 0–1 R$^{18}$, C$_{3-10}$ cycloalkyl substituted with 0–1 R$^{18}$, polyalkylene glycol substituted with 0–1 R$^{18}$, carbohydrate substituted with 0–1 R$^{18}$, cyclodextrin substituted with 0–1 R$^{18}$, amino acid substituted with 0–1 R$^{18}$, polycarboxyalkyl substituted with 0–1 R$^{18}$, polyazaalkyl substituted with 0–1 R$^{18}$, peptide substituted with 0–1 R$^{18}$, wherein the peptide is comprised of 2–10 amino acids, 3,6-O-disulfo-B-D-galactopyranosyl, bis(phosphonomethyl)glycine, and a bond to the surfactant;

R$^{18}$ is a bond to the surfactant;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5; and x' is selected from 0, 1, 2, 3, 4, and 5.

(61) A diagnostic agent according to any one of embodiments 48–60 wherein

W$^{1}$ and W$^{2}$ are independently selected at each occurrence from the group: O, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, —(CH$_2$CH$_2$O)$_{76-84}$—, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–1 R$^{16}$, C$_{3-10}$ cycloalkyl substituted with 0–1 R$^{16}$, and a 5–10 membered heterocyclic ring system containing 1–4 heteroatoms independently selected from N, S, and O and substituted with 0–1 R$^{16}$;

R$^{13}$, R$^{13a}$, R$^{14}$, R$^{14a}$, and R$^{15}$ are independently selected at each occurrence from the group: H, =O, COOH, SO$_3$H, C$_1$–C$_5$ alkyl substituted with 0–1 R$^{16}$, aryl substituted with 0–1 R$^{16}$, benzyl substituted with 0–1 R$^{16}$, and C$_1$–C$_5$ alkoxy substituted with 0–1 R$^{16}$, NHC(=O)R$^{17}$, C(=O)NHR$^{17}$, NHC(=O)NHR$^{17}$, NHR$^{17}$, R$^{17}$, and a bond to the surfactant;

k is 0 or 1;

s is selected from 0, 1, 2, 3, 4, and 5;

s' is selected from 0, 1, 2, 3, 4, and 5;

s" is selected from 0, 1, 2, 3, 4, and 5; and t is selected from 0, 1, 2, 3, 4, and 5.

(62) A diagnostic agent according to embodiment 60 wherein:

W$^{1}$ is C(=O)NR$^{15}$;

h is 1;

g is 3;

R$^{13}$ and R$^{14}$ are independently H;

x is 1;

k is 0;

g' is 0;

h' is 1;

W$^{2}$ is NH; and x' is 1.

(63) A diagnostic agent according to embodiment 60 x is 0;

k is 1;

Z is aryl substituted with 0–3 R$^{16}$;

g' is 1;

W$^{2}$ is NH;

R$^{13a}$ and R$^{14a}$ are independently H;

h' is 1; and x' is 1.

(64) A diagnostic agent according to embodiment 60

W$^{1}$ is C(=O)NR$^{15}$;

h is 1;

g is 2;

R$^{13}$ and R$^{14}$ are independently H;

x is 1;

k is 0;

g' is 1;

R$^{13a}$ and R$^{14a}$ are independently H; or C1–5 alkyl substituted with 0–3 R$^{16}$;

R$^{16}$ is SO$_3$H;

W$^{2}$ is NHC(=O) or NH;

h' is 1; and x' is 2.

(65) A diagnostic agent according to embodiment 60

W$^{1}$ is C(=O)NH;

h is 1;

g is 3;

R$^{13}$ and R$^{14}$ are independently H;

k is 0;

g' is 0;
x is 1;
$W^2$ is —NH(C=O)— or —(OCH$_2$CH$_2$)$_{76-84}$—;
h' is 2; and
x' is 1.
(66) A diagnostic agent according to embodiment 60
x is 0;
k is 0;
g' is 3;
h' is 1;
$W^2$ is NH; and
x' is 1.
(67) A diagnostic agent according to embodiment 60
x is 0;
Z is aryl substituted with 0–3 $R^{16}$;
k is 1;
g' is 1;
$R^{13a}R^{14a}$ are independently H;
$W^2$ is NHC(=O) or —(OCH$_2$CH$_2$)$_{76-84}$—; and
x' is 1.
(68) A diagnostic agent according to embodiment 60
$W^1$ is C=O;
g is 2;
$R^{13}$ and $R^{14}$ are independently H;
k is 0;
g' is 0;
h' is 1;
$W^2$ is NH; and
x' is 1.
(69) A diagnostic agent according to embodiment 48 wherein the linking group is present.
(70) A diagnostic agent according to any one of embodiments 48–69 wherein
$S_f$ is a surfactant which is a lipid or a compound of the formula:

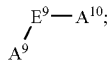

$A^9$ is selected from the group: OH and $OR^{32}$;
$A^{10}$ is $OR^{32}$;
$R^{32}$ is C(=O)C$_{1-20}$ alkyl;
$E^9$ is C$_{1-10}$ alkylene substituted with 1–3 $R^{33}$;
$R^{33}$ is independently selected at each occurrence from the group: $R^{35}$, —PO$_3$H—$R^{35}$, =O, —CO$_2$R$^{34}$, —C(=O) R$^{34}$, —C(=O)N(R$^{34}$)$_2$, —CH$_2$OR$^{34}$, —OR$^{34}$, —N(R$^{34}$)$_2$, C$_1$–C$_5$ alkyl, and C$_2$–C$_4$ alkenyl;
$R^{34}$ is independently selected at each occurrence from the group: $R^{35}$, H, C$_1$–C$_6$ alkyl, phenyl, benzyl, and trifluoromethyl;
$R^{35}$ is a bond to $L_n$;
and a pharmaceutically acceptable salt thereof.
(71) A diagnostic agent according to any one of embodiments 48–70 wherein the surfactant is a lipid or a compound of the formula:

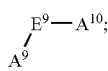

$A^9$ is $OR^{32}$;
$A^{10}$ is $OR^{32}$;
$R^{32}$ is C(=O)C$_{1-15}$ alkyl;
$E^9$ is C$_{1-4}$ alkylene substituted with 1–3 $R^{33}$;
$R^{33}$ is independently selected at each occurrence from the group: $R^{35}$, —PO$_3$H—$R^{35}$, =O, —CO$_2$R$^{34}$, —C(=O) R$^{34}$, —CH$_2$OR$^{34}$, —OR$^{34}$, and C$_1$–C$_5$ alkyl;

$R^{34}$ is independently selected at each occurrence from the group: $R^{35}$, H, C$_1$–C$_6$ alkyl, phenyl, and benzyl; and
$R^{35}$ is a bond to $L_n$.
(72) A diagnostic agent according to any one of embodiments 48–71, wherein

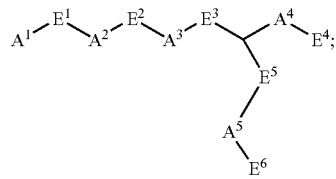

wherein:
$A^1$ ia a bond to Ln;
$E^1$ is C$_1$ alkyl substituted by $R^{23}$;
$A^2$ is NH;
$E^2$ is C$_2$ alkyl sunsttuted wth 0–1R$^{23}$;
$A^3$ is —O—P(O)(R$^{21}$)—O;
$E^3$ is C$_1$ alkyl;
$A^4$ and As are each —O—;
$E^4$ and $E^6$ are each independently C$_{1-16}$ alkyl substituted with 0–1R$^{23}$;
$E^5$ is C$_1$ alkyl;
$A^5$ is —O—;
$R^{21}$ is —OH; and
$R^{23}$ is =O.
(73) A diagnostic agent according to embodiment 48 wherein the compound is of the formula:

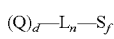

wherein, Q is a compound of Formulae (Ia) or (Ib):

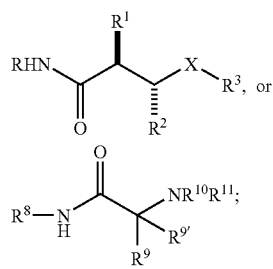

wherein,
R is independently OH or —CH$_2$SH;
$R^1$ is independently selected at each occurrence from the group: H, OH, C$_{1-3}$ alkyl, C$_{2-3}$ alkenyl, C$_{2-3}$ alkynyl, and heterocycle-S—CH$_2$—;
$R^2$ is independently C$_{1-20}$ alkyl;
X is independently C=O or SO$_2$, provided when X is C=O, $R^3$ is

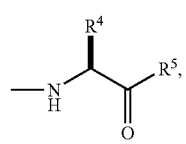

and when X is SO$_2$, $R^3$ is independently selected from the group: aryl substituted with 0–2 $R^6$, and heterocycle substituted with 0–2 $R^6$;
$R^4$ is independently selected at each occurrence from the group: C$_{1-6}$ alkyl, phenyl, and benzyl;
$R^5$ is independently at each occurrence from the group: NH(C$_{1-6}$ alkyl), NH-phenyl, and NH-heterocycle;

wherein said alkyl, phenyl and heterocycle groups are optionally substituted with a bond to $L_n$;

$R^6$ is independently aryloxy substituted with 0–3 $R^7$;

$R^7$ is independently halogen or methoxy;

or alternatively, $R^1$ and $R^4$ may be taken together to form a bridging group of the formula —(CH$_2$)$_3$—O-phenyl-CH$_2$—, optionally substituted with a bond to $L_n$;

or alternatively, $R^1$ and $R^2$ may be taken together to form a bridging group of the formula —(CH$_2$)$_3$—NH—, optionally substituted with a bond to $L_n$; or $R^1$ and $R^2$ taken together with the nitrogen and carbon atom through which they are attached form a $C_{5-7}$ atom saturated ring system substituted with one or more substituents selected from the group consisting of: a bond to Ln, a bond to Sf, and —C(=O)—NR$^{29}$R$^{30}$;

$R^8$ is independently at each occurrence OH or phenyl, optionally substituted with a bond to $L_n$, provided that when $R^8$ is phenyl, $R^{10}$ is —C(=O)—CR$^{12}$—NH—CH(CH$_3$)—COOH;

$R^9$ and $R^{9\prime}$ are independently H, $C_{1-6}$ alkyl optionally substituted with a bond to $L_n$, or are taken together with the carbon atom to which they are attached to form a 5–7 atom saturated, partially unsaturated or aromatic ring system containing 0–3 heteroatoms selected from O, N, SO$_2$ and S, said ring system substituted with $R^6$ and optionally substituted with a bond to $L_n$;

$R^{10}$ and $R^{11}$ are independently H, or $C_{1-6}$ alkyl optionally substituted with a bond to $L_n$, or are taken together with the nitrogen atom to which they are attached to form a 5–7 atom saturated, partially unsaturated or aromatic ring system containing 0–3 heteroatoms selected from O, N, SO$_2$ and S, said ring system optionally substituted with 0–3 $R^{27}$ or a bond to $L_n$;

or alternatively, $R^9$ and $R^{10}$ are taken together with the carbon atom to which they are attached to form a 5–7 atom saturated, partially unsaturated or aromatic ring system containing 0–3 heteroatoms selected from O, N, SO$_2$ and S, said ring system optionally substituted with a bond to $L_n$;

$R^{12}$ is independently $C_{1-20}$ alkyl;

d is selected from 1, 2, 3, 4, 5, 6, 7, 8, 9, and 10;

$L_n$ is a linking group having the formula:

$$((W^1)_h\!-\!(CR^{13}R^{14})_g)_x\!-\!(Z)_k\!-\!((CR^{13a}R^{14a})_{g'}\!-\!(W^2)_{h'})_{x'};$$

$W^1$ and $W^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–3 $R^{16}$, $C_{3-10}$ cycloalkyl substituted with 0–3 $R^{16}$, and a 5–10 membered heterocyclic ring system containing 1–4 heteroatoms independently selected from N, S, and O and substituted with 0–3 $R^{16}$;

$R^{13}$, $R^{13a}$, $R^{14}$, $R^{14a}$, and $R^{15}$ are independently selected at each occurrence from the group: H, =O, COOH, SO$_3$H, PO$_3$H, $C_1$–$C_5$ alkyl substituted with 0–3 $R^{16}$, aryl substituted with 0–3 $R^{16}$, benzyl substituted with 0–3 $R^{16}$, and $C_1$–$C_5$ alkoxy substituted with 0–3 $R^{16}$, NHC(=O)R$^{17}$, C(=O)NHR$^{17}$, NHC(=O)NHR$^{17}$, NHR$^{17}$, R$^{17}$, and a bond to Sf;

$R^{16}$ is independently selected at each occurrence from the group: a bond to Sf, COOR$^{17}$, C(=O)NHR$^{17}$, NHC(=O)

R$^{17}$, OH, NHR$^{17}$, SO$_3$H, PO$_3$H, —OPO$_3$H$_2$, —OSO$_3$H, aryl substituted with 0–3 R$^{17}$, $C_{1-5}$ alkyl substituted with 0–1 R$^{18}$, $C_{1-5}$ alkoxy substituted with 0–1 R$^{18}$, and a 5–10 membered heterocyclic ring system containing 1–4 heteroatoms independently selected from N, S, and O and substituted with 0–3 R$^{17}$;

$R^{17}$ is independently selected at each occurrence from the group: H, alkyl substituted with 0–1 R$^{18}$, aryl substituted with 0–1 R$^{18}$, a 5–10 membered heterocyclic ring system containing 1–4 heteroatoms independently selected from N, S, and O and substituted with 0–1 R$^{18}$, $C_{3-10}$ cycloalkyl substituted with 0–1 R$^{18}$, polyalkylene glycol substituted with 0–1 R$^{18}$, carbohydrate substituted with 0–1 R$^{18}$ cyclodextrin substituted with 0–1 R$^{18}$ amino acid substituted with 0–1 R$^{18}$, polycarboxyalkyl substituted with 0–1 R$^{18}$, polyazaalkyl substituted with 0–1 R$^{18}$, peptide substituted with 0–1 R$^{18}$, wherein the peptide is comprised of 2–10 amino acids, 3,6-O-disulfo-B-D-galactopyranosyl, bis(phosphonomethyl)glycine, and a bond to Sf;

$R^{18}$ is a bond to Sf;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from Q, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

$$\begin{array}{c} E^9\!-\!A^{10} \\ / \\ A^9 \end{array}$$

$A^9$ is selected from the group: OH and OR$^{32}$;

$A^{10}$ is OR$^{32}$;

$R^{32}$ is C(=O)C$_{1-20}$ alkyl;

$E^9$ is $C_{1-10}$ alkylene substituted with 1–3 R$^{33}$;

$R^{33}$ is independently selected at each occurrence from the group: R$^{35}$, —PO$_3$H—R$^{35}$, =O, —CO$_2$R$^{34}$, —C(=O)R$^{34}$, —C(=O)N(R$^{34}$)$_2$, —CH$_2$OR$^{34}$, —OR$^{34}$, —N(R$^{34}$)$_2$, $C_1$–$C_5$ alkyl, and $C_2$–$C_4$ alkenyl;

$R^{34}$ is independently selected at each occurrence from the group: R$^{35}$, H, $C_1$–$C_6$ alkyl, phenyl, benzyl, and trifluoromethyl;

$R^{35}$ is a bond to $L_n$; or

Sf is of the formula:

$$A^1\!-\!E^1\!-\!A^2\!-\!E^2\!-\!A^3\!-\!E^3\!-\!A^4\!-\!E^4;\ E^5\!-\!A^5\!-\!E^6$$

wherein:

$A^1$ ia a bond to Ln;

$E^1$ is $C_1$ alkyl substituted by R$^{23}$;

$A^2$ is NH;

$E^2$ is $C_2$ alkyl sunsttuted wth 0–1R$^{23}$;

$A^3$ is —O—P(O)(R$^{21}$)—O;

$E^3$ is $C_1$ alkyl;

$A^4$ and $A^5$ are each —O—;
$E^4$ and $E^6$ are each independently $C_{1-16}$ alkyl substituted with 0–1$R^{23}$;
$E^5$ is $C_1$ alkyl;
$A^5$ is —O—;
$R^{21}$ is —OH; and
$R^{23}$ is =O; or
a pharmaceutically acceptable salt thereof.

(74) A diagnostic agent according to embodiment 73, wherein:
R is —OH;
$R^2$ is C1–6 alkyl;
X is C=O;
$R^3$ is

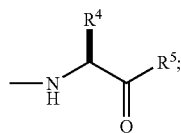

$R^1$ and $R^4$ are taken together to form a bridging group of formula —(CH$_2$)$_3$—O-phenyl-CH$_2$—;
$R^5$ is NH(C1–6alkyl), substituted with a bond to the linking group or a bond to the surfactant.

(75) A diagnostic agent according to any one of embodiments 73–74, wherein:
R is —OH;
$R^9$ is $C_1$ alkyl substituted with a bond to Ln;
$R^{10}$ and $R^{11}$ taken together with the nitrogen atom to which they are attached form a 5 atom saturated ring system, said right system is substituted with 0–3 $R^{27}$;
$R^{27}$ is =O, C1–4 alkyl, or phenyl substituted with $R^{28}$; and
$R^{28}$ is a phenoxy group substituted with 0–2 OCH$_3$ groups;
$S_f$ is a surfactant which is a lipid or a compound of the formula:

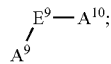

$A^9$ is $OR^{32}$;
$A^{10}$ is $OR^{32}$;
$R^{32}$ is C(=O)$C_{1-15}$ alkyl;
$E^9$ is $C_{1-4}$ alkylene substituted with 1–3 $R^{33}$;
$R^{33}$ is independently selected at each occurrence from the group: $R^{35}$, —PO$_3$H—$R^{35}$, =O, —CO$_2R^{34}$, —C(=O)$R^{34}$, —CH$_2$O$R^{34}$, —O$R^{34}$, and $C_1$–$C_5$ alkyl;
$R^{34}$ is independently selected at each occurrence from the group: $R^{35}$, H, $C_1$–$C_6$ alkyl, phenyl, and benzyl; and
$R^{35}$ is a bond to $L_n$.

(76) A diagnostic agent according to any one of embodiments 73–75, wherein:
R is —OH;
$R^9$ is $C_1$ alkyl substituted with a bond to Ln;
$R^{10}$ and $R^{11}$ taken together with the nitrogen atom to which they are attached form a 5 atom saturated ring system, said right system is substituted with 0–3 $R^{27}$;
$R^{27}$ is =O, C1–4 alkyl, or phenyl substituted with $R^{28}$; and
$R^{28}$ is a phenoxy group substituted with 0–2 OCH$_3$ groups;

$S_f$ is a surfactant which is a lipid or a compound of the of the formula:

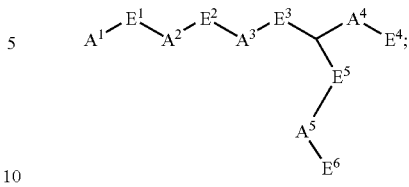

wherein:
$A^1$ ia a bond to Ln;
$E^1$ is $C_1$ alkyl substituted by $R^{23}$;
$A^2$ is NH;
$E^2$ is $C_2$ alkyl sunstituted wth 0–1$R^{23}$;
$A^3$ is —O—P(O)($R^{21}$)—O;
$E^3$ is $C_1$ alkyl;
$A^4$ and $A^5$ are each —O—;
$E^4$ and $E^6$ are each independently $C_{1-16}$ alkyl substituted with 0–1$R^{23}$;
$E^5$ is $C_1$ alkyl;
$A^5$ is —O—;
$R^{21}$ is —OH; and
$R^{23}$ is =O.

(77) A diagnostic agent according according to any one of embodiments 73–76, wherein:
wherein
R is —OH;
$R^1$ and $R^2$ taken together with the nitrogen and carbon atom through which they are attached form a $C_{5-7}$ atom saturated ring system substituted with one or more substituents selected from the group consisting of: a bond to Ln, a bond to Sf, and —C(=O)—NR$^{29}$R$^{30}$;
$R^{29}$ and $R^{30}$ taken together with the nitrogen atom through which they are attached form a C5–7 atom saturated ring system substituted with $R^{31}$; and
$R^{31}$ is a benzyloxy group substituted with C1–4 alkyl.
d is selected from 1, 2, 3, 4, and 5;
W is independently selected at each occurrence from the group: O, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_t$;
aa is independently at each occurrence an amino acid;
Z is selected from the group: aryl substituted with 0–1 $R^{16}$, $C_{3-10}$ cycloalkyl substituted with 0–1 $R^{16}$, and a 5–10 membered heterocyclic ring system containing 1–4 heteroatoms independently selected from N, S, and O and substituted with 0–1 $R^{16}$;
$R^{13}$, $R^{13a}$, $R^{14}$, $R^{14a}$, and $R^{15}$ are independently selected at each occurrence from the group: H, =O, COOH, SO$_3$H, $C_1$–$C_5$ alkyl substituted with 0–1 $R^{16}$, aryl substituted with 0–1 $R^{16}$, benzyl substituted with 0–1 $R^{16}$, and $C_1$–$C_5$ alkoxy substituted with 0–1 $R^{16}$, NHC(=O)$R^{17}$, C(=O)NHR$^{17}$, NHC(=O)NHR$^{17}$, NHR$^{17}$, $R^{17}$, and a bond to Sf;
k is 0 or 1;
s is selected from 0, 1, 2, 3, 4, and 5;
s' is selected from 0, 1, 2, 3, 4, and 5;
s" is selected from 0, 1, 2, 3, 4, and 5; and,
t is selected from 0, 1, 2, 3, 4, and 5.
(78) A diagnostic agent according to according to any one of embodiments 73–77, wherein:
$W^1$ is C(=O)NR$^{15}$;
h is 1;
g is 3;

$R^{13}$ and $R^{14}$ are independently H;
x is 1;
k is 0;
g' is 0;
h' is 1;
$W^2$ is NH; and
x' is 1.
(79) A diagnostic agent according to embodiment 73, wherein:
x is 0;
k is 1;
Z is aryl substituted with 0–3 $R^{16}$;
g' is 1;
$W^2$ is NH;
$R^{13a}$ and $R^{14a}$ are independently H;
h' is 1; and
x' is 1.
(80) A diagnostic agent according to Embodiment 73, wherein:
$W^1$ is C(=O)$NR^{15}$;
h is 1;
g is 2;
$R^{13}$ and $R^{14}$ are independently H;
x is 1;
k is 0;
g= is 1;
$R^{13a}$ and $R^{14a}$ are independently H; or C1–5 alkyl substituted with 0–3 $R^{16}$;
$R^{16}$ is $SO_3H$;
$W^2$ is NHC(=O) or NH;
h' is 1; and
x' is 2.
(81) A diagnostic agent according to Embodiment 73, wherein:
$W^1$ is C(=O)NH;
$W^2$ is —NH(C=O)— or —(OCH$_2$CH$_2$)$_{76-84}$—;
h' is 2; and
x' is 1.
(82) A diagnostic agent according to Embodiment 73, wherein:
x is 0;
k is 0;
g' is 3;
h' is 1;
$W^2$ is NH; and
x' is 1.
(83) A diagnostic agent according to Embodiment 73, wherein:
x is 0;
Z is aryl substituted with 0–3 $R^{16}$;
k is 1;
g' is 1;
$R^{13a}R^{14a}$ are independently H;
$W^2$ is NHC(=O) or —(OCH$_2$CH$_2$)$_{76-84}$—; and
x' is 1.
(84) A diagnostic agent according to Embodiment 73, wherein:
$W^1$ is C=O;
g is 2;
$R^{13}$ and $R^{14}$ are independently H;
k is 0;
g' is 0;
h' is 1;
$W^2$ is NH; and
x' is 1.
(85) A diagnostic agent according to Embodiment 1, wherein the compound is selected from the group consisting of:

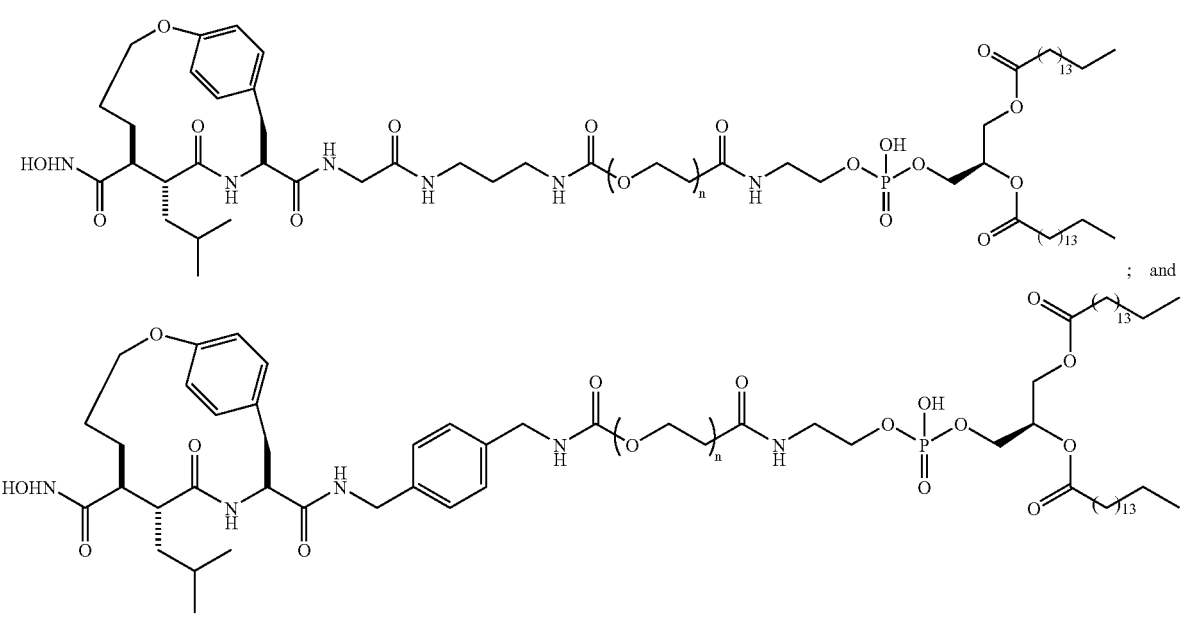

; and h is 1;
g is 3;
$R^{13}$ and $R^{14}$ are independently H;
k is 0;
g= is 0;
x is 1;

(86) A diagnostic agent according to embodiment 48, wherein: wherein the echogenic gas is a perfluorocarbon gas or sulfur hexafluoride.
(87) A diagnostic agent according to embodiment 86 wherein said perfluorocarbon is selected from the group consisting of perfluoromethane, perfluoroethane, perfluoropropane, perfluorobutane, perfluorocyclobutane, perfluoropentane, and perfluorohexane.

(88) A diagnostic composition comprising a compound according to embodiment 48 or a pharmaceutically acceptable salt thereof, and a pharmaceutically acceptable carrier.

(89) A diagnostic composition comprising a compound according to embodiment 48 or a pharmaceutically acceptable salt form thereof, an echogenic gas and a pharmaceutically acceptable carrier.

(90) A diagnostic composition comprising a compound according to embodiment 48 further comprising: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

(91) A method of detecting, imaging or monitoring the presence of matrix metalloproteinase in a patient comprising the steps of:
  a) administering to said patient a diagnostic agent of embodiment 1; and
  b) acquiring an image of a site of concentration of said diagnostic agent in the patient by a diagnostic imaging technique.

(92) A method of detecting, imaging or monitoring the presence of matrix metalloproteinase in a patient comprising the steps of:
  a) administering to said patient a diagnostic agent of embodiment 48; and
  b) acquiring an image of a site of concentration of said diagnostic agent in the patient by a diagnostic imaging technique.

(93) A method of detecting, imaging or monitoring a pathological disorder associated with matrix metalloproteinase activity in a patient comprising the steps of:
  a) administering to said patient a diagnostic agent of embodiment 1; and
  b) acquiring an image of a site of concentration of said diagnostic agent in the patient by a diagnostic imaging technique.

(94) A method of detecting, imaging or monitoring a pathological disorder associated with matrix metalloproteinase activity in a patient comprising the steps of:
  a) administering to said patient a diagnostic agent according to embodiment 48; and
  b) acquiring an image of a site of concentration of said diagnostic agent in the patient by a diagnostic imaging technique.

(95) A method of detecting, imaging or monitoring atherosclerosis in a patient comprising the steps of:
  a) administering a diagnostic agent according to embodiment 1; and
  b) acquiring an image of a site of concentration of said diagnostic agent in the body by a diagnostic imaging technique.

(96) A method of detecting, imaging or monitoring atherosclerosis in a patient comprising the steps of:
  a) administering a diagnostic agent according to embodiment 48; and
  b) acquiring an image of a site of concentration of said diagnostic agent in the body by a diagnostic imaging technique.

(97) A method according to embodiment 95, wherein the atherosclerosis is coronory atherosclerosis or cerebrovascular atherosclerosis.

(98) A method according to embodiment 96, wherein the atherosclerosis is coronory atherosclerosis or cerebrovascular atherosclerosis.

(99) A method of identifying a patient at high risk for transient ischemic attacks or stroke by determining the degree of active atherosclerosis in a patient comprising carrying out the method of embodiment 96.

(100) A method of identifying a patient at high risk for transient ischemic attacks or stroke by determining the degree of active atherosclerosis in a patient comprising carrying out the method of embodiment 97.

(101) A method of identifying a patient at high risk for acute cardiac ischemia, myocardial infarction or cardiac death by determining the degree of active atherosclerosis by imaging the patient by the method of embodiment 96.

(102) A method of identifying a patient at high risk for acute cardiac ischemia, myocardial infarction or cardiac death by determining the degree of active atherosclerosis by imaging the patient by the method of embodiment 97.

(103) A method of simultaneous imaging of cardiac perfusion and extracellular matrix degradation in a patient comprising the steps of:
  a) administering a diagnostic agent according to embodiment 1, wherein the diagnostic metal is a gamma-emitting radioisotope; and
  (b) administering a cardiac perfusion compound, wherein the compound is radiolabeled with a gamma-emitting radioisotope which exhibits a gamma emission energy that is spectrally separable from the gamma emission energy of the diagnostic metal conjugated to the targeting moiety in step (a); and
  (c) acquiring, by a diagnostic imaging technique, simultaneous images of the sites of concentration of the spectrally separable gamma-emission energies of the compounds administered in steps (a) and (b).

The present invention may be embodied in other specific forms without departing from the spirit or essential attributes thereof.

Definitions

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

The term "metallopharmaceutical" means a pharmaceutical comprising a metal. The metal is the cause of the imageable signal in diagnostic applications and the source of the cytotoxic radiation in radiotherapeutic applications. Radiopharmaceuticals are metallopharmaceuticals in which the metal is a radioisotope.

By "reagent" is meant a compound of this invention capable of direct transformation into a metallopharmaceutical of this invention. Reagents may be utilized directly for the preparation of the metallopharmaceuticals of this invention or may be a component in a kit of this invention.

The term "inhibitor" means a compound of this invention that inhibits the function of a matrix metalloproteinase.

By "stable compound" or "stable structure" is meant herein a compound that is sufficiently robust to survive isolation to a useful degree of purity from a reaction mixture, and formulation into an efficacious pharmaceutical agent.

The term "substituted", as used herein, means that one or more hydrogens on the designated atom or group is replaced with a selection from the indicated groups provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla., 1984, as any substance which yields ions, other than hydrogen or hydroxyl ions. As used herein, "pharmaceutically acceptable salts" refer to derivatives of the disclosed compounds modified by making acid or base salts. Examples of pharmaceutically acceptable salts include, but are not limited to, mineral or organic acid salts of basic residues such as amines; alkali or organic salts of acidic residues such as carboxylic acids; and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfamic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, hexyl, heptyl, octyl, nonyl, and decyl; "cycloalkyl" or "carbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" or "bicyclic" is intended to include saturated bicyclic ring groups such as [3.3.0]bicyclooctane, [4.3.0]bicyclononane, [4.4.0]bicyclodecane (decalin), [2.2.2]bicyclooctane, and so forth. As used herein, the term "alkene" or "alkenyl" is intended to include hydrocarbon chains having the specified number of carbon atoms of either a straight or branched configuration and; one or more unsaturated carbon-carbon bonds which may occur in any stable point along the chain, such as ethenyl, propenyl, and the like.

As used herein, the term "alkyne" or "alkynyl" is intended to include hydrocarbon chains having the specified number of carbon atoms of either a straight or branched configuration and one or more unsaturated carbon-carbon triple bonds which may occur in any stable point along the chain, such as propargyl and the like.

As used herein, "aryl" or "aromatic residue" is intended to mean phenyl or naphthyl, which when substituted, the substitution can be at any position.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms: in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl" means an aryl group bearing an alkyl group of 1–10 carbon atoms bearing an aryl group; and the term "heterocycloalkyl" means an alkyl group of 1–10 carbon atoms bearing a heterocycle.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to,
α-cyclodextrin, hydroxyethyl-α-cyclodextrin, hydroxypropyl-α-cyclodextrin, β-cyclodextrin, hydroxypropyl-β-cyclodextrin, carboxymethyl-β-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-α-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

X-ray contrast agent pharmaceuticals, ultrasound contrast agent pharmaceuticals and metallopharmaceuticals for magnetic resonance imaging contrast are provided to the end user in their final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to synthesize a radiopharmaceutical.

The following abbreviations are used herein:

| Acm | acetamidomethyl |
| b-Ala, beta-Ala or bAla | 3-aminopropionic acid |
| ATA | 2-aminothiazole-5-acetic acid or 2-aminothiazole-5-acetyl group |
| Boc | t-butyloxycarbonyl |
| CBZ, Cbz or Z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| hynic | boc-hydrazinonicotinyl group or 2-[[[5-[carbonyl]-2-pyridinyl]hydrazono]methyl]-benzenesulfonic acid, |
| NMeArg or MeArg | a-N-methyl arginine |
| NMeAsp | a-N-methyl aspartic acid |
| NMM | N-methylmorpholine |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Nle=norleucine
Orn=ornithine
Phe=phenylalanine
Phg=phenylglycine
Pro=proline
Sar=sarcosine
Ser=serine
Thr=threonine
Trp=tryptophan
Tyr=tyrosine
Val=valine The ultrasound contrast agents of the present invention comprise a plurality of matrix metalloproteinase inhibiting moieties attached to or incorporated into a microbubble of a biocompatible gas, a liquid carrier, and a surfactant microsphere, further comprising an optional linking moiety, $L_n$, between the targeting moieties and the microbubble. In this context, the term liquid carrier means aqueous solution and the, term surfactant means any amphiphilic material which produces a reduction in interfacial tension in a solution. A list of suitable surfactants for forming surfactant microspheres is disclosed in EP0727225A2, herein incorporated by reference. The term surfactant microsphere includes nanospheres, liposomes, vesicles and the like. The biocompatible gas can be air, or a fluorocarbon, such as a $C_3$–$C_5$ perfluoroalkane, which provides the difference in echogenicity and thus the contrast in ultrasound imaging. The gas is encapsulated or contained in the microsphere to which is attached the biodirecting group, optionally via a linking group. The attachment can be covalent, ionic or by van der Waals forces. Specific examples of such contrast agents include lipid encapsulated perflubrocarbons, with a plurality of MMP inhibiting compounds.

X-ray contrast agents of the present invention are comprised of one or more matrix metalloproteinase inhibiting targeting moieties attached to one or more X-ray absorbing or "heavy" atoms of atomic number 20 or greater, further comprising an optional linking moiety, $L_n$, between the targeting moieties and the X-ray absorbing atoms. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215).

MRI contrast agents of the present invention are comprised of one or more matrix metalloproteinase inhibiting targeting moieties attached to one or more paramagnetic metal ions, further comprising an optional linking moiety, $L_n$, between the targeting moieties and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. Nos. 5,801,228, 5,567,411, and 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

Matrix metalloproteinases (MMPs) are a family of structurally related zinc-containing enzymes that mediate the integrity of extracellular matrix (Whittaker, M. et al, Chem. Rev., 1999, 99, 2735–2776). They are excreted by a variety of connective tissue and pro-inflammatory cells, such as, fibroblasts, osteoblasts, macrophages, neutrophils, lymphocytes and endothelial cells. There is now a body of evidence that matrix metalloproteinases (MMPs) are important in the uncontrolled breakdown of connective tissue, including proteoglycan and collagen, leading to resorption of the extracellular matrix. This is a feature of a number of cardiovascular pathological conditions, such as atherosclerosis, heart failure, restenosis and reperfusion injury. Normally these catabolic enzymes are tightly regulated at the level of their synthesis, as well as, at their level of extracellular activity through the action of specific inhibitors, such as alpha-2-macroglobulins and TIMP (tissue inhibitor of metalloproteinase), which form inactive complexes with the MMPs. Therefore, extracellular matrix degradation and remodeling are regulated by the relative expression of TIMPs and MMPs. The MMPs are classified into several families based on their domain structure: matrilysin (minimal domain, MMP-7), collagenase (hemopexin domain, MMP-1, MMP-8, MMP-13), gelatinase (fibronectin domain, MMP-2, MMP-9), stromelysin (hemopexin domain, MMP-3, MMP-10, MMP-11), metalloelastase (MMP-12). In addition, the transmembrane domain family (MT-MMPs) has been recently discovered and comprises MMP-14 through MMP-17.

MMP proteolytic activity and extracellular matrix degradation is dependent on the comparative balance between MMPs and TIMPs. TIMPs and synthetic small molecules or matrix metalloproteinase inhibitors have therapeutic potential for diseases involving elevated levels of MMP activity (Whittaker, M. et al, Chem. Rev., 1999, 99, 2735–2776; Babine, R. E. et al, Chem., Rev., 1997, 97, 1359; De, B. et al, Ann. N.Y. Acad. Sci., 1999, 878, 40–60; Summers, J. B. et al, Annual Reports in Med. Chem., 1998, 33, 131).

A functional group, such as —CONH—OH, —COOH, or —SH, is necessary for a molecule to be an effective inhibitor of MMPs. This functional group is involved in the chelation of the active site zinc ion, and is commonly referred to as the zinc binding group or ZBG. The hydroxamate, for example, is a bidentate ligand for zinc.

The pharmaceuticals of the present invention have the formulae, $(Q)_d\text{—}L_n\text{—}(C_h\text{—}X)$, $(Q)_d\text{—}L_n\text{—}(C_h\text{—}X^1)_{d'}$, $(Q)_d\text{—}L_n\text{—}(X^2)_{d''}$, and $(Q)_d\text{—}L_n\text{—}(X^3)$, wherein Q represents a compound that inhibits a matrix metalloproteinase, d is 1–10, d'=1–100, $L_n$ represents an optional linking group, $C_h$ represents a metal chelator or bonding moiety, X represents a radioisotope, $X^1$ represents paramagnetic metal ion, $X^2$ represents a paramagnetic metal ion or heavy atom containing insoluble solid particle, d" is 1–100, and $X^3$ represents a surfactant microsphere of an echogenic gas.

One class of compounds of the present invention is comprised of one or more inhibitors, Q, which are succinyl hydroxamates. A generic structure of succinyl hydroxamate is shown below (1).

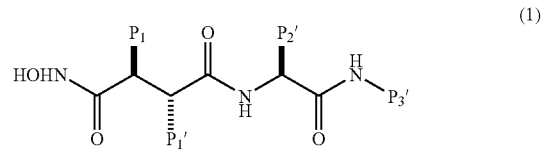

(1)

The ethylene spacer between the ZBG (—CONH—OH) and the succinyl amide is essential for potent activity. Substitution at $P_1$ tends to confer broad-spectrum activity on the MMPIs. Substituents at this position, in general, tend to point away from the enzyme. Moieties capable of hydrogen bonding and lipophilic substituents at the $P_1$ position α to the hydroxamate (Johnson, W. H. et al, J. Enz. Inhib., 1987, 2, 1) tend to enhance activity (2). Incorporation of a hydroxyl group (Beckett, P. R., et al, Drug, Discovery Today, 1996, 1, 16) at that position improves oral activity in some case (3).

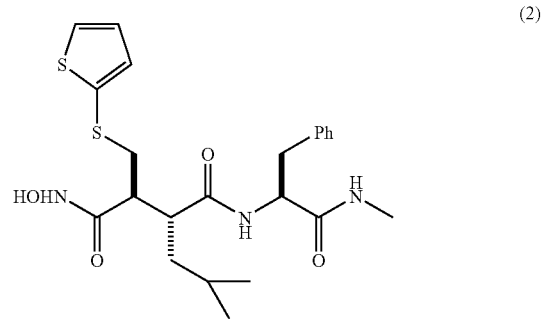

(2)

(3)

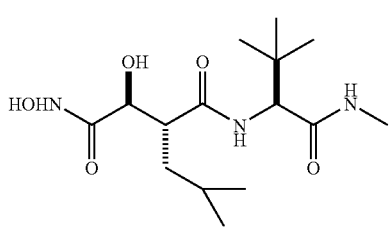

Substituents at the P$_1$'position on the succinyl hydroxamates tend to impart selectivity to the MMPIs. The S$_1$' pocket is deep for MMP-2, MMP-3, MMP-8 and MMP-9 and occluded (short) for MMP-1 and MMP-7. A long alkyl substituent at the P$_1$' position, for example, imparts selectivity (Miller, A. et al, Bioorg. Med. Chem. Lett., 1997, 7, 193) for MMP-2 over MMP-1 and MMP-3 (4 and 5).

(4)

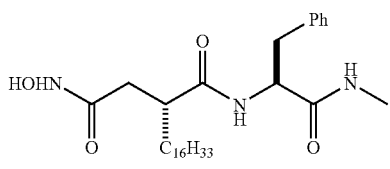

(5)

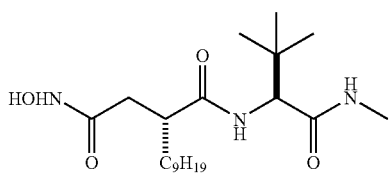

Substituents at the P$_2$' position also point away from the enzyme. The P$_1$ and the P$_2$' positions can be linked (Xue, C-B. et al, J. Med. Chem., 1998, 41, 1745; Steinman, D. H. et al, Bioorg. Med. Chem. Lett., 1998, 8, 2087) to form a macrocycle (6). Compounds such as (6) also exhibit nanomolar activity.

(6)

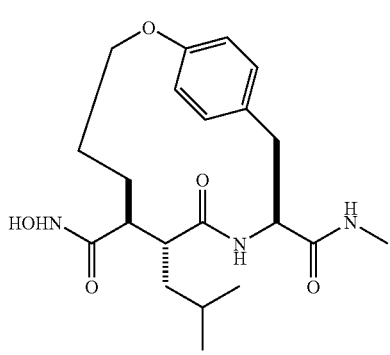

The nature of the macrocycle also imparts some selective inhibition among the MMPs. The P$_2$' and the P$_3$' positions may be cyclized to form lactams. The size of the lactam governs the selectivity.

The P$_3$' position is a relatively open area in the succinyl hydroxamates, and a wide range of substitutents (for example (7)) may be introduced (Sheppard, G. S. et al, Bioorg. Med. Chem. Lett., 1998, 8, 3251) at this position. This position also offers the flexibility of attaching the optional linker, L$_n$, the chelator(s0, C$_n$, for the imageable moieties X and X$^1$, and the imageable moieties, X$^2$ and X$^3$.

(7)

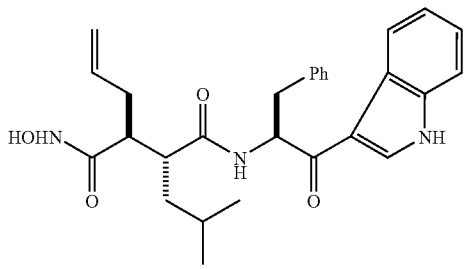

Other succinyl hydroxamates with modified P$_2$' and P$_3$' positions, such as (8) also have shown potent inhibition of MMPs. Those compounds and syntheses of them are further described in the following patent applications which are hereby incorporated by reference into this patent application: U.S. patent application Ser. Nos. 09/165,747, 08/743,439, 09/134,484, 09/247,675, 09/335,086, 09/312,066, 09/311,168, 60/127,594, and 60/127,635.

(8)

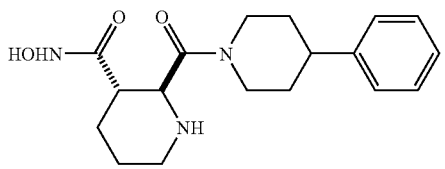

Another class of compounds of the present invention is comprised of one or more inhibitors, Q, which are sulfonamide hydroxamates, such as (9) and (10). Modification of the isopropyl substituent in (10) results in deep pocket MMP selectivity, for example MMP-2 vs MMP-1 (Santos, O. et al., J. Clin. Exp. Metastasis, 1997,15, 499; MacPherson, L. J. et al, J. Med. Chem., 1997, 40, 2525).

(9)

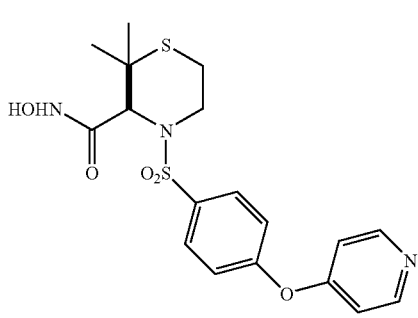

(10)

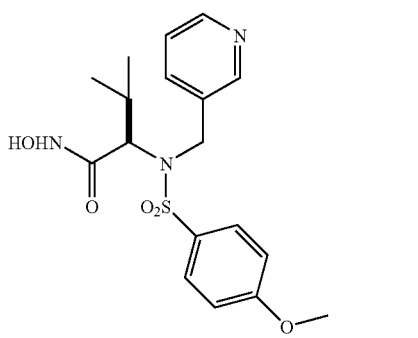

Additional examples of inhibitors, Q, include the derivatized 'alanine' hydroxamates, such as compounds (11) and (12), which show selectivity for MMP-2 and MMP-9 over the other MMPs. Those compounds and syntheses of them are further described in the following patent applications which are hereby incorporated by reference into this patent application: U.S. patent application Ser. Nos. 09/165,747, 08/743,439, 09/134,484, 09/247,675, 09/335,086, 09/312,066, 09/311,168, 60/127,594, and 60/127,635.

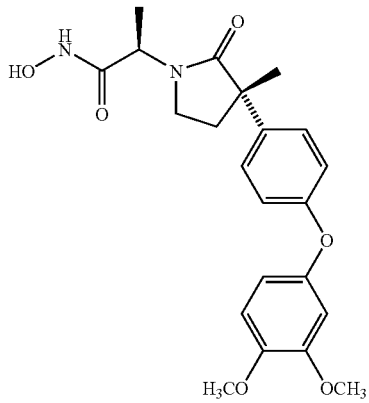
(11)

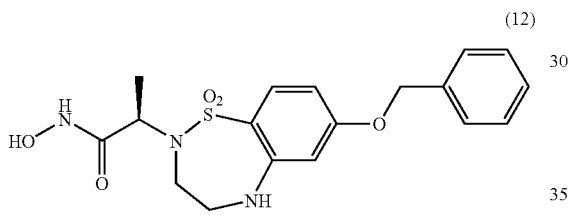
(12)

compound (13), which shows selectivity for MMP-2 and MMP-9, and in which the alpha position has a quaternary carbon and the molecule does not contain any stereo centers (Lovejoy, B. et al., Nature Struct. Biol., 1999, 6, 217);

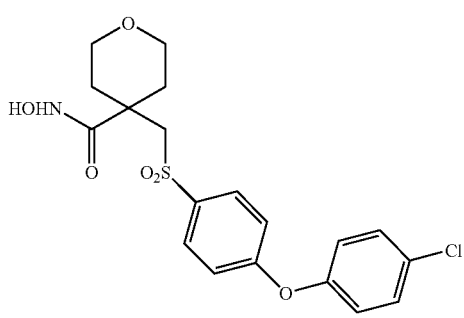
(13)

compound (14), which uses a carboxylic acid as the ZBG, and exhibits significant selectivity for MMP-2 (vs MMP-1), when X=butyl vs X=H (Sahoo, S. P. et al, Bioorg. Med. Chem. Lett., 1995, 5, 2441); and

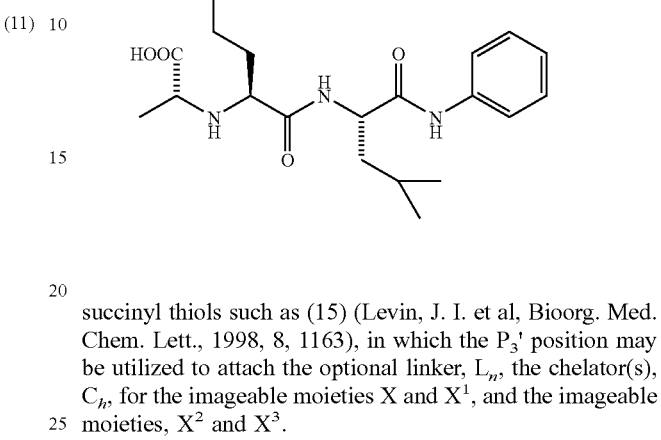
(14)

succinyl thiols such as (15) (Levin, J. I. et al, Bioorg. Med. Chem. Lett., 1998, 8, 1163), in which the $P_3'$ position may be utilized to attach the optional linker, $L_n$, the chelator(s), $C_h$, for the imageable moieties X and $X^1$, and the imageable moieties, $X^2$ and $X^3$.

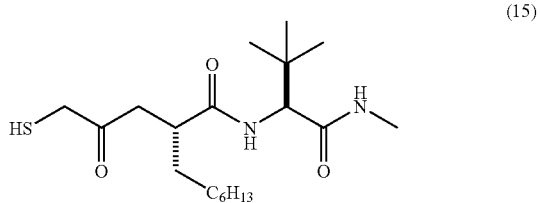
(15)

Preferred pharmaceuticals of the present invention are comprised of inhibitors, Q, which exhibit selectivity for MMP-1, MMP-2, MMP-3, MMP-9, or MMP-14 alone or in combination over the other MMPs. Examples of preferred moieties, Q, include compounds 4, 5, 6, 8, 9, 10, 11, 12, and 13.

Most preferred are comprised of inhibitors, Q, which exhibit selectivity for MMP-2, MMP-9, or MMP-14 alone or in combination over the other MMPs. Examples of the most preferred moieties, Q, include compounds 6, 8, 11, and 12.

The pharmaceuticals of the present invention can be synthesized by several approaches. One approach involves the synthesis of the targeting MMP inhibiting moiety, Q, and direct attachment of one or more moieties, Q, to one or more metal chelators or bonding moieties, $C_h$, or to a paramagnetic metal ion or heavy atom containing solid particle, or to an echogenic gas microbubble. Another approach involves the attachment of one or more moieties, Q, to the linking group, $L_n$, which is then attached to one or more metal chelators or bonding moieties, $C_h$, or to a paramagnetic metal ion or heavy atom containing solid particle, or to an echogenic gas microbubble. Another approach, useful in the synthesis of pharmaceuticals wherein d is 1, involves the synthesis of the moiety, Q—$L_n$, together, by incorporating residue bearing $L_n$ into the synthesis of, the MMP inhibitor, Q. The resulting moiety, Q—$L_n$, is then attached to one or more metal chelators or bonding moieties, $C_h$, or to a paramagnetic metal ion or heavy atom containing solid particle, or to an echogenic gas microbubble. Another approach involves the synthesis of an inhibitor, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The MMP inhibiting moieties, Q, optionally bearing a linking group, $L_n$, or a fragment of the linking group, can be synthesized using standard synthetic methods known to those skilled in the art. Preferred methods include but are not limited to those methods described below.

Generally, peptides, polypeptides and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The peptides, polypeptides and peptidomimetics may also be synthesized using automated synthesizing equipment. In addition to the foregoing, procedures for peptide, polypeptide and peptidomimetic synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide, polypeptide or peptidomimetic, two peptide, polypeptide or peptidomimetic fragments, or the cyclization of a peptide, polypeptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids or amino acid mimetics must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) J. Org. Chem. 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasudcinoyl. The preferred alpha-amino protecting group is either Boc or Fmoc. Many amino acid or amino acid mimetic derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids or amino acid mimetics bearing side chain functionalities must be protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide, polypeptide or peptidomimetic. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable.

For instance, Boc can be used for lysine, tert-butyl ether for serine, threonine and tyrosine, and tert-butyl ester for glutamic and aspartic acids.

Once the elongation of the peptide, polypeptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free a-carboxylate and a free a-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide-vor peptidomimetic (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated herein by reference.

The attachment of linking groups, $L_n$, to the MMP inhibitors, Q; chelators or bonding units, $C_h$, to the inhibitors, Q, or to the linking groups, $L_n$; and inhibitors bearing a fragment of the linking group to the remainder of the linking group, in combination forming the moiety, $(Q)_d$—$L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3(1), which is incorporated herein by reference.

A number of methods can be used to attach the MMP inhibitors, Q, to paramagnetic metal ion or heavy atom containing solid particles, $X^2$, by one of skill in the art of the surface modification of solid particles. In general, the targeting moiety Q or the combination $(Q)_d L_n$ is attached to a coupling group that react with a constituent of the surface of the solid particle. The coupling groups can be any of a number of silanes which react with surface hydroxyl-groups on the solid particle surface, as described in co-pending U.S. patent application Ser. No. 09/356,178 and can also include polyphosphonates, polycarboxylates, polyphosphates or mixtures thereof which couple with the surface of the solid particles, as described in U.S. Pat. No. 5,520,904.

A number of reaction schemes-can be used to attach the MMP inhibitors, Q, to the, surfactant microsphere, $X^3$. These are illustrated in following reaction schemes where $S_f$ represents a surfactant moiety that forms the surfactant microsphere.

Acylation Reaction:

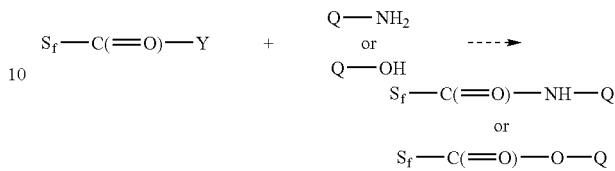

Y is a leaving group or active ester

Disulfide Coupling:

Sulfonamide Coupling:

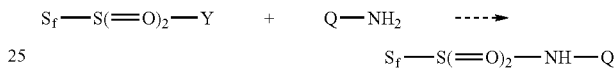

Reductive Amidation:

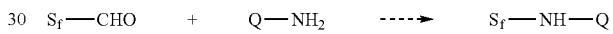

In these reaction schemes, the substituents $S_f$ and Q can be reversed as well.

The linking group $L_n$ can serve several roles. First it provides a spacing group between the metal chelator or bonding moiety, $C_h$, the paramagnetic metal ion or heavy atom containing solid particle, $X^2$, and the surfactant microsphere, $X^3$, and the one or more of the MMP inhibitors, Q, so as to minimize the possibility that the moieties $C_h$—X, $C_h$—$X^1$, $X^2$, and $X^3$, will interfere with the interaction of the recognition sequences of Q with MMPs associated with cardiovascular pathologies. The necessity of incorporating a linking group in a reagent is dependent on the identity of Q, $C_h$—X, $C_h$—$X^1$, $X^2$, and $X^3$. If $C_h$—X, $C_h$—$X^1$, $X^2$, and $X^3$, cannot be attached to Q without substantially diminishing its ability to inhibit MMPs, then a linking group is used. A linking group also provides a means of independently attaching multiple inhibitors, Q, to one group that is attached to $C_h$—X, $C_h$—$X^1$, $X^2$, or $X^3$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, Q, with the MMPs expressed in the cardiovascular pathologies. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

The metal chelator or bonding moiety, $C_h$, is selected to form stable complexes with the metal ion chosen for the particular application. Chelators or bonding moieties for diagnostic radiopharmaceuticals are selected to form stable complexes with the radioisotopes that have imageable gamma ray or positron emissions, such as $^{99m}$Tc, $^{95}$Tc, $^{111}$In, $^{62}$Cu, $^{62}$Cu, $^{64}$Cu, $^{67}$Ga, $^{68}$Ga, $^{86}$Y.

Chelators for technetium, copper and gallium isotopes are selected from diaminedithiols, monoamine-monoamidedithiols, triamide-monothiols, monoamine-diamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for $^{111}$In and $^{86}$Y are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine. Procedures for synthesizing these chelators that are not commercially available can be found in Brechbiel, M. and Gansow, O., *J. Chem. Soc. Perkin Trans.* 1992, 1, 1175; Brechbiel, M. and Gansow, O., *Bioconjugate Chem.* 1991, 2, 187; Deshpande, S., et. al., *J. Nucl. Med.* 1990, 31, 473; Kruper, J., U.S. Pat. No. 5,064,956, and Toner, J., U.S. Pat. No. 4,859,777, the disclosures of which are hereby incorporated by reference in their entirety.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals the ability to administer said ancillary or co-ligand to a patient without adverse physiological consequences to said patient, and, the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and, amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The most preferred technetium radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen (sp² hybridized), sulfur (sp² hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. Nos. 08/415,908, and 60/013360 and 08/646,886, the disclosures of which are herein incorporated by reference; in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur (sp² hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

Chelators for magnetic resonance imaging contrast agents are selected to form stable complexes with paramagnetic metal ions, such as Gd(III), Dy(III), Fe(III), and Mn(II), are selected from cyclic, and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

There are three key features of the pharmaceuticals of the present invention that determine their efficacy: MMP selectivity, inhibitory potency, typically expressed as the Ki value, and the rate of clearance from the blood. Preferred pharmaceuticals of the present invention are comprised of inhibitors, Q, which exhibit selectivity for MMP-1, MMP-2, MMP-3, MMP-9, or MMP-14 alone or in combination over the other MMPs. Most preferred are comprised of inhibitors, Q, which exhibit selectivity for MMP-2, MMP-9, or MMP-14 alone or in combination over the other MMPs. Ki values for the preferred pharmaceuticals of the present invention are <100 nM for one or more of MMP-1, MMP-2, MMP-3, MMP-9, or MMP-14. Ki values for the most preferred pharmaceuticals of the present invention are <10 nM for one or more of MMP-2, MMP-9, or MMP-14.

The rate of clearance from the blood is of particular importance for cardiac imaging procedures, since the cardiac blood pool is large compared to the disease foci that one desires to image. For an effective cardiac imaging agent, the target to background ratios (disease foci-to-blood and disease foci-to-muscle) need to be greater or equal to 1.5, preferably greater or equal to 2.0, and more preferably even greater. Preferred pharmaceuticals of the present invention have blood clearance rates that result in <10% i.d./g at 2 hours post-injection, measured in a mouse model, or <0.5% i.d./g at 2 hours post-injection, measured in a dog model. Most preferred pharmaceuticals of the present invention have blood clearance rates that result in <3% i.d./g at 2 hours post-injection, measured in a mouse model, or <0.05% i.d./g at 2 hours post-injection, measured in a dog model.

The technetium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at, temperatures from 0 to 100° C. The technetium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator-or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form intermediate radionuclide complex, and then adding an ancillary ligand $A_{L2}$ and reacting further at temperatures from 0 to 100° C.

The technetium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of the present invention used to prepare the technetium radiopharmaceuticals of the present invention can range from 0.01 µg to 10 mg, or more preferably from 0.5 µg to 200 µg. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg. The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

In another embodiment of the current invention, a scintigraphic image of a radiolabeled MMPI compound would be acquired at the same time as a scintigraphic image of a radiolabeled cardiac perfusion imaging agent. This simultaneous dual isotope imaging would be done by utilizing radioisotopes of the MMPI and perfusion imaging agents which had spectrally separable gamma emission energies. For example, a Tc99m cardiac perfusion imaging agent (such as Tc99m-Sestamibi) or Tl201 (as Thallous Chloride), and an In111-labeled MMPI compound would be imaged simultaneously with a standard gamma camera. This is possible because the Tc99m gamma energy of ~140 KeV or the Tl201 gamma energy of ~80 KeV are easily separable from the In111 gamma energies of ~160 KeV and 250 KeV. This simultaneous imaging of cardiac perfusion and extracellular matrix degradation (as evidenced by MMPI compound localization) is extremely useful for improved anatomic assessment of the location of MMPI compound distribution in the heart based on the comparison to the perfusion distribution seen on the Tc99m-Sestamibi or Tl201 image. In addition, the simultaneous imaging of perfusion and extracellular matrix degradation allows a more complete assessment of the underlying cardiac disease, both in terms of blood flow alterations and biochemical changes, in a single imaging session on a patient.

The simultaneous dual-isotope imaging of cardiac perfusion and extracellular matrix degradation allows the localization of sites of vulnerable plaque and cardiac perfusion to be visualized during one imaging session. In addition, the simultaneous imaging of tissue changes associated with congestive heart failure (from the MMPI imaging agent) and coronary artery disease (from the perfusion imaging agent) is extremely useful in characterizing the underlying causes of CHF.

The simultaneous imaging of different radioisotopically-labeled radiopharmaceuticals in patients has been reported. For example, Antunes, et al., Am J. Cardiol. 1992; 70: 426–431, have demonstrated that it is possible to image myocardial infarction with an In111-antimyosin antibody along with the imaging of cardiac perfusion with Tl201. However, the dual isotope imaging of the present invention is new, because it is the first reported approach to the simultaneous, dual-isotope imaging of a radiolabeled MMPI compound and a cardiac perfusion imaging compound. The combination of MMPI scintigraphic imaging with perfusion imaging provides the imaging physician with an extraordinary amount of clinical information regarding ischemic coronary artery disease or congestive heart failure in one imaging session.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 µg/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary, ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The indium, copper, gallium, and yttrium radiopharmaceuticals of the present invention can be easily prepared by admixing a salt of a radionuclide and a reagent of the present invention, in an aqueous solution at temperatures from 0 to 100° C. These radionuclides are typically obtained as a dilute aqueous solution in a mineral acid, such as hydrochloric, nitric or sulfuric acid. The radionuclides are combined with from one to about one thousand equivalents of the reagents of the present invention dissolved in aqueous solution. A buffer is typically used to maintain the pH of the reaction mixture between 3 and 10.

The gadolinium, dysprosium, iron and manganese metallopharmaceuticals of the present invention can be easily prepared by admixing a salt of the paramagnetic metal ion and a reagent of the present invention, in an aqueous solution at temperatures from 0 to 100° C. These paramagnetic metal ions are typically obtained as a dilute aqueous solution in a mineral acid, such as hydrochloric, nitric or sulfuric acid. The paramagnetic metal ions are combined with from one to about one: thousand equivalents of the reagents of the present invention, dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of metallopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of metallopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of metallopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(Qxypropylene)poly(oxyethylene) block copolymers (Pluronics) and lecithin. Preferred solubilizing aids are polyethylene glycol, and Pluronics.

Bacteriostats useful in the preparation of metallopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The magnetic resonance imaging contrast agents of the present invention may be used in a similar manner as other MRI agents as described in U.S. Pat. Nos. 5,155,215; 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2. mmol/kg. Imaging is performed using known techniques, preferably X-ray,computed tomography.

The ultrasound contrast agents of the present invention are administered by intravenous injection in an amount of 10 to 30 μL of the echogenic gas per kg body weight or by infusion at a rate of approximately 3 μL/kg/min. Imaging is performed using known techniques of sonography.

Other features of the invention will become apparent in the course of the following descriptions of exemplary embodiments which are given for illustration of the invention and are not intended to be limiting thereof.

EXAMPLE 1

Synthesis of 2-{[5-(3-{2-[(6-Hydroxycarbamoyl-7-isobutyl-8-oxo-2-oxa-9-aza-bicyclo[10.2.2]hexadeca-1(15),12(16),13-triene-10-carbonyl)-amino]-acetylamino}-propylcarbamoyl)-pyridin-2-yl]-hydrazonomethyl}-benzenesulfonic acid

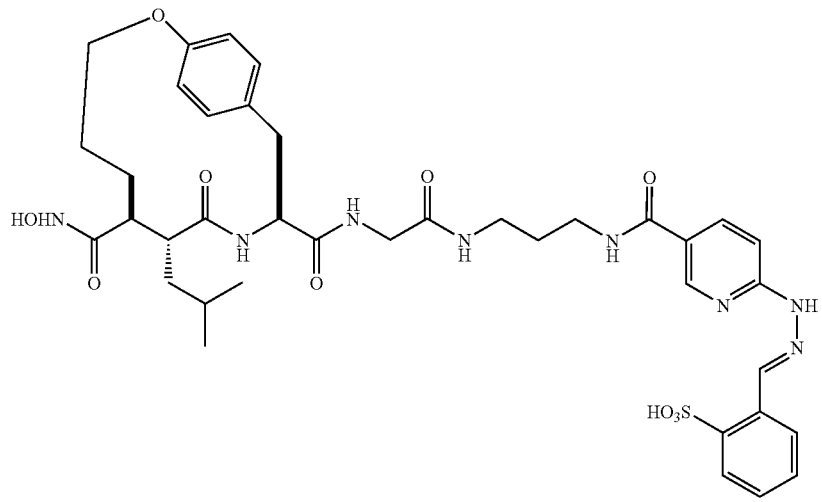

A. Preparation of [3-(2-Benzyloxycarbonylamino-acetylamino)-propyl]-carbamic acid tert-butyl ester

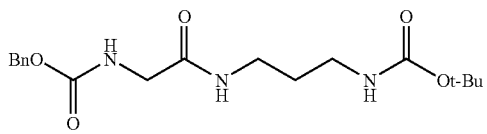

To 3 grams of (3-Amino-propyl)-carbamic acid tert-butyl ester in 15 ml of dimethylformamide was added 3 grams of N-benzyloxycarbonyl glycine, 4.7 mL of N-methylmorpholine and 5.06 grams of TBTU. The reaction was cooled to 0 degrees C. for 30 minutes then allowed to stir at room temperature overnight. The volatiles were removed under reduced pressure and the resulting material was dissolved in ethyl acetate and washed with 10% citric acid. The aqueous was extracted an additional two times with ethyl acetate, combined and washed with water, saturated aqueous sodium bicarbonate, water, brine and dried over $MgSO_4$. The volatiles were removed under reduced pressure and the resulting material was crystallized from EtOAc/hexane affording 4.55 grams of the desired product as a tan solid. LRMS found 388.3=$(M+Na)^+$

B. Preparation of [3-(2-Amino-acetylamino)-propyl]-carbamic acid tert-butyl ester

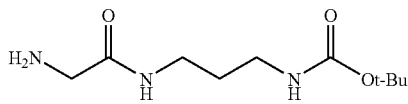

To 4.16 grams of the compound from Example 1A in 25 mL of methanol was added 0.5 grams of 10% Pd-C. The reaction was stirred under $H_2$ (balloon) for 2. hours. The reaction was filtered through a 0.45 μM PTFE filter and the volatiles were removed under reduced pressure affording 2.5 grams of the desired product. LRMS found 232.3 $(M+H)^{+1}$.

C. Preparation of 3-{2-[(6-Benzyloxycarbamoyl-7-isobutyl-8-oxo-2-oxa-9-aza-bicyclo[10.2.2] hexadeca-1(15),12(16),13-triene-10-carbonyl)-amino}-propyl)-carbamic acid tert-butyl ester

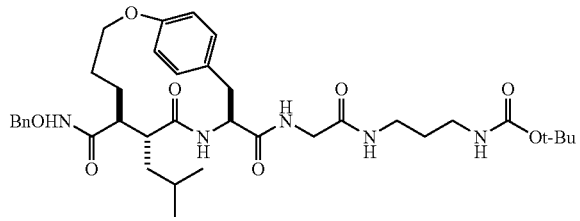

To 0.25 grams of 6-Benzyloxycarbamoyl-7-isobutyl-9,-oxo-2-oxa-9-aza-bicyclo[10.2.2]hexadeca-1(15),12(16),13-triene-10-carboxylic acid in 10 mL of dimethylformamide was added 0.1,7 ml. N-methylmorpholine and 0.217 grams of TBTU. After 10 minutes 0.359 grams of the compound from Example 1B was added. The reaction was allowed to stir at room temperature overnight, then it was heated at 70 degrees C. for 30 minutes. The volatiles were removed under reduced pressure and the resulting material was dissolved in EtOAc, washed with 10% aqueous citric acid, water, saturated $NaHCO_3$, brine and dried over $MgSO_4$. The resulting material was chromatographed on silica gel eluting with 2% $MeOH/CHCl_3$ affording 0.274 grams of the desired product.

D. Preparation of 3-{2-[(6-Hydroxycarbamoyl-7-isobutyl-8-oxo-2-oxa-9-aza-bicyclo[10.2.2] hexadeca-1(15),12(16),13-triene-10-carbonyl)-amino}-propyl)-carbamic acid tert-butyl ester

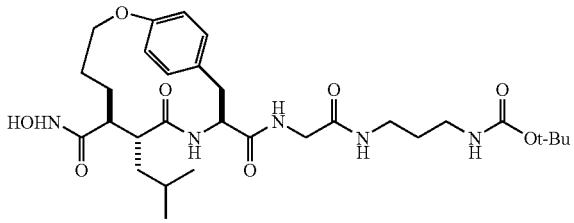

To 0.035 grams of the compound from Example 1C in 5 mL of methanol was added 0.050 grams of 5% $Pd/BaSO_4$. The reaction was stirred under hydrogen (balloon) for 2 hours, then filtered through a 0.,45 μM PTFE filter and the volatiles were removed under reduced pressure affording 0.031 grams of the desired compound. LRMS found 604.4 $(M-H)^{-1}$.

E. Preparation of 7-Isobutyl-8-oxo-2-oxa-9-aza-bicyclo[10.2.2]hexadeca-1(15),12(16),13-triene-6,10-dicarboxylic acid 10-{[(3-amino-propylcarbamoyl)-methyl]-amide}6-hydroxyamide trifluoroacetic acid salt

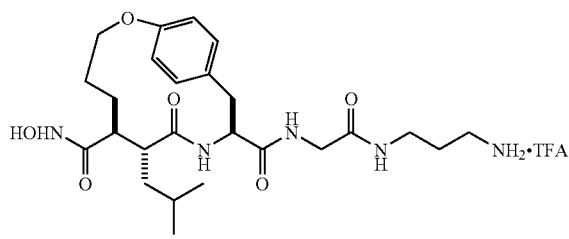

To 0.025 grams of the compound form Example 1D was added 1 mL of trifluoroacetic acid. The reaction was stirred 1 hour and the volatiles were removed under reduced pressure affording 0.017 grams of the desired compound. LRMS found 506.4 $(M+H)^{+1}$.

F. Preparation of 2-{[5-(3-{2-[(6-Hydroxycarbamoyl-7-isobutyl-8-oxo-2-oxa-9-aza-bicyclo[10;2.2]hexadeca-1(15),12(16),13-triene-10-carbonyl)-amino]-acetylamino}-propylcarbamoyl)-pyridin-2-yl]-hydrazonomethyl}-benzenesulfonic acid To a stirred solution of 0.050 grams of the compound from Example 1E was added 0.031 mL of N-methylmorpholine and 0.035 grams of 6-[N"-(2-Sodio-sulfo-benzylidene)-hydrazino]-nicotinic acid 2,5-dioxo-pyrrolidin-1-yl ester. The reaction was stirred at ambient temperature overnight. Volatiles were removed under reduced pressure and the resulting material was purified by reverse phase HPLC affording 0.08 grams of the desired compound. LRMS found 807 $(M-H)^{-1}$.

EXAMPLE 2

Synthesis of 2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzenesulfonic acid

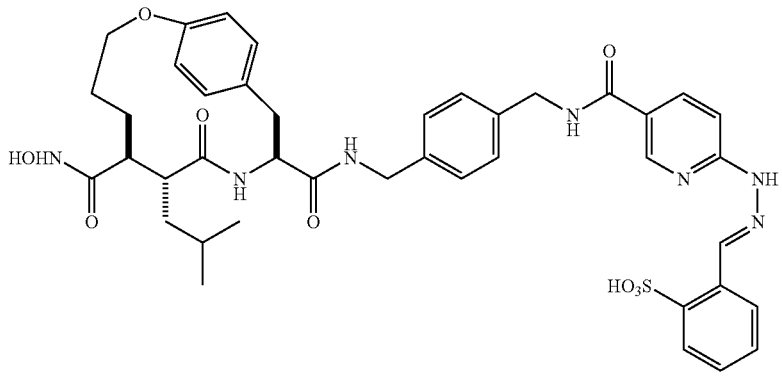

A. Preparation of (4-Aminomethyl-benzyl)carbamic acid tert-butyl ester

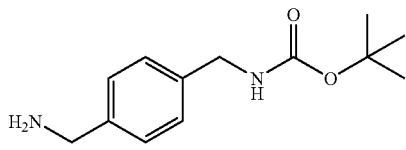

To a stirred solution of 5.3 grams of p-xylenediamine in 20 mL of dimethylformamide was added a solution of 2.12 grams of di-tert-butyl-dicarbonate in 50 mL of dimethylformamide by syringe pump over 1 hour. After stirring an additional 10 minutes the volatiles were removed under reduced pressure and the resulting material was chromatographed on silica gel eluting with 5% MeOH/CHCl$_3$ affording 2 grams of the desired compound. LRMS found 237.2 $(M+H)^{+1}$.

B. Preparation of (4-{[(6-Benzyloxycarbamoyl-7-isobutyl-8-oso-2-oxa-9-aza-bicyclo[10.2.2]hexadeca-1(15),12(16),13-triene-10-carbonyl)-amino]-methyl}-benzyl)-carbamic acid tert-butyl ester

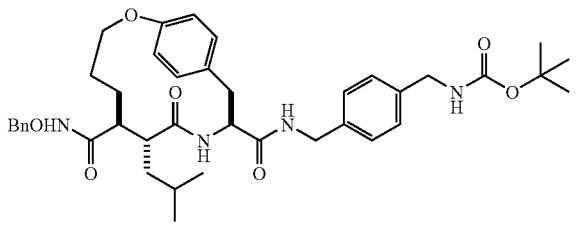

To 0.20 grams of 6-Benzyloxycarbamoyl-7-isobutyl-9-oxo-2-oxa-9-aza-bicyclo[10.2.2]hexadeca-1(15),12(16),13-triene-10-carboxylic acid in 5 mL of dimethylformamide was added 0.18 mL of n-methylmorpholine and 0.173 grams of TBTU. After stirring; 20 minutes 0.293 grams of the compound from Example 2A was added. After stirring at ambient temperature overnight the reaction was heated to 80 degrees C. for 30 minutes. The volatiles were removed under reduced pressure and the resulting material was dissolved in EtOAc, washed with 10% aqueous citric acid, water, saturated NaHCO$_3$, brine and dried over MgSO$_4$. The volatiles were removed under reduced pressure affording 0.296 grams of the desired compound. LRMS found 699.4 $(M-H)^{-1}$.

C. Preparation of (4-{[(6-Hydroxycarbamoyl-7-isobutyl-8-oso-2-oxa-9-aza-bicyclo[10.2.2]hexadeca-1(15),12(16),13-triene-10-carbonyl)-amino]-methyl}-benzyl)-carbamic acid tert-butyl ester

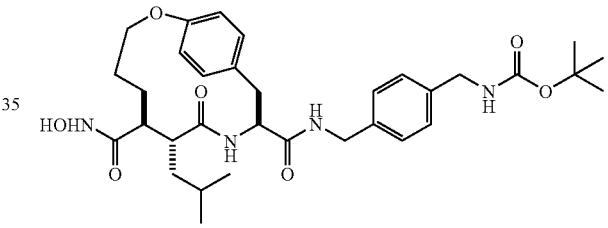

To 0.275 grams of the compound from Example 2B in 20 mL of methanol was added 0.50 grams of pre-hydrogenated 5% pd-BaSO$_4$. The reaction was stirred 3 hours under H$_2$ (Balloon) at which time an additional portion of 0.25 grams of 5% Pd-BaSO4 was added and the stirring was continued for another hour. The mixture was filtered through a 0.45 uM PTFE filter and the volatiles were removed under reduced pressure affording 0.24 grams of the desired compound. LRMS found 609.4 $(M-H)^{-1}$.

D. Preparation of 7-Isobutyl-8-oxo-2-oxa-9-aza-bicyclo[10.2.2]hexadeca-1(15),12(16),13-triene-6,10-dicarboxylic acid 10-(4-aminomethyl-benzylamice) 6-hydroxyamide trifluoroacetic acid salt

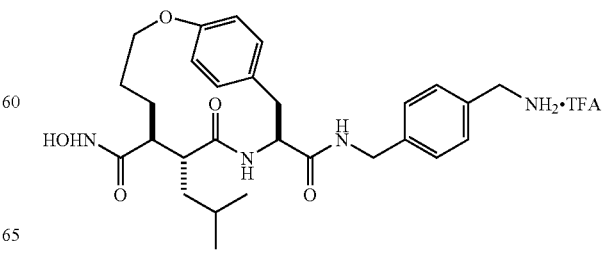

To 0.225 grams of the compound from Example 2C in 5 mL of CH$_2$Cl$_2$ was added 2 mL of trifluoroacetic acid. The reaction was stirred one hour at ambient temperature. The volatiles were removed under reduced pressure affording the desired compound. LRMS found 509.4 (M–H)$^{-1}$.

E. Preparation of 2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzenesulfonic acid To 0.050 grams of the compound from Example 2D in 1 mL of dimethylformamide was added 0.031 mL of N-methylmorpholine and 0.035 grams of of 6-[N"-(2-Sodio-sulfo-benzylidene)-hydrazino]-nicotinic acid 2,5-dioxo-pyrrolidin-1-yl ester. After stirring overnight an ambient temperature the volatiles were removed under reduced pressure and the resulting material was purified by reverse phase HPLC affording 0.06 grams the desired compound. LRMS found 814 (M+H)$^{+1}$.

EXAMPLE 3

Synthesis of 2-[7-({N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}methyl)-1,4,7,10-tetraaza-4,10-bis(carboxymethyl)cyclododecyl]acetic acid mmol) and allowed to react for 15 min at ambient temperatures under nitrogen. 2-{[7-(N-Hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide TFA salt (1 mmol) is added to this solution and stirring is continued at ambient temperatures under nitrogen for 18 h. The DMF is removed under vacuum and the resulting residue is triturated in ethyl acetate or diethyl ether and filtered. If necessary, the crude is purified by preparative HPLC on a C18 column using a water-:ACN:0.1% TFA gradient and the product fraction is lyophilized to give the DOTA-conjugate. The DOTA conjugate is stirred in degassed TFA at room temperature under nitrogen for 2 h. The solution is concentrated and the resulting residue is purified by preparative HPLC on a C18. column using a water:ACN:0.1% TFA gradient. The product fraction is lyophilized to give the title compound.

EXAMPLE 4

Synthesis of 2-{7-[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)methyl]-1,4,7,10-tetraaza-4,10-bis(carboxymethyl)cyclododecyl}acetic acid

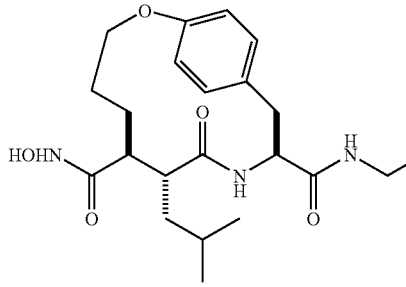
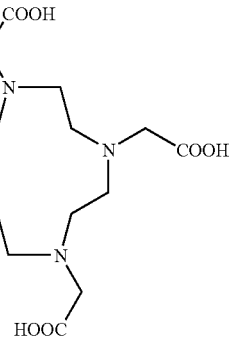

A solution of the commercially (Macrocyclics) available DOTA tri-t-butyl ester (1.5 mmol) and Hunig's base (6 mmol) in anhydrous DMF are treated with HBTU (1.25

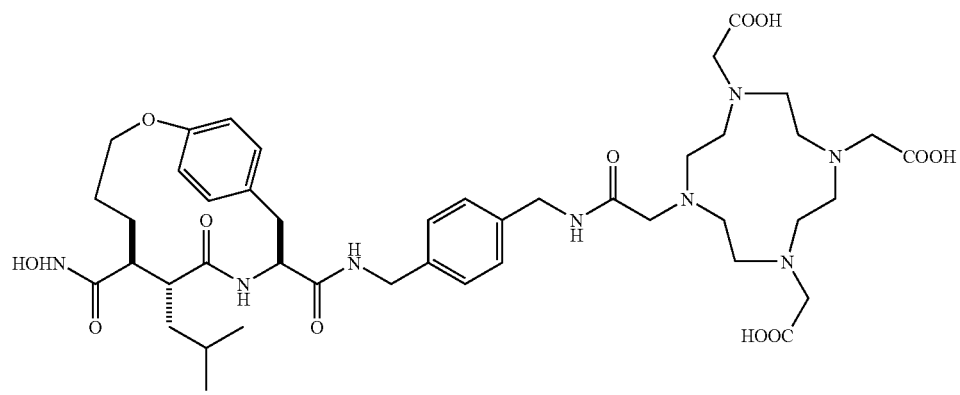

A solution of the commercially (Macrocyclics) available DOTA tri-t-butyl ester (1.5 mmol) and Hunig's base (6 mmol) in anhydrous DMF are treated with HBTU (1.25 mmol) and allowed to react for 15 min at ambient temperatures under nitrogen. [7-(N-Hydroxycarbamoyl)(3S,6R,7S)-4-aza-6(2-methylpropyl)-11-oxa-5-oxobicyclo[10.2.2]hexadeca-1(15),12(16),13-trien-3-yl]-N-{[4-(aminomethyl)phenyl]methyl}carboxamide TFA salt (1 mmol) is added to this solution and stirring is continued at ambient temperatures under nitrogen for 18 h. The DMF is removed under vacuum and the resulting residue is triturated in ethyl acetate or diethyl ether and filtered. If necessary, the crude is purified by preparative HPLC on a C18 column using a water:ACN:0.1% TFA gradient and the product fraction is lyophilized to give the DOTA-conjugate.

The DOTA conjugate is stirred in degassed TFA at room temperature under nitrogen for 2 h. The solution is concentrated and the resulting residue is purified by preparative HPLC on a C18 column using a water:ACN:0.1% TFA gradient. The product fraction is lyophilized to give the title compound.

EXAMPLE 5
Synthesis of 2-(7-{[N-(1-{N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}-2-sulfoethyl)carbamoyl]methyl}-1,4,7,10-tetraaza-4,10-bis(carboxymethyl)cyclododecyl)acetic acid A. Preparation of N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-2-aminopropanesulfonic acid

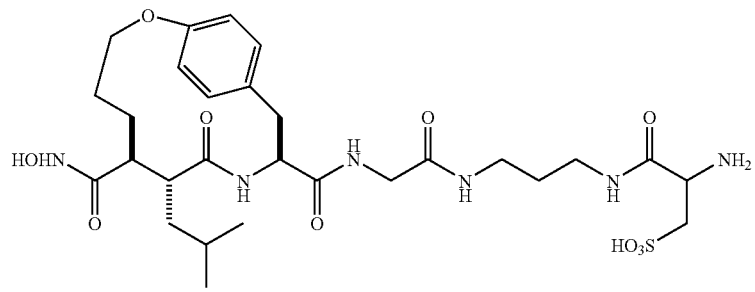

2-{[7-(N-Hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide TFA salt (1 mmol) is dissolved in anhydrous DMF, and treated with the N-hydroxysuccinimide ester (1.5 mmol) of Boc-cysteic acid (as described in *Liebigs Ann. Chem.* 1979, 776–783) and Hunig's base. The solution is stirred at ambient temperatures under nitrogen for 18 h, and the DMF is removed under vacuum. The resulting residue is purified by preparative HPLC on a C18 column using a water:ACN:0.1% TFA gradient. The product fraction is lyophilized to give a solid which is dissolved in degassed TFA and stirred at ambient temperatures for 30 min. The solution is concentrated under vacuum, and the resulting residue is dissolved in 50% ACN and lyophilized to give the boc deprotected product N-[3-

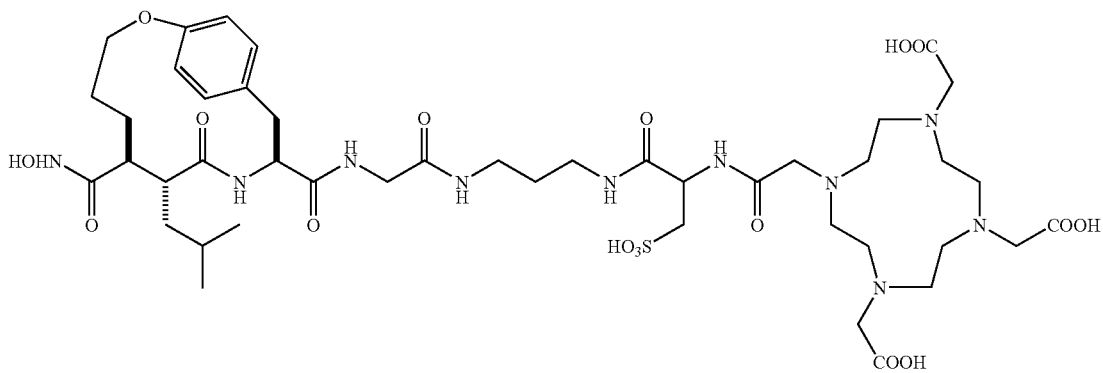

(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-2-aminopropanesulfonic acid.

B. Preparation of 2-(7-{[N-(1-{N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}-2-sulfoethyl)carbamoyl]methyl}-1,4,7,10-tetraaza-4,10-bis(carboxymethyl)cyclododecyl)acetic acid A solution of the commercially (Macrocyclics) available DOTA tri-t-butyl ester (1.5 mmol) and Hunig's base (6 mmol) in anhydrous DMF are treated with HBTU (1.25 mmol) and allowed to react for 15 min at ambient temperatures under nitrogen. N-[3-(2-{[7-(N-Hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-2-aminopropanesulfonic acid is added to this solution and stirring is continued at ambient temperatures under nitrogen for 18 h. The DMF is removed under vacuum and the resulting residue is triturated in ethyl acetate or diethyl ether and filtered. If necessary, the crude is purified by preparative HPLC on a C18 column using a water:ACN:0.1% TFA gradient and the product fraction is lyophilized to give the DOTA-conjugate. The DOTA conjugate is stirred in degassed TFA at room temperature under nitrogen for 2 h. The solution is concentrated and the resulting residue is purified by preparative HPLC on a C18 column using a water:ACN:0.1% TFA gradient. The product fraction is lyophilized to give the title compound.

EXAMPLE 6

Synthesis of 2-[7-({N-[1-(N-{[4-({[7-(N-hydroxycarbamoyl) (3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)-2-sulfoethyl]carbamoyl}methyl)-1,4,7,10-tetraaza-4,10-bis(carboxymethyl)cyclododecyl]acetic acid A. Preparation of N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}-2-aminopropanesulfonic acid

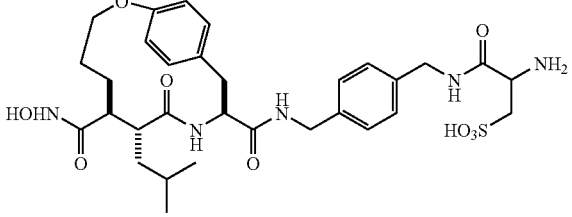

[7-(N-Hydroxycarbamoyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide TFA salt (1 mmol) is dissolved in anhydrous DMF, and treated with the N-hydroxysuccinimide ester (1.5 mmol) of Boc-cysteic acid (as described in Liebigs Ann. Chem. 1979, 776–783) and Hunig's base. The solution is stirred at ambient temperatures under nitrogen for 18 h, and the DMF is removed under vacuum. The resulting residue is purified by preparative HPLC on a C18 column using a water:ACN:0.1% TFA gradient. The product fraction is lyophilized to give a solid, which is dissolved in degassed TFA and stirred at ambient temperatures for 30 min. The solution is concentrated under vacuum, and the resulting residue is dissolved in 50% ACN and lyophilized to give the boc deprotected product N-{[4-({[7-(N-hydroxycarbamoyl)(3S,6R,7S)-4-aza-6-(2-methylpropyl)-11-oxa-5-oxbbicyclo[10.2.2]hexadeca-1(15),12(16),13-trien-3-yl]-carbonylamino}methyl)phenyl]methyl,}-2-aminopropanesulfonic acid.

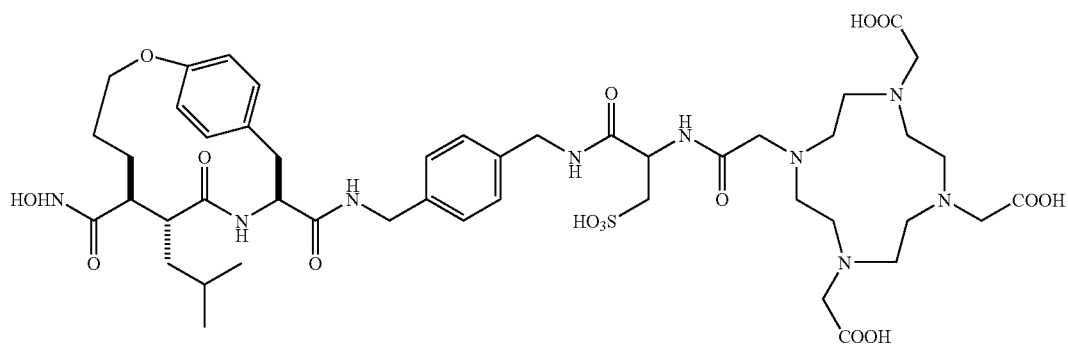

B. Preparation of 2-[7-({N-[1-(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)-2-sulfoethyl]carbamoyl}methyl)-1,4,7,10-tetraaza-4,10-bis(carboxymethyl)cyclododecyl]acetic acid A solution of the commercially, (Macrocyclics) available DOTA tri-t-butyl ester (1.5 mmol).and Hunig's base (6 mmol) in anhydrous DMF are treated with HBTU (1.25 mmol) and allowed to react for 15 min at ambient temperatures under nitrogen. N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}-2-aminopropanesulfonic acid is added to this solution and stirring is continued at ambient temperatures under nitrogen for 18 h. The DMF is removed under vacuum and the resulting residue is triturated in ethyl acetate or diethyl ether and filtered. If necessary, the crude is purified by preparative HPLC on a C18 column using a water:ACN:0.1% TFA gradient and the product fraction is lyophilized to give the DOTA-conjugate.

The DOTA conjugate is stirred in degassed TFA at room temperature under nitrogen for 2 h. The solution is concentrated and the resulting residue is purified by preparative HPLC on a C18 column using a water:ACN:0.1% TFA gradient. The product fraction is lyophilized to give the title compound.

EXAMPLE 7

Synthesis of 2-({2-[({N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}methyl)(carboxymethyl)amino}ethyl){2-[bis(carboxymethyl)amino]ethyl}amino]acetic acid

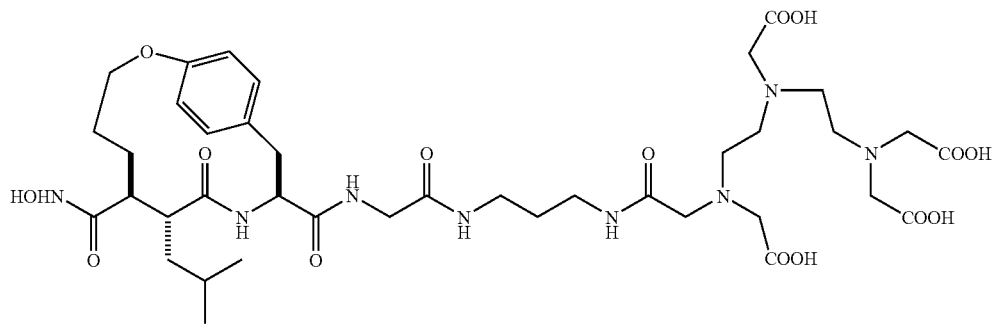

To a solution of 2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide TFA salt (1 mmol) in DMF (20 mL) is added triethylamine (3 mmol). This solution is added dropwise over 4 h to a solution of diethylenetriaminepentaacetic dianhydride (3 mmol) in DMF (20 mL) and methyl sulfoxide (20 mL). The reaction mixture is then stirred for 16 h, concentrated to an oil under high vacuum and purified by preparative HPLC to give the title compound.

EXAMPLE 8

Synthesis of 2-[(2-{[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)methyl](carboxymethyl)amino}ethyl){2-[bis(carboxymethyl)amino]ethyl}amino]acetic acid

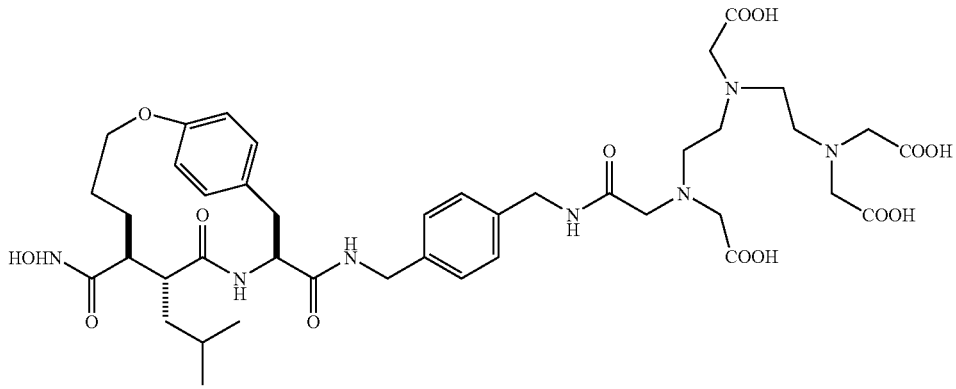

To a solution of [7-(N-hydroxycarbambyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide TFA salt (1 mmol) in DMF (20 mL) is added triethylamine (3 mmol). This solution is added dropwise over 4 h to a solution of diethylenetriaminepentaacetic dianhydride (3 mmol) in DMF (20 mL) and methyl sulfoxide (20 mL). The reaction mixture is then stirred for 16 h, concentrated to an oil under high vacuum and purified by preparative HPLC to give the title compound.

EXAMPLE 9

Synthesis of N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-4,5-bis[2-(ethoxyethylthio)acetylamino]pentanamide

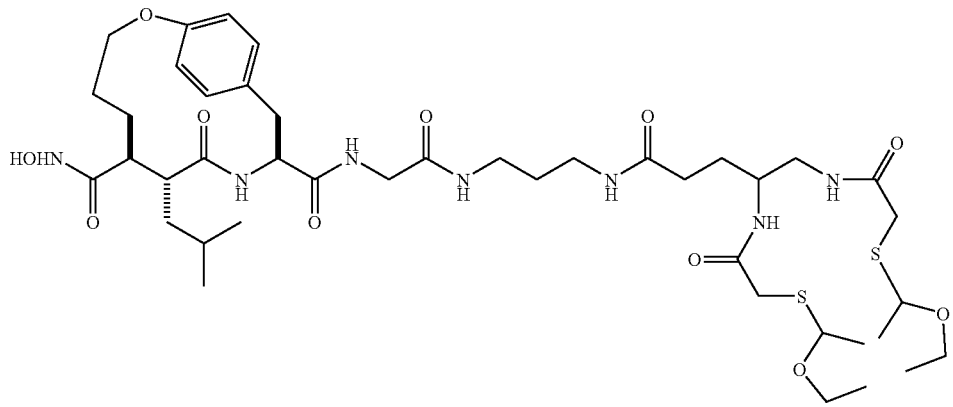

To a solution of 2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide TFA salt (1 mmol) and triethylamine (3 mmol) in DMF is added 2,3,5,6-tetrafluorophenyl 4,5-bis(S-1-ethoxyethyl-mercaptoacetamido)pentanoate (1.1 mmol), and the reaction mixture is stirred for 18 hours. DMF is removed in vacuo and the crude residue is triturated with ethyl acetate. The product is filtered, dried, and if necessary, further purified by preparative HPLC to give the title compound.

EXAMPLE 10

Synthesis of N-{[4-({[7-(N-hydroxycarbamoyl)(3S, 6R,7S)-4-aza-6-(2-methylpropyl)-11-oxa-5-oxobicyclo[10.2.2]hexadeca-1(15),12(16),13-trien-3-yl]carbonylamino}methyl)-phenyl]methyl}-4,5-bis[2-(ethoxyethylthio)acetylamino]-pentanamide

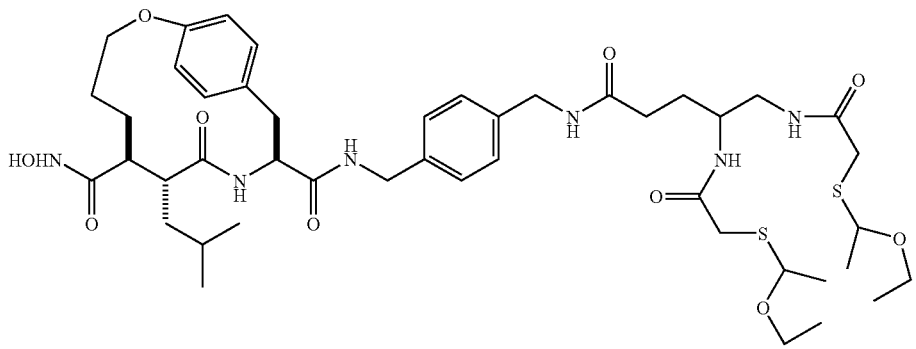

To a solution of [7-(N-hydroxycarbamoyl) (3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]-methyl}carboxamide TFA salt (1 mmol) and triethylamine (3 mmol) in DMF is added 2,3,5,6-tetrafluorophenyl 4,5-bis(S-1-ethoxyethyl-mercaptoacetamido) pentanoate (1.1 mmol), and the reaction mixture is stirred for 18 hours. DMF is removed in vacuo and the crude residue is triturated with ethyl acetate. The product is filtered, dried, and if necessary, further purified by preparative HPLC to give the title compound.

EXAMPLE 11

Synthesis of 1-(1,2-Dipalmitoyl-sn-glycero-3-phosphoethanolamino)-α,ω-dicarbonylPEG$_{3400}$-2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide conjugate

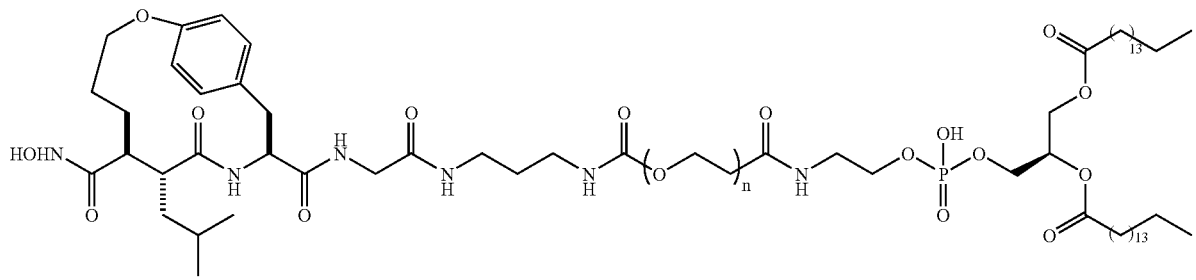

To solution of the commercially available (Shearwater Polymers) succinimidyl ester, DSPE-PEG-NHS ester (1 mmol) in 25 ml chloroform is added 2-{[7-(N-hydroxycarbamoyl) (3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide TFA salt (1 mmol). Sodium carbonate (1 mmol) and sodium sulfate (1 mmol) are added and the solution is stirred at room temperature under nitrogen for 18 h. The solvent is removed in vacuo and the crude product is purified using preparative HPLC to obtain the title compound.

EXAMPLE 12

Synthesis of 1-(1,2-Dipalmitoyl-sn-glycero-3-phosphoethanolamino)-α,Ω-dicarbonylPEG$_{3400}$-[7-(N-hydroxycarbamoyl)(3S,6R,7S)-4-aza-6-(2-methylpropyl)-11-oxa-5-oxobicyclo[10.2.2] hexadeca-1(15),12(16),13-trien-3-yl]-N-{[4-(aminomethyl)phenyl]methyl}carboxamide conjugate

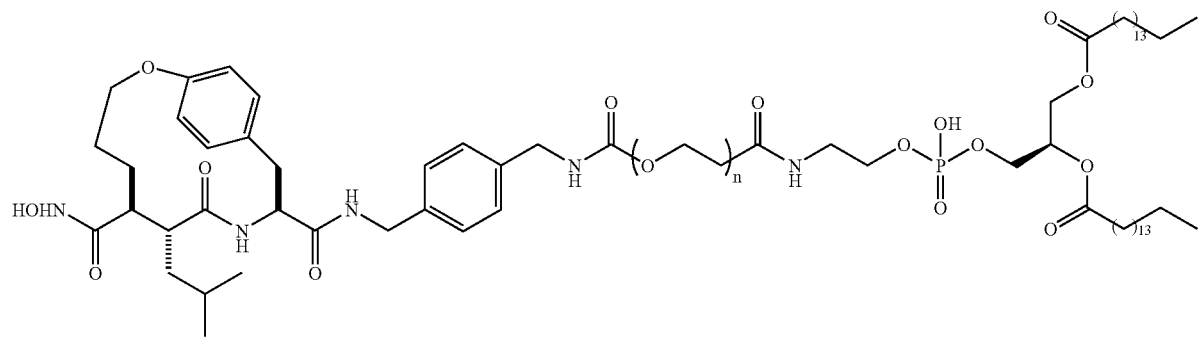

To solution of the commercially available (Shearwater Polymers) succinimidyl ester, DSPE-PEG-NHS ester (1 mmol) in 25 ml chloroform is added [7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide TFA salt (1 mmol). Sodium carbonate (1 mmol) and sodium sulfate (1 mmol) are added and the solution is stirred at room temperature under nitrogen for 18 h. The solvent is removed in vacuo and the crude product is purified using preparative HPLC to obtain the title compound.

EXAMPLES 13 AND 14

Synthesis of $^{99m}$Tc Complexes

To a lyophilized vial containing 4.84 mg TPPTS, 6.3 mg tricine, 40 mg mannitol, succinic acid buffer, pH 4.8, and 0.1% Pluronic F-64 surfactant, was added 0.75–1.1 mL sterile water for injection, 0.2–0.45 mL (20–40 μg) of the compounds of Examples 1 and 2, respectively, in deionized water or 50% aqueous ethanol, and 0.2–0.4 mL of $^{99m}$TcO$_4^-$ (50–120 mCi) in saline. The reconstituted kit was heated in a 100° C. water bath for 10–15 minutes, and was allowed to cool 10 minutes at room temperature. A sample was then analyzed by HPLC.

HPLC Method for Example 13

Column: Zorbax C18, 25 cm×4.6 mm

Flow rate : 1.0 mL/min

Solvent A: 10 mM sodium phosphate buffer, pH 6.0

Solvent B : 100% CH$_3$CN

| | t (min) | | | | | |
|---|---|---|---|---|---|---|
| | 0 | 20 | 21 | 30 | 31 | 40 |
| % Solvent B | 0 | 25 | 75 | 75 | 0 | 0 |

HPLC Method for Example 14

Column: Zorbax C18, 25 cm×4.6 mm

Flow rate : 1.0 mL/min

Solvent A: 10 mM sodium phosphate buffer, pH 6.0

Solvent B : 100% CH$_3$CN

| | t (min) | | | | | |
|---|---|---|---|---|---|---|
| | 0 | 20 | 21 | 26 | 27 | 40 |
| % Solvent B | 0 | 25 | 75 | 75 | 0 | 0 |

| Example # | Reagent Ex. # | Ret. Time (min) | % Yield |
|---|---|---|---|
| 13 | 1 | 7.8 | 79 |
| 14 | 2 | 16.7 | 81 |

EXAMPLE 15

Synthesis of 2-[2-({5-[N-(5-(N-hydroxycarbamoyl) (5R)-5-{3-[4-(3,4-dimethoxyphenoxy)phenyl]-3-methyl-2-oxopyrrolidinyl}pentyl)carbamoyl](2-pyridyl)}amino)(1Z)-2-azavinyl]benzenesulfonic acid

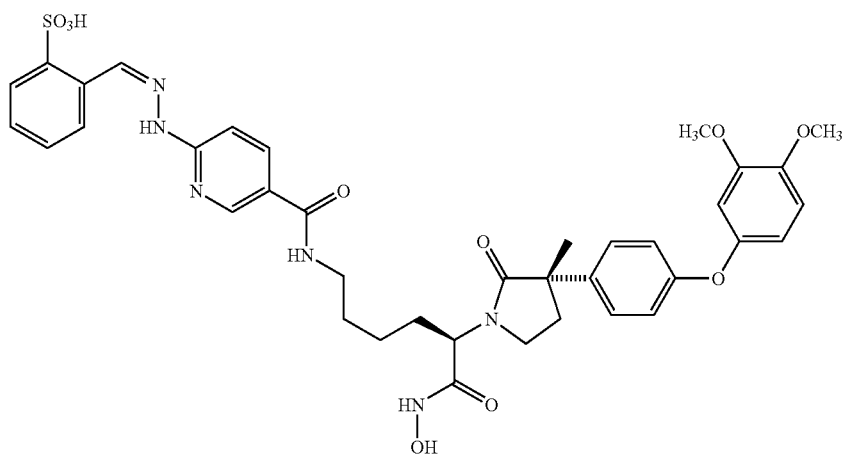

The title compound can be synthesized as shown in Scheme I from the starting materials described in the following patent applications which are hereby incorporated by reference into this patent application: U.S. patent application Ser. Nos. 09/165,747, 08/743,439, 09/134,484, 09/247,675, 09/335,086, 09/312,066, 09/311,168, 60/127,594, and 60/127,635.

81
-continued

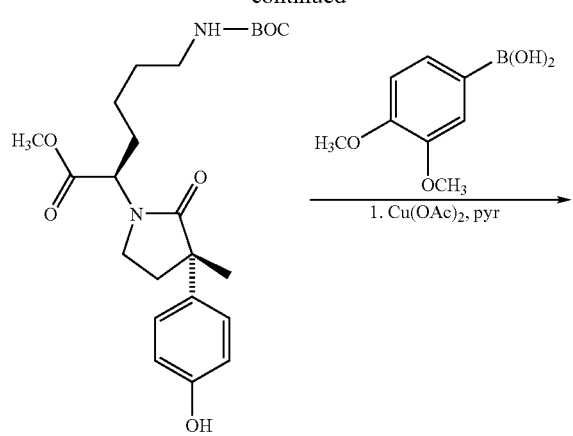

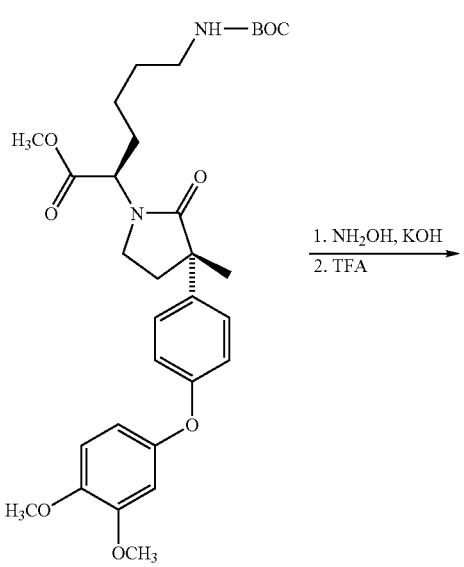

82
-continued

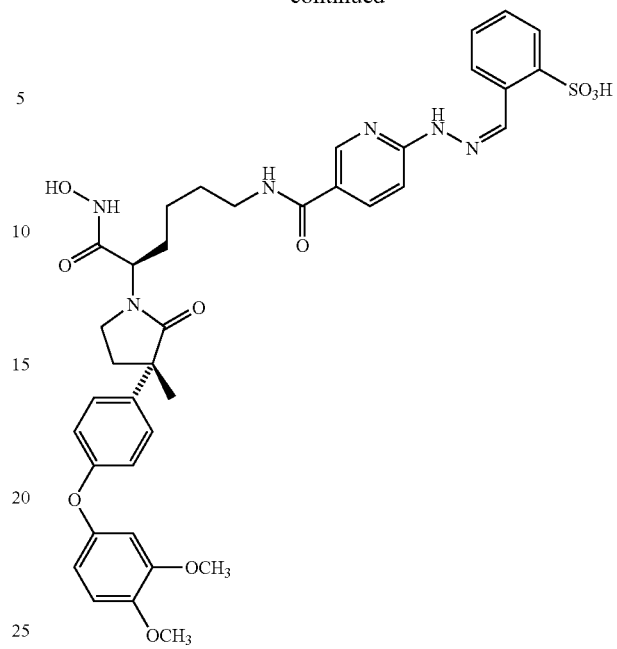

EXAMPLE 16

Synthesis of 2-(2-{[5-(N-{3-[3-(N-hydroxycarbamoyl)(4S)-4-({4-[(4-methylphenyl)methoxy]piperidyl}carbonyl)piperidyl]-3-oxopropyl}carbamoyl)(2-pyridyl)]amino}(1Z)-2-azavinyl)benzenesulfonic acid

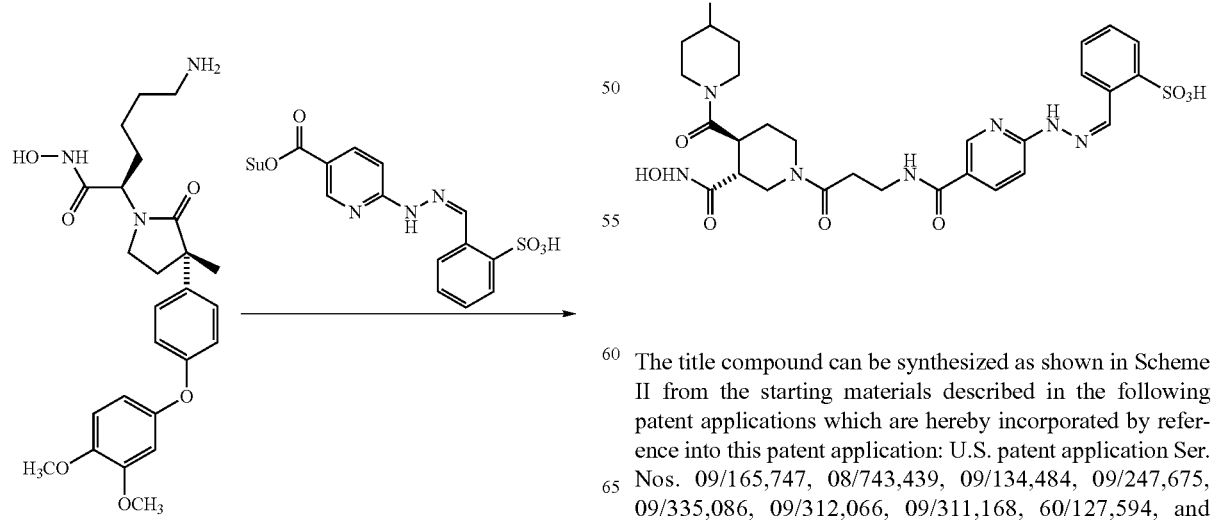

The title compound can be synthesized as shown in Scheme II from the starting materials described in the following patent applications which are hereby incorporated by reference into this patent application: U.S. patent application Ser. Nos. 09/165,747, 08/743,439, 09/134,484, 09/247,675, 09/335,086, 09/312,066, 09/311,168, 60/127,594, and 60/127,635.

Scheme II
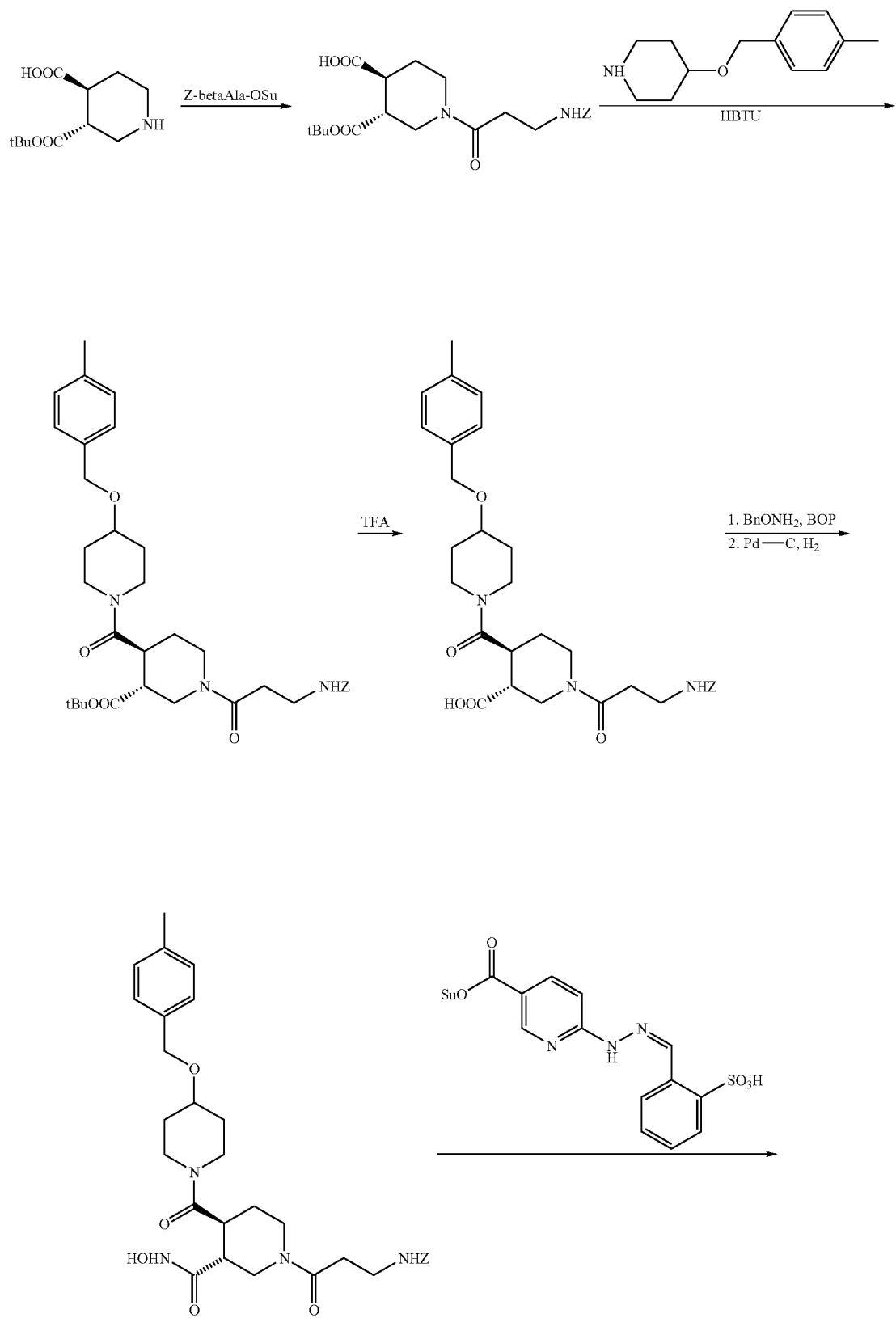

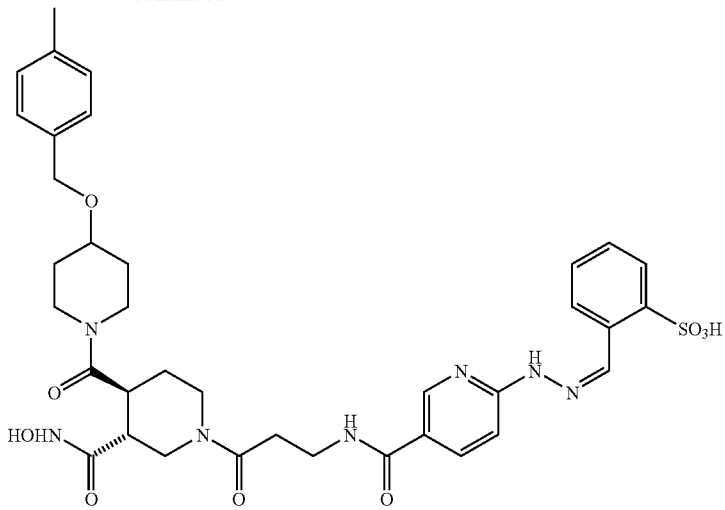

EXAMPLE 17

Synthesis of N-BOC-Glycine-(3-carbobenzyloxyamido)propylamide

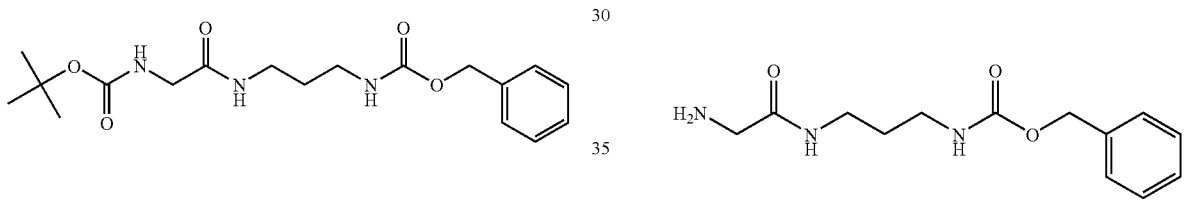

Di-isopropylethylamine (7.0 mL, 40 mmol) was added to a suspension of N-t-butyloxycarbonylglycine N-hydroxysuccinimide ester (5.569 g, 20 mmol) and N-carbobenzyloxy-1,3-diaminopropane hydrochloride (5.0 g, 20 mmol) in dichloromethane (50 ml). The solution became clear over several minutes. After 30 minutes, additional of N-t-butyloxycarbonylglycine N-hydroxysuccinimide ester (0.275 g, 1 mmol) was added. The solution was extracted with water, followed by saturated aqueous $NaHCO_3$, then by 0.5 N HCl. The dichloromethane solution was filtered through a short column of $Na_2SO_4$ and evaporated in vacuo to obtain 4.1 g (56%) of N-BOC-Glycine-(3-carbobenzyloxyamido)propylamide. MS: m/e= 366 (M+H$^+$), 310 (M−$C_4H_9$+H$^+$), 266 (M−BOC+H$^+$).

Synthesis of Glycine-(3-carbobenzyloxyamido)propylamide

N-BOC-Glycine-(3-carbobenzyloxyamido)propylamide (260 mg, 0.71 mmol) was dissolved in dichloromethane (3 mL) and trifluoroacetic acid (0.5 mL) added. After 20 minutes, the solution was evaporated in vacuo, dissolved in dichloromethane (2 mL) and evaporated in vacuo to obtain the crude product which was used directly in the next reaction. MS: m/e =266 (M+H$^+$).

Synthesis of 17a

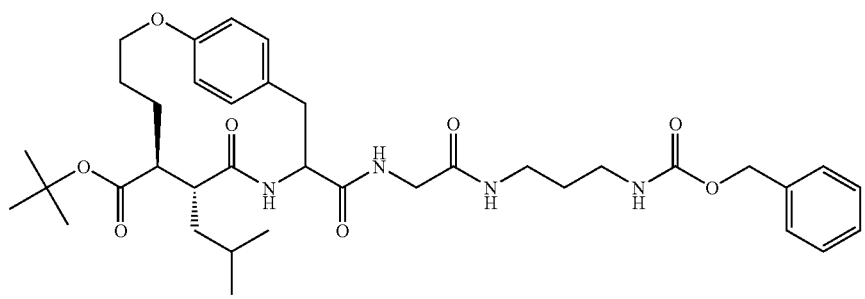

Di-isopropylethylamine (0.25 mL, 1.4 mmol) was added to a mixture of 1 (300 mg, 0.69 mmol) and HBTU (270 mg, 0.71 mmol) in dichloromethane (5 mL). Dimethylformamide (1 mL) was added to obtain a clear solution. After 30 minutes, a solution of Glycine-(3-carbobenzyloxyamido)propylamide (~0.71 mmol) and di-isopropylethyl amine (0.25 mL, 1.4 mmol) in dichloromethane (1 mL) was added. The reaction mixture was extracted twice with 0.5 N HCl, once each with saturated aqueous NaCl, 1.0 N NaOH, saturated aqueous NaCl, and saturated aqueous NaHCO$_3$. The dichloromethane solution was filtered through a short column of Na$_2$SO$_4$ and evaporated in vacuo to obtain crude 17b (599 mg, 127%). MS: m/e=681 (M+H$^+$).

1

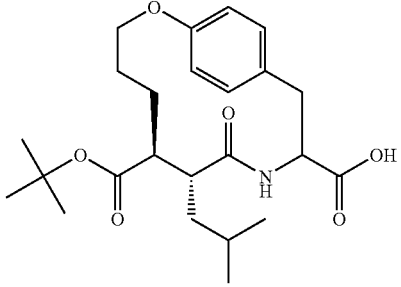

Synthesis of 17b

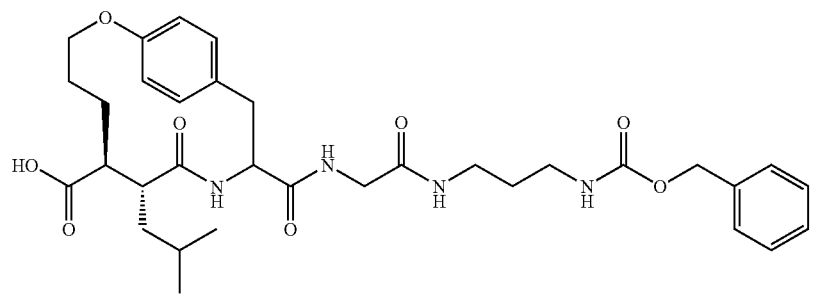

Trifluoroacetic acid (1 mL) was added to a solution of 17a (599 mg) in dichloromethane (5 mL) and allowed to stand at room temperature overnight. The solution was evaporated in vacuo, dissolved in dichloromethane (2 mL) and evaporated in vacuo to obtain 3 (714 mg). MS: m/e=625 (M+H$^+$).

Synthesis of 17c

A mixture of 3 (~0.3 g, ~0.5 mmol) and 10% Pd/C (25 mg) in ethanol (5 mL) was stirred under hydrogen (1 atm) for 2.5 hours. Disappearance of 17b was accompanied by the appearance of two peaks in the HPLC-:MS chromatogram, both of which exhibited base peaks at m/e=491 amu, consistent with (M+H+) for the loss of carbobenzyloxy group from 26b. The reaction mixture was filtered through Celite and evaporated in vacuo to obtain 17c.

Synthesis of 17d

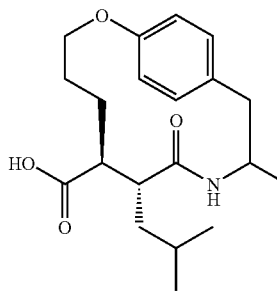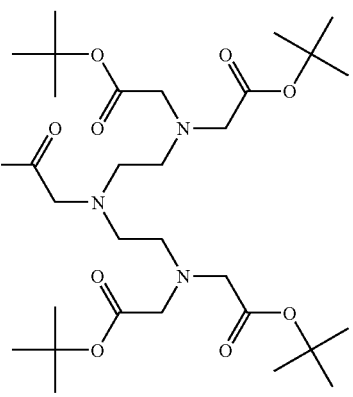

A mixture of N,N-bis[2-bis(1,1'-dimethylethoxy)-2-oxoethyl]-amino]ethyl]glycine (487 mg, 0.788 mmol), HBTU (288 mg, 0.760 mmol) and di-isopropylethyl amine (0.4 mL, 2.3 mmol) in dimethylformamide (4 mL) was stirred at room temperature. A solution of 4 (~0.5 mmol) in dimethylformamide (2 mL) was added in one portion. After 2 hours, ~⅔ of the solution was removed, partitioned between dichloromethane and 0.5 M HCl. The organic phase extracted once with 0.5 M HCl, then with saturated aqueous NaCl, filtered through a column of $Na_2SO_4$, and evaporated in vacuo to obtain crude 17d. MS: m/e 1090 (M+H$^+$), 546 (M+2H)$^{+2}$

Synthesis of 17e

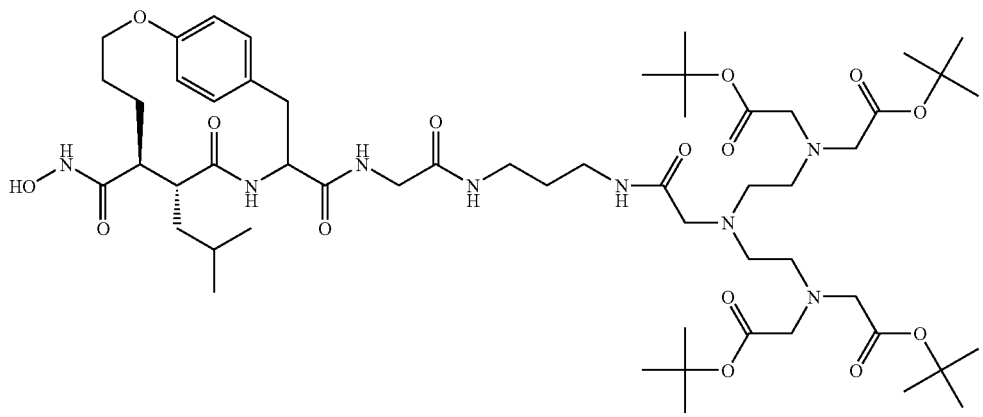

The remaining ⅓ of the reaction mixture 17d was treated with HBTU (75 mg, 0.26 mmol) and allowed to stir for 20 minutes. A solutions prepared from hydroxylamine hydrochloride (50 mg, 0.70 mmol) and di-isopropylethylamine (0.15 mL, 0.86 mmol) in dimethylformamide (0.5 mL) was added in one portion. The reaction mixture was partitioned between dichloromethane and 0.5 M HCl. The organic phase was extracted with saturated aqueous NaCl, then with saturated aqueous $NaHCO_3$. The $NaHCO_3$ phase was back-extracted with dichloromethane, the combined organic extracts filtered through a column of $Na_2SO_4$, and evaporated in vacuo. The crude product was purified by reverse-phase HPLC to obtain 14 mg of 27e. MS: m/e 1105 (M+H$^+$), 553 (M+2H)$^{+2}$ Synthesis of 17f

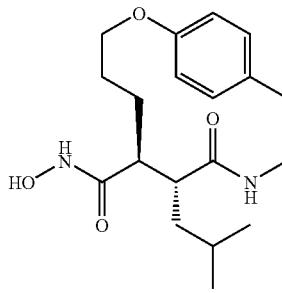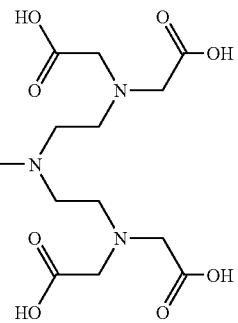

A solution of 17e in trifluoroacetic acid (0.5 mL) and dichloromethane (2 mL) was allowed to stand at room temperature overnight. The solution was evaporated in vacuo, dissolved in acetonitrile-water and purified by reverse-phase HPLC to obtain 3.4 mg of 17f. MS: m/e 881 (M+H$^+$), 441 (M+2H)$^{+2}$ Utility The pharmaceuticals of the present invention are useful for imaging of cardiovascular disease processes involving the degradation of the extracellular matrix. The radiopharmaceuticals of the present invention comprised of a gamma emitting isotope are useful for imaging of cardiovascular pathological processes involving the degradation of the extracellular matrix, including atherosclerosis, congestive heart failure, and restenosis of blood vessels after angioplasty.

The compounds of the present invention comprised of one or more paramagnetic metal ions selected from gadolinium, dysprosium, iron, and manganese, are useful as contrast agents for magnetic resonance imaging (MRI) of cardiovascular pathological processes involving extracellular matrix degradation.

The compounds of the present invention comprised of one or more heavy atoms with atomic number of 20 or greater are useful as X-ray contrast agents for X-ray imaging of cardiovascular pathological processes involving extracellular matrix degradation.

The compounds of the present invention comprised of an echogenic gas containing surfactant microsphere are useful as ultrasound contrast agents for sonography of cardiovascular pathological processes involving extracellular matrix degradation.

Representative compounds of the present invention were tested in the one or more of the following in vitro assays and were found to be active.
Matrix Metalloproteinase Assays for MMP-1 (collagenase-1), MMP-2 (gelatinase A), MMP-3 (stromelysin-1), MMP-8 (collagenase-2), MMP-9 (gelatinase B), MMP-13 (collagenase-3), MMP-14(membrane type 1 MMP), MMP-15 (membrane type 2 MMP), and MMP-16 (membrane type 3 MMP).
A. Reagents
1. MCA peptide substrate: Mca-Pro-Leu-Gly-Leu-Dpa-Ala-NH2. Peptide stocks are stored at −70 C in DMSO at 20 mM. Dilute peptide in 1x reaction buffer to a working concentration of 14 uM on day of use.
2. Enzyme buffer. 50 mM Tricine, 0.05% Brij-35, 400 mM NaCl, 10 mM CaCl2, 0.02% NaN3, pH 7.5.
3. Reaction buffer. 50 mM Tricine, 10 mM CaCl2, 0.02% NaN3, pH 7.5
4. Compounds. Stock compounds are at 10 mM in DMSO. Dilutions are done in buffer.
5. Plates. microfluor W flat bottom plates (Dynex Inc. Cat.#7905).
B. Assay
1. To 96 well fluorescent assay plates add 2 uL of DMSO control or compound dilutions to wells.
2. Add 20 uL of EDTA (0.5M) to each quench well.
3. Add 50 uL of enzyme at the appropriate concentration.
4. Add 150 uL of the MCA peptide at final concentration of 10 uM.
5. Incubate each plate for 1 hour at room temperature on an orbital shaker.
6. Add 20 uL of EDTA (0.5 M) to each test well to quench the reaction.
7. Read each plate at 330 nm excitation, 440 nm emission (Dynx plate reader)
8. Subtract each quench value from the corresponding test value.
9. % inhibition=100−(sample fluorescence/control fluorescence)×100.
TACE Assay
A. Reagents
1. MCA Peptide substrate: Mca-PLAQAV(Dpa)RSSSR-NH2. Peptide stocks are stored at −70 C in DMSO at 20 mM. Dilute peptide stock in reaction buffer to a working concentration of 20 uM on day of use.
2. Reaction buffer. 50 mM Tricine, 100 mM NaCl, 10 mM CaCl2, 1 mM ZnCl2, pH .7.5.
3. Compounds. Stock compounds are at 10 mM in DMSO
4. Plates. black Packard Optiplate (Cat.#HTRF-96)
5. Cytofluor Multi-well Plate Reader (Series 4000)
B. Assay
1. Initiate assay by adding 2 nM TACE to buffered solutions containing 10 μM MCA peptide substrate in the presence of increasing concentrations of compound.
2. Add 20 uL of EDTA (0.5M) to each quench well.
3. Total volume is 300 uL in each well.
4. Incubate the reaction mixtures for 1 hour at 28 C on an orbital shaker.
5. Add 20 uL of EDTA (0.5M) to each test well to quench the reaction.
6. Read each plate at 330 nM excitation, 395 nm emission
7. Subtract each quench value from the corresponding test value.

8. % inhibition=100−(sample fluorescence/control fluorescence)×100

In Vivo Models

Cardiovascular disease models that can be used to assess the diagnostic radiopharmaceuticals, magnetic resonance, X-ray and ultrasound contrast agents of the present invention are reviewed in J. Nucl. Cardiol., 1998, 5, 167–83. There are several well established rabbit models of atherosclerosis; one model produces predominantly proliferating smooth muscle cells by balloon deendothelialization of infradiaphragmatic abdominal aorta to simulate restenotic lesions; another model that produces simulated advanced human atherosclerotic plaque by balloon deendothelialization followed by a high cholesterol diet.

A model of congestive heart failure is described in Am. J. Physiol., 1998, 274, H1516-23. In general, Yorkshire pigs are randomly assigned to undergo 3 wks of rapid atrial pacing at 240 beats/min. or to be sham controls. The pigs are chronically instrumented to measure left ventricular function in the conscious state. The pigs are anesthetized.

A shielded stimulating electrode is sutured onto the left atrium, connected to a modified programmable pace maker and buried in a subcutaneous pocket. The pericardium is closed loosely, the thoracotomy is closed, and the pleural space is evacuated of air. After a recovery period of 7–10 days, the pacemaker is activated in the animals selected to undergo chronic rapid pacing. The animals are sedated, the pacemaker is deactivated (pacing groups only. After a 30 min stabilization period, indexes of LV function and geometry are determined (by echocardiography as a control) by injecting the radiolabeled compound. For biodistribution, the animals are anesthetized, the heart extirpate and the LV apex and midventricular regions are evaluated.

A rat model of reversible coronary occlusion and reperfusion is described in McNulty et al., J. Am. Physiol., 1996, H2283-9.

Obviously, numerous modifications and variations of the present invention are possible in light of the above teachings. It is therefore to be understood that within the scope of the appended claims, the invention may be practiced otherwise that as specifically described herein.

What is claimed is:

1. A method of detecting, imaging or monitoring congestive heart failure in a patient, comprising the steps of:
   administering a diagnostic agent to the patient; and
   acquiring an image of a site of concentration of the diagnostic agent in the patient by a diagnostic imaging technique;
   wherein the diagnostic agent comprises a diagnostic metal and a compound of the formula:

$(Q)_d-(L_n)_{x'}-K$ or a pharmaceutically acceptable salt thereof;
wherein
   Q is a matrix metalloproteinase inhibitor of formula (Ia) or (Ib):

[structural formulas with RHN, $R^1$, X, $R^3$, $R^2$ and $R^8$, NH, $R^9$, $NR^{10}R^{11}$, $R^{9'}$]

$L_n$ is an optional linking group having the formula:

$((W^1)_h-(CR^{13}R^{14})_g)_x-(Z)_k-((CR^{13a}R^{14a})_g-(W^2)_{h'})_{x'}$;

K is a chelator having a formula selected from the group:

[chelator structural formulas with $A^1$, $A^2$, $A^3$, $A^4$, $A^5$, $A^6$, $A^7$, $A^8$ and $E^1$, $E^2$, $E^3$, $E^4$, $E^5$, $E^6$, $E^7$, $E^8$], and R is independently OH or —CH$_2$SH;

$R^1$ is independently selected at each occurrence from the group: H, OH, $C_{1-3}$alkyl, $C_{2-3}$alkenyl, $C_{2-3}$alkynyl, and heterocycle-S—CH$_2$—;

$R^2$ is independently $C_{1-20}$alkyl;

X is independently C=O or SO$_2$, provided when X is C=O, $R^3$ is

[structure showing N-H attached to C with $R^4$ and $R^5$, and C=O]

and when X is SO$_2$, $R^3$ is independently selected from the group: aryl substituted with 0–2 $R^6$, and heterocycle substituted with 0–2 $R^6$;

$R^4$ is independently selected at each occurrence from the group: $C_{1-6}$alkyl, phenyl, and benzyl;

$R^5$ is independently at each occurrence from the group: NH($C_{1-6}$alkyl), NH-phenyl, and NH-heterocycle; wherein said alkyl, phenyl and heterocycle groups are optionally substituted with a bond to $L_n$ or a bond to K;

$R^6$ is independently aryloxy substituted with 0–3 $R^7$;

$R^7$ is independently halogen or methoxy; or alternatively, $R^1$ and $R^4$ may be taken together to form a bridging group of the formula —(CH$_2$)$_3$—O-phenyl-CH$_2$—, optionally substituted with a bond to $L_n$ or a bond to K; or alternatively, $R^1$ and $R^2$ may be taken together to form a bridging group of the formula —(CH$_2$)$_3$—NH—, optionally substituted with a bond to $L_n$ or a bond to K; or $R^1$ and $R^2$ taken together with the nitrogen and carbon atom through which they are attached form a saturated ring system containing 5–7 carbon atoms substituted with one or more substituents selected from the group consisting of: a bond to $L_n$, a bond to K, and —C(=O)—NR$^{29}$R$^{30}$;

R$^8$ is independently at each occurrence OH or phenyl, optionally substituted with a bond to $L_n$ or a bond to K, provided that when R$^8$ is phenyl, R$^{10}$ is —C(=O)—CR$^{12}$—NH—CH(CH$_3$)—COOH;

R$^9$ and R$^{9'}$ are independently H, C$_{1-6}$alkyl optionally substituted with a bond to $L_n$ or a bond to K, or are taken together with the carbon atom to which R$^9$ and R$^{9'}$ are attached to form a 5–7 atom saturated, partially unsaturated or aromatic ring system containing 0–3 heteroatoms selected from O, N, SO$_2$ and S, said ring system substituted with R$^6$ and optionally substituted with a bond to $L_n$ or a bond to K;

R$^{10}$ and R$^{11}$ are independently H, C$_{1-6}$alkyl optionally substituted with a bond to $L_n$ or a bond to K, or are taken together with the nitrogen atom to which they are attached to form a 5–7 atom saturated, partially unsaturated or aromatic ring system containing, in addition to the nitrogen atom to which R$^{10}$ and R$^{11}$ are attached, 0–3 heteroatoms selected from O, N, SO$_2$ and S, said ring system optionally substituted with 0–3 R$^{27}$, a bond to $L_n$ or a bond to K; or alternatively, R$^9$ and R$^{10}$ are taken together with the carbon atom to which they are attached to form a 5–7 atom saturated, partially unsaturated or aromatic ring system containing, in addition to the nitrogen atom to which R$^{10}$ is attached, 0–3 heteroatoms selected from O, N, SO$_2$ and S, said ring system optionally substituted with a bond to $L_n$ or a bond to K;

R$^{12}$ is independently C$_{1-20}$alkyl;

R$^{27}$ is =O, C$_{1-4}$alkyl, or phenyl substituted with R$^{28}$;

R$^{28}$ is a phenoxy group substituted with 0–2 OCH$_3$ groups;

R$^{29}$ and R$^{30}$ taken together with the nitrogen atom through which they are attached form a saturated ring system containing 5–7 carbon atoms substituted with R$^{31}$;

R$^{31}$ is a benzyloxy group substituted with C$_{1-4}$alkyl;

d is selected from 1, 2, 3, 4, 5, 6, 7, 8, 9, and 10;

W$^1$ and W$^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–3 R$^{16}$, C$_{3-10}$cycloalkyl substituted with 0–3 R$^{16}$, and a 5–10 membered heterocyclic ring system containing 1–4 heteroatoms independently selected from N, S, and O and substituted with 0–3 R$^{16}$;

R$^{13}$, R$^{13a}$, R$^{14}$, R$^{14a}$, and R$^{15}$ are independently selected at each occurrence from the group: H, =O, COOH, SO$_3$H, PO$_3$H, C$_{1-5}$alkyl substituted with 0–3 R$^{16}$, aryl substituted with 0–3 R$^{16}$, benzyl substituted with 0–3 R$^{16}$, and C$_{1-5}$alkoxy substituted with 0–3 R$^{16}$, NHC(=O)R$^{17}$, C(=O)NHR$^{17}$, NHC(=O)NHR$^{17}$, NHR$^{17}$, R$^{17}$, and a bond to K;

R$^{16}$ is independently selected at each occurrence from the group: a bond to K, COOR$^{17}$, C(=O)NHR$^{17}$, NHC(=O)R$^{17}$, OH, NHR$^{17}$, SO$_3$H, PO$_3$H, —OPO$_3$H$_2$, —OSO$_3$H, aryl substituted with 0–3 R$^{17}$, C$_{1-5}$alkyl substituted with 0–1 R$^{18}$, C$_{1-5}$alkoxy substituted with 0–1 R$^{18}$, and a 5–10 membered heterocyclic ring system containing 1–4 heteroatoms independently selected from N, S, and O and substituted with 0–3 R$^{17}$;

R$^{17}$ is independently selected at each occurrence from the group: H, alkyl substituted with 0–1 R$^{18}$, aryl substituted with 0–1 R$^{18}$, a 5–10 membered heterocyclic ring system containing 1–4 heteroatoms independently selected from N, S, and O and substituted with 0–1 R$^{18}$, C$_{3-10}$cycloalkyl substituted with 0–1 R$^{18}$, polyalkylene glycol substituted with 0–1 R$^{18}$, carbohydrate substituted with 0–1 R$^{18}$, cyclodextrin substituted with 0–1 R$^{18}$, amino acid substituted with 0–1 R$^{18}$, polycarboxyalkyl substituted with 0–1 R$^{18}$, polyazaalkyl substituted with 0–1 R$^{18}$, peptide substituted with 0–1 R$^{18}$, wherein the peptide is comprised of 2–10 amino acids, 3,6-O-disulfo-B-D-galactopyranosyl, bis(phosphonomethyl)glycine, and a bond to K;

R$^{18}$ is a bond to K;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

x" is selected from 0 and 1;

A$^1$, A$^2$, A$^3$, A$^4$, A$^5$, A$^6$, A$^7$, and A$^8$ are independently selected at each occurrence from the group: N, NR$^{26}$, NR$^{19}$, NR$^{19}$R$^{20}$, S, SH, —S(Pg), O, OH, PR$^{19}$, PR$^{19}$R$^{20}$, —O—P(O)(R$^{21}$)—O—, P(O)R$^{21}$R$^{22}$, a bond to Q and a bond to $L_n$;

Pg is a thiol protecting group;

E$^1$, E$^2$, E$^3$, E$^4$, E$^5$, E$^6$, E$^7$, and E$^8$ are independently a bond, CH, or a spacer group independently selected at each occurrence from the group: C$_{1-16}$alkyl substituted with 0–3 R$^{23}$, aryl substituted with 0–3 R$^{23}$, C$_{3-10}$cycloalkyl substituted with 0–3 R$^{23}$, heterocyclo-C$_{1-10}$alkyl substituted with 0–3 R$^{23}$, wherein the heterocyclo group is a 5–10 membered heterocyclic ring system containing 1–4 heteroatoms independently selected from N, S, and O, C$_{6-10}$aryl-C$_{1-10}$alkyl substituted with 0–3 R$^{23}$, C$_{1-10}$alkyl-C$_{6-10}$aryl-substituted with 0–3 R$^{23}$, and a 5–10 membered heterocyclic ring system containing 1–4 hetero atoms independently selected from N, S, and O and substituted with 0–3 R$^{23}$;

R$^{19}$ and R$^{20}$ are each independently selected from the group: a bond to $L_n$, a bond to Q, hydrogen, C$_{1-10}$alkyl substituted with 0–3 R$^{23}$, aryl substituted with 0–3 R$^{23}$, C$_{3-10}$cycloalkyl substituted with 0–3 R$^{23}$, heterocyclo-C$_{1-10}$alkyl substituted with 0–3 R$^{23}$, wherein the heterocyclo group is a 5–10 membered heterocyclic ring system containing 1–4 heteroatoms independently selected from N, S, and O, C$_{6-10}$ aryl-C$_{1-10}$ alkyl substituted with 0–3 R$^{23}$, C$_{1-10}$alkyl-C$_{6-10}$aryl-substituted with 0–3 R$^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{21}$ and $R^{22}$ are each independently selected from the group: a bond to $L_n$, a bond to Q, —OH, $C_{1-10}$alkyl substituted with 0–3 $R^{23}$, $C_{1-10}$alkyl substituted with 0–3 $R^{23}$, aryl substituted with 0–3 $R^{23}$, $C_{3-10}$cycloalkyl substituted with 0–3 $R^{23}$, heterocyclo-$C_{1-10}$alkyl substituted with 0–3 $R^{23}$, wherein the heterocyclo group is a 5–10 membered heterocyclic ring system containing 1–4 heteroatoms independently selected from N, S, and O, $C_{6-10}$aryl-$C_{1-10}$alkyl substituted with 0–3 $R^{23}$, $C_{1-10}$alkyl-$C_{6-10}$aryl-substituted with 0–3 $R^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a bond to $L_n$, a bond to Q, =O, F, Cl, Br, I, —$CF_3$, —CN, —$CO_2R^{24}$, —C(=O)$R^{24}$, —C(=O)N$(R^{24})_2$, —CHO, —$CH_2OR^{24}$, —OC(=O)$R^{24}$, —OC(=O)O$R^{24a}$, —$OR^{24}$, —OC(=O)N$(R^{24})_2$, —$NR^{25}$C(=O)$R^{24}$, —$NR^{25}$C(=O)O$R^{24a}$, —$NR^{25}$C(=O)N$(R^{24})_2$, —$NR^{25}SO_2N(R^{24})_2$, —$NR^{25}SO_2R^{24a}$, —$SO_3H$, —$SO_2R^{24a}$, —$SR^{24}$, —S(=O)$R^{24a}$, —$SO_2N(R^{24})_2$, —$N(R^{24})_2$, —NHC(=S)NHR$^{24}$, =$NOR^{24}$, $NO_2$, —C(=O)NHOR$^{24}$, —C(=O)NHNR$^{24}R^{24a}$, —$OCH_2CO_2H$, 2-(1-morpholino)ethoxy, $C_{1-5}$alkyl, $C_{2-4}$alkenyl, $C_{3-6}$cycloalkyl, $C_{3-6}$cycloalkylmethyl, $C_{2-6}$alkoxyalkyl, aryl substituted with 0–2 $R^{24}$, and a 5–10 membered heterocyclic ring system containing 1–4 heteroatoms independently selected from N, S, and O;

wherein at least one of $A^1, A^2, A^3, A^4, A^5, A^6, A^7, A^8$ or $R^{23}$ is a bond to $L_n$ or Q;

$R^{24}, R^{24a}$, and $R^{25}$ are independently selected at each occurrence from the group: a bond to $L_n$, a bond to Q, H, $C_{1-6}$alkyl, phenyl, benzyl, $C_{3-6}$alkoxy, halide, nitro, cyano, and trifluoromethyl; and $R^{26}$ is a co-ordinate bond to a metal or a hydrazine protecting group; or a pharmaceutically acceptable salt thereof.

2. A method according to claim 1, wherein:
R is OH;
$R^1$ is independently selected at each occurence from the group: H, OH, $C_{1-3}$alkyl, $C_{2-3}$alkenyl, $C_{2-3}$alkynyl, and heterocycle-S—$CH_2$—;
$R^2$ is independently $C_{1-6}$alkyl;
X is C=O;
$R^4$ is independently selected at each occurrence from the group: $C_{1-6}$alkyl, phenyl, and benzyl;
$R^8$ is OH;
$R^9$ and $R^{9'}$ are independently H, $C_{1-6}$alkyl optionally substituted with a bond to $L_n$ or a bond to K, or are taken together with the carbon atom to which $R^9$ and $R^{9'}$ are attached to form a 5–7 atom saturated, partially unsaturated or aromatic ring system containing 0–1 heteroatoms selected from O, N, $SO_2$ and S, said ring system optionally substituted with a bond to $L_n$ or a bond to K;
$R^{10}$ and $R^{11}$ are independently H, or $C_{1-6}$alkyl optionally substituted with a bond to $L_n$ or a bond to K, or are taken together with the nitrogen atom to which they are attached to form a 5–7 atom saturated, partially unsaturated or aromatic ring system containing, in addition to the nitrogen atom to which $R^{10}$ and $R^{11}$ are attached,
0–1 heteroatoms selected from O, N, $SO_2$ and S, said ring system optionally substituted with 0–3 $R^{27}$, a bond to $L_n$, or a bond to K; or alternatively,
$R^9$ and $R^{10}$ are taken together with the carbon atom to which they are attached to form a 5–7 atom saturated, partially unsaturated or aromatic ring system containing, in addition to the nitrogen atom to which $R^{10}$ is attached, 0–1 heteroatoms selected from O, N, $SO_2$, and S, said ring system optionally substituted with a bond to $L_n$ or a bond to K; and
$R^{12}$ is independently $C_{1-6}$alkyl.

3. A method according to claim 1, wherein:
R is —OH;
$R^2$ is $C_{1-6}$alkyl;
X is C=O;
$R^3$ is

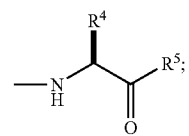

$R^1$ and $R^4$ are taken together to form a bridging group of formula —$(CH_2)_3$—O-phenyl-$CH_2$—; and
$R^5$ is NR($C_{1-6}$alkyl), substituted with a bond to $L_n$, or a bond to K.

4. A method according to claim 1, wherein:
R is —OH;
$R^9$ is $C_1$alkyl substituted with a bond to $L_n$; and
$R^{10}$ and $R^{11}$ taken together with the nitrogen atom to which they are attached form a 5 atom saturated ring system, said ring system substituted with 0–3 $R^{27}$.

5. A method according to claim 1, wherein:
R is —OH; and
$R^1$ and $R^2$ taken together with the nitrogen and carbon atom through which they are attached form a saturated ring system containing 5–7 carbon atoms substituted with one or more substituents selected from the group consisting of: a bond to $L_n$, a bond to K, and —C(=O)—$NR^{29}R^{30}$.

6. A method according to claim 1, wherein:
Z is selected from the group: aryl substituted with 0–1 $R^{16}$, $C_{3-10}$ cycloalkyl substituted with 0–1 $R^{16}$, and a 5–10 membered heterocyclic ring system containing 1–4 heteroatoms independently selected from N, S, and O and substituted with 0–1 $R^{16}$;
$R^{13}, R^{13a}, R^{14}, R^{14a}$, and $R^{15}$ are independently selected at each occurrence from the group: H, =O, COOH, $SO_3H$, $C_{1-5}$alkyl substituted with 0–1 $R^{16}$, aryl substituted with 0–1 $R^{16}$, benzyl substituted with 0–1 $R^{16}$, and $C_{1-5}$alkoxy substituted with 0–1 $R^{16}$, NHC(=O)$R^{17}$, C(=O)NHR$^{17}$, NHC(=O)NHR$^{17}$, NHR$^{17}$, $R^{17}$, and a bond to K;
k is 0 or 1;
s is selected from 0, 1, 2, 3, 4, and 5;
s' is selected from 0, 1, 2, 3, 4, and 5;
s" is selected from 0, 1, 2, 3, 4, and 5; and
t is selected from 0, 1, 2, 3, 4, and 5.

7. A method according to claim 1, wherein:
is C(=O)NR$^{15}$;
h is 1;
g is 3;

$R^{13}$ and $R^{14}$ are independently H;
x is 1;
k is 0;
g' is 0;
h' is 1;
$W^2$ is NH; and
x' is 1.

8. A method according to claim 1, wherein:
x is 0;
k is 1;
Z is aryl substituted with 0–3 $R^{16}$;
g' is 1;
$W^2$ is NH;
$R^{13a}$ and $R^{14a}$ are independently H;
h' is 1; and
x' is 1.

9. A method according to claim 1, wherein:
$W^1$ is C(=O)NR$^{15}$;
h is 1;
g is 2;
$R^{13}$ and $R^{14}$ are independently H;
x is 1;
k is 0;
g' is 1;
$R^{13a}$ and $R^{14a}$ are independently H; or $C_{1-5}$alkyl substituted with 0–3 $R^{16}$;
$R^{16}$ is SO$_3$H;
$W^2$ is NHC(=O) or NH;
h' is 1; and
x' is 2.

10. A method according to claim 1, wherein:
$W^1$ is C(=O)NH;
h is 1;
g is 3;
$R^{13}$ and $R^{14}$ are independently H;
k is 0;
g' is 0;
x is 1;
$W^2$ is —NH(C=O)— or —(OCH$_2$CH$_2$)$_{76-84}$—;
h' is 2; and
x' is 1.

11. A method according to claim 1, wherein:
x is 0;
k is 0;
g' is 3;
h' is 1;
$W^2$ is NH; and
x' is 1.

12. A method according to claim 1, wherein
x is 0;
Z is aryl substituted with 0–3 $R^{16}$;
k is 1;
g' is 1;
$R^{13a}$ and $R^{14a}$ are independently H;
$W^2$ is NHC(=O) or —(OCH$_2$CH$_2$)$_{76-84}$—; and
x' is 1.

13. A method according to claim 1, wherein:
$W^1$ is C=O;
g is 2;
$R^{13}$ and $R^{14}$ are independently H;
k is 0;
g' is 0;
h' is 1;
$W^2$ is NH; and
x' is 1.

14. A method according to claim 1, wherein:
h' is 1;
$W^2$ is NH; and
x' is 1.

15. A method according to claim 1, wherein:
x is 0;
Z is aryl substituted with 0–3 $R^{16}$;
k is 1;
g' is 1;
$R^{13a}$ and $R^{14a}$ are independently H;
$W^2$ is NHC(=O) or —(OCH$_2$CH$_2$)$_{76-84}$—; and
x' is 1.

16. A method according to claim 1, wherein:
$W^1$ is C=O;
g is 2;
$R^{13}$ and $R^{14}$ are independently H;
k is 0;
g' is 0;
h' is 1;
$W^2$ is NH; and
x' is 1.

17. A method according to claim 1, wherein
$A^1$, $A^2$, $A^3$, $A^4$, $A^5$, $A^6$, $A^7$, and $A^8$ are independently selected at each occurrence from the group: NR$^{19}$, NR$^{19}$R$^{20}$, S, SH, OH, a bond to Q and a bond to $L_n$;
$E^1$, $E^2$, $E^3$, $E^4$, $E^5$, $E^6$, $E^7$, and $E^8$ are independently a bond, CH, or a spacer group independently selected at each occurrence from the group: $C_{1-10}$alkyl substituted with 0–3 $R^{23}$, aryl substituted with 0–3 $R^{23}$, $C_{3-10}$cycloalkyl substituted with 0–3 $R^{23}$, and a 5–10 membered heterocyclic ring system containing 1–4 heteroatoms independently selected from N, S, and O and substituted with 0–3 $R^{23}$;
$R^{19}$ and $R^{20}$ are each independently selected from the group: a bond to Q, a bond to $L_n$, hydrogen, $C_{1-10}$alkyl substituted with 0–3 $R^{23}$, aryl substituted with 0–3 $R^{23}$, a 5–10 membered heterocyclic ring system containing 1–4 heteroatoms independently selected from N, S, and O and substituted with 0–3 $R^{23}$, and an electron;
$R^{23}$ is independently selected at each occurrence from the group: a bond to Q, a bond to $L_n$, =O, F, Cl, Br, I, —CF$_3$, —CN, —CO$_2$R$^{24}$, —C(=O)R$^{24}$, —C(=O)N(R$^{24}$)$_2$, —CH$_2$OR$^{24}$, —OC(=O)R$^{24}$, —OC(=O)OR$^{24a}$, —OR$^{24}$, —OC(=O)N(R$^{24}$)$_2$, —NR$^{25}$C(=O)R$^{24}$, —NR$^{25}$C(=O)OR$^{24a}$, —NR$^{25}$C(=O)N(R$^{24}$)$_2$, —NR$^{25}$SO$_2$N(R$^{24}$)$_2$, —NR$^{25}$SO$_2$R$^{24a}$, —SO$_3$H, —SO$_2$R$^{24a}$, —S(=O)R$^{24a}$, —SO$_2$N(R$^{24}$)$_2$, —N(R$^{24}$)$_2$, —NHC(=S)NHR$^{24}$, =NOR$^{24}$, —C(=O)NHNR$^{24}$R$^{24a}$, —OCH$_2$CO$_2$H, and 2-(1-morpholino)ethoxy; and
$R^{24}$, $R^{24a}$, and $R^{25}$ are independently selected at each occurrence from the group: a bond to $L_n$, H, and $C_{1-6}$alkyl.

18. A method according to claim 1, wherein K is:

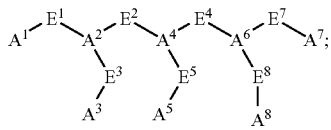

$A^1$ is a bond to $L_n$;
$A^2$, $A^4$, and $A^6$ are each N;
$A^3$, $A^5$, $A^7$ and $A^8$ are each OH;
$E^1$, $E^2$, and $E^4$ are $C_2$alkyl;
$E^3$, $E^5$, $E^7$, and $E^8$ are $C_2$alkyl substituted with 0–1 $R^{23}$; and
$R^{23}$ is =O.

19. A method according to claim 1, wherein K is:

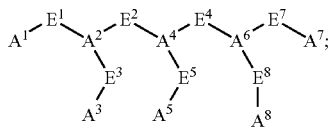

wherein:
$A^5$ is a bond to Ln;
$A^1$, $A^3$, $A^7$ and $A^8$ are each OH;
$A^2$, $A^4$ and $A^6$ are each N;
$E^1$, $E^3$, $E^5$, $E^7$, and $E^8$ are $C_2$ alkyl substituted with 0–1$R^{23}$;
$E^2$ and $E^4$ $^{l\ are\ C}{}_2$ alkyl; and
$R^{23}$ is =O.

20. A method according to claim 1, wherein K is:

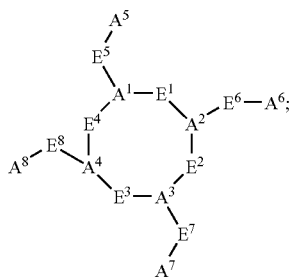

$A^1$, $A^2$, $A^3$ and $A^4$ are each N;
$A^5$, $A^6$ and $A^8$ are each OH;
$A^7$ is a bond to $L_n$;
$E^1$, $E^2$, $E^3$, $E^4$ are each independently $C_2$alkyl; and
$E^5$, $E^6$, $E^7$, $E^8$ are each independently $C_2$alkyl substituted with 0–1 $R^{23}$; and
$R^{23}$ is =O.

21. A method according to claim 1, wherein K is:

$A^1$ is $NR^{26}$;
$R^{26}$ is a co-ordinate bond to a metal or a hydrazine protecting group;
$E^1$ is a bond;
$A^2$ is $NHR^{19}$;
$R^{19}$ is a heterocycle substituted with $R^{23}$, the heterocycle being selected from pyridine and pyrimidine;
$R^{23}$ is selected from a bond to $L_n$, C(=O)NHR$^{24}$ and C(=O)R$^{24}$; and
$R^{24}$ is a bond to $L_n$.

22. A method according to claim 1, wherein wherein K is:

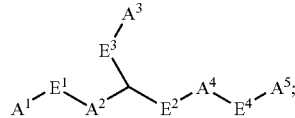

wherein:
$A^1$ and $A^5$ are each —S(Pg);
$E^1$ and $E^4$ are $C_2$alkyl substituted with 0–1 $R^{23}$;
$R^{23}$ is =O;
$A^2$ and $A^4$ are each —NH;
$E^2$ is $CH_2$;
$E^3$ is $C_{1-3}$ alkyl substituted with 0–1 $R^{23}$; and
$A^3$ is a bond to Ln.

23. A method according to claim 1, wherein K is:

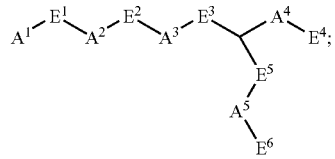

wherein:
$A^1$ is a bond to Ln;
$E^1$ is $C_1$alkyl substituted by $R^{23}$;
$A^2$ is NH;
$E^2$ is $C_2$alkyl substituted with 0–1 $R^{23}$;
$A^3$ is —O—P(O)($R^{21}$)—O—;
$E^3$ is $C_1$alkyl;
$A^4$ and $A^5$ are each —O—;
$E^4$ and $E^6$ are each independently $C_{1-16}$alkyl substituted with 0–1 $R^{23}$;
$E^5$ is $C_1$ alkyl;
$R^{21}$ is —OH; and
$R^{23}$ is =O.

24. A method according to claim 1, wherein the compound is:

2-{[5-(3-{2-[(6-Hydroxycarbamoyl-7-isobutyl-8-oxo-2-oxa-9-aza-bicyclo[10.2.2]hexadeca-1(15),12(16),13-triene-10-carbonyl)-amino]-acetylamino}-propylcarbamoyl)-pyridin-2-yl]-hydrazonomethyl}-benzenesulfonic acid;

2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzenesulfonic acid;

2-[7-({N-[3-(2-{[7-(N-hydroxycarbamoyl)(3S,6R,7S)-4-aza-6-(2-methylpropyl)-11-oxa-5-oxobicyclo[10.2.2] hexadeca-1(15),12(16),13-trien-3-yl] carbonylamino}propyl] carbamoyl}methyl)-1,4,7,10-tetraaza-4,10-bis (carboxymethyl)cyclododecyl]acetic acid;

2-{7-[(N-{[4-({[7-(N-hydroxycarbamoyl)(3S,6R,7S)-4-aza-6-(2-methylpropyl)-11-oxa-5-oxobicyclo[10.2.2]

hexadeca-1(15),12(16),13-trien-3-yl]-carbonylamino}methyl)phenyl]methyl}carbamoyl)methyl]-1,4,7,10-tetraaza-4,10-bis(carboxymethyl)cyclododecyl}acetic acid;

2-(7-{[N-(1-{N-[3-(2-{[7-(N-hydroxycarbamoyl)(3S,6R,7S)-4-aza-6-(2-methylpropyl)-11-oxa-5-oxobicyclo[10.2.2]hexadeca-1(15),12 (16),13-trien-3-yl]carbonylamino}acetylamino)propyl]carbamoyl}-2-sulfoethyl)carbamoyl]methyl}-1,4,7,10-tetraaza-4,10-bis(carboxymethyl)cyclododecyl)acetic acid;

2-[7-({N-[1-(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)-2-sulfoethyl]carbamoyl}methyl)-1,4,7,10-tetraaza-4,10-bis(carboxymethyl)cyclododecyl]acetic acid;

2-({2-[({N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}methyl)(carboxymethyl)amino}ethyl){2-[bis(carboxymethyl)amino]ethyl}amino]acetic acid;

2-[(2-{[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)methyl](carboxymethyl)amino}ethyl){2-[bis(carboxymethyl)amino]ethyl}amino]acetic acid;

N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-4,5-bis[2-(ethoxyethylthio)acetylamino]pentanamide;

N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}methyl)-phenyl]methyl}-4,5-bis[2-(ethoxyethylthio)acetylamino]-pentanamide;

1-(1,2-Dipalmitoyl-sn-glycero-3-phosphoethanolamino)-α,ω-dicarbonylPEG$_{3400}$-2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide;

1-(1,2-Dipalmitoyl-sn-glycero-3-phosphoethanolamino)-α,ω-dicarbonylPEG$_{3400}$-[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide conjugate;

2-[2-({5-[N-(5-(N-hydroxycarbamoyl)(5R)-5-{3-[4-(3,4-dimethoxyphenoxy)phenyl]-3-methyl-2-oxopyrrolidinyl}pentyl)carbamoyl](2-pyridyl)}amino)(1Z)-2-azavinyl]benzenesulfonic acid;

2-(2-{[5-(N-{3-[3-(N-hydroxycarbamoyl)(4S)-4-({4-[(4-methylphenyl)methoxy]piperidyl}carbonyl)piperidyl]-3-oxopropyl}carbamoyl)(2-pyridyl)]amino}(1Z)-2-azavinyl)benzenesulfonic acid;

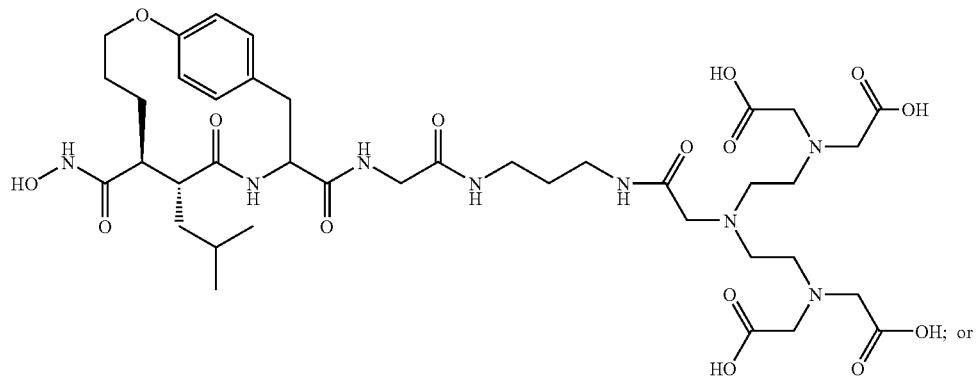

a pharmaceutically acceptable salt thereof.

25. A method according to claim 1, wherein the compound is:

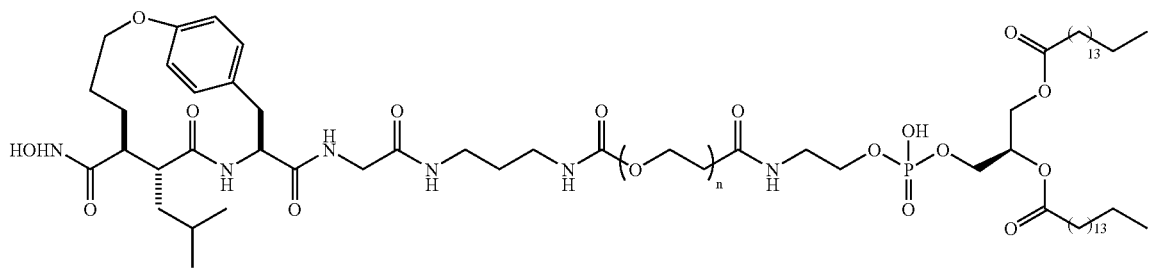

-continued

[chemical structure]

a pharmaceutically acceptable salt thereof.

26. A method according to claim 1, wherein the diagnostic metal is selected from the group consisting of: a paramagnetic metal, a ferromagnetic metal, a gamma-emitting radioisotope, positron-emitting radioisotope and an x-ray absorber.

27. A method according to claim 26, wherein the diagnostic metal is a gamma-emitting radioisotope selected from the group consisting of $^{99m}$Tc, $^{95}$Tc, $^{111}$In, $^{62}$Cu, $^{64}$Cu, $^{67}$Ga, and $^{68}$Ga.

28. A method according to claim 27, further comprising a first ancillary ligand and a second ancillary ligand capable of stabilizing the gamma-emitting radioisotope.

29. A method according to claim 27, wherein the gamma-emitting radioisotope is $^{99m}$Tc.

30. A method according to claim 27, wherein the gamma-emitting radioisotope is $^{111}$In.

31. A method according to claim 26, wherein the paramagnetic metal ion is selected from the group consisting of Gd(III), Dy(III), Fe(III), and Mn(II).

32. A method according to claim 26, wherein the x-ray absorber is a metal is selected from the group consisting of: Re, Sm, Ho, Lu, Pm, Y, Bi, Pd, Gd, La, Au, Au, Yb, Dy, Cu, Rh, Ag, and Ir.

33. A method of detecting, imaging or monitoring congestive heart failure in a patient, comprising the steps of:
administering a diagnostic agent to the patient; and
acquiring an image of a site of concentration of the diagnostic agent in the patient by a diagnostic imaging technique;
wherein the diagnostic agent comprises an echogenic gas and a compound of the formula:

$$(Q)_d—(L_n)_{x'}—K$$

or a pharmaceutically acceptable salt thereof;
wherein
Q is a matrix metalloproteinase inhibitor of formula (Ia) or (Ib):

[structure Ia]

[structure Ib]

$L_n$ is an optional linking group having the formula:

$$((W^1)_h—(CR^{13}R^{14})_g)_{x}—(Z)_{k}—((CR^{13a}R^{14a})_{g'}—(W^2)_{h'})_{x'};$$

K is a surfactant capable of forming an echogenic gas filled lipid sphere or microbubble, wherein the surfactant is a lipid or a compound having a formula selected from the group:

[structures]

R is independently OH or —CH$_2$SH;
R$^1$ is independently selected at each occurrence from the group: H, OH, C$_{1-3}$alkyl, C$_{2-3}$alkenyl, C$_{2-3}$alkynyl, and heterocycle-S—CH$_2$—;
R$^2$ is independently C$_{1-20}$alkyl;
X is independently C═O or SO$_2$, provided when X is C═O, R$^3$ is

[structure]

and when X is SO$_2$, R$^3$ is independently selected from the group: aryl substituted with 0–2 R$^6$, and heterocycle substituted with 0–2 R$^6$;
R$^4$ is independently selected at each occurrence from the group: C$_{1-6}$alkyl, phenyl, and benzyl;
R$^5$ is independently at each occurrence from the group: NH(C$_{1-6}$alkyl), NH-phenyl, and NH-heterocycle; wherein said alkyl, phenyl and heterocycle groups are optionally substituted with a bond to L$_n$ or a bond to K;
R$^6$ is independently aryloxy substituted with 0–3 R$^7$;
R$^7$ is independently halogen or methoxy; or alternatively, R¹ and R⁴ may be taken together to form a bridging group of the formula —(CH₂)₃—O-phenyl-CH₂—, optionally substituted with a bond to $L_n$ or a bond to K; or alternatively, R¹ and R² may be taken together to form a bridging group of the formula —(CH₂)₃—NH—, optionally substituted with a bond to $L_n$ or a bond to K; or R¹ and R² taken together with the nitrogen and carbon atom through which they are attached form a saturated ring system containing 5–7 carbon atoms substituted with one or more substituents selected from the group consisting of: a bond to $L_n$, a bond to K, and —C(=O)—NR²⁹R³⁰;

R⁸ is independently at each occurrence OH or phenyl, optionally substituted with a bond to $L_n$ or a bond to K, provided that when R⁸ is phenyl, R¹⁰ is —C(=O)—CR¹²=NH—CH(CH₃)—COOH;

R⁹ and R⁹' are independently H, C₁₋₆alkyl optionally substituted with a bond to $L_n$ or a bond to K, or are taken together with the carbon atom to which R⁹ and R⁹' are attached to form a 5–7 atom saturated, partially unsaturated or aromatic ring system containing 0–3 heteroatoms selected from O, N, SO₂ and S, said ring system substituted with R⁶ and optionally substituted with a bond to $L_n$ or a bond to K;

R¹⁰ and R¹¹ are independently H, C₁₋₆alkyl optionally substituted with a bond to $L_n$ or a bond to K, or are taken together with the nitrogen atom to which they are attached to form a 5–7 atom saturated, partially unsaturated or aromatic ring system containing, in addition to the nitrogen atom to which R¹⁰ and R¹¹ are attached, 0–3 heteroatoms selected from O, N, SO₂ and S, said ring system optionally substituted with 0–3 R²⁷, a bond to $L_n$ or a bond to K; or alternatively, R⁹ and R¹⁰ are taken together with the carbon atom to which they are attached to form a 5–7 atom saturated, partially unsaturated or aromatic ring system containing, in addition to the nitrogen atom to which R¹⁰ is attached, 0–3 heteroatoms selected from O, N, SO₂ and S, said ring system optionally substituted with a bond to $L_n$ or a bond to K;

R¹² is independently C₁₋₂₀alkyl;

R²⁷ is =O, C₁₋₄alkyl, or phenyl substituted with R²⁸;

R²⁸ is a phenoxy group substituted with 0–2 OCH₃ groups;

R²⁹ and R³⁰ taken together with the nitrogen atom through which they are attached form a saturated ring system containing 5–7 carbon atoms substituted with R³¹;

R³¹ is a benzyloxy group substituted with C₁₋₄alkyl;

d is selected from 1, 2, 3, 4, 5, 6, 7, 8, 9, and 10;

W¹ and W² are independently selected at each occurrence from the group: O, S, NH, NHC(=O), C(=O)NH, NR¹⁵C(=O), C(=O)NR¹⁵, C(=O), C(=O)O, OC(=O), NHC(=S)NH, NHC(=O)NH, SO₂, SO₂NH, —(OCH₂CH₂)₇₆₋₈₄, (OCH₂CH₂)$_s$, (CH₂CH₂O)$_{s'}$, (OCH₂CH₂CH₂)$_{s''}$, (CH₂CH₂CH₂O)$_t$, and (aa)$_{t'}$;

aa is independently at each occurrence an amino acid;

Z is selected from the group: aryl substituted with 0–3 R¹⁶, C₃₋₁₀cycloalkyl substituted with 0–3 R¹⁶, and a 5–10 membered heterocyclic ring system containing 1–4 heteroatoms independently selected from N, S, and O and substituted with 0–3 R¹⁶;

R¹³, R¹³ᵃ, R¹⁴, R¹⁴ᵃ, and R¹⁵ are independently selected at each occurrence from the group: H, =O, COOH, SO₃H, PO₃H, C₁₋₅alkyl substituted with 0–3 R¹⁶, aryl substituted with 0–3 R¹⁶, benzyl substituted with 0–3 R¹⁶, and C₁₋₅alkoxy substituted with 0–3 R¹⁶, NHC(=O)R¹⁷, C(=O)NHR¹⁷, NHC(=O)NHR¹⁷, NHR¹⁷, R¹⁷, and a bond to K;

R¹⁶ is independently selected at each occurrence from the group: a bond to K, COOR¹⁷, C(=O)NHR¹⁷, NHC(=O)R¹⁷, OH, NHR¹⁷, SO₃H, PO₃H, —OPO₃H₂, —OSO₃H, aryl substituted with 0–3 R¹⁷, C₁₋₅alkyl substituted with 0–1 R¹⁸, C₁₋₅alkoxy substituted with 0–1 R¹⁸, and a 5–10 membered heterocyclic ring system containing 1–4 heteroatoms independently selected from N, S, and O and substituted with 0–3 R¹⁷;

R¹⁷ is independently selected at each occurrence from the group: H, alkyl substituted with 0–1 R¹⁸, aryl substituted with 0–1 R¹⁸, a 5–10 membered heterocyclic ring system containing 1–4 heteroatoms independently selected from N, S, and O and substituted with 0–1 R¹⁸, C₃₋₁₀cycloalkyl substituted with 0–1 R¹⁸, polyalkylene glycol substituted with 0–1 R¹⁸, carbohydrate substituted with 0–1 R¹⁸, cyclodextrin substituted with 0–1 R¹⁸, amino acid substituted with 0–1 R¹⁸, polycarboxyalkyl substituted with 0–1 R¹⁸, polyazaalkyl substituted with 0–1 R¹⁸, peptide substituted with 0–1 R¹⁸, wherein the peptide is comprised of 2–10 amino acids, 3,6-O-disulfo-B-D-galactopyranosyl, bis(phosphonomethyl)glycine, and a bond to K;

R¹⁸ is a bond to K;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s'' is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

x'' is selected from 0 and 1;

A¹, A², A³, A⁴, A⁵, and A⁶ are independently selected at each occurrence from the group: N, NR²⁶, NR¹⁹, NR¹⁹R²⁰, S, SH, —S(Pg), O, OH, PR¹⁹, PR¹⁹R²⁰, —O—P(O)(R²¹)—O—, P(O)R²¹R²², a bond to Q and a bond to $L_n$;

A⁹ is selected from the group: OH and OR³²;

A¹⁰ is OR³²;

R³² is C(=O)C₁₋₂₀alkyl;

Pg is a thiol protecting group;

E¹, E², E³, E⁴, E⁵ are independently a bond, CH, or a spacer group independently selected at each occurrence from the group: C₁₋₁₆alkyl substituted with 0–3 R²³, aryl substituted with 0–3 R²³, C₃₋₁₀cycloalkyl substituted with 0–3 R²³, heterocyclo-C₁₋₁₀alkyl substituted with 0–3 R²³, wherein the heterocyclo group is a 5–10 membered heterocyclic ring system containing 1–4 heteroatoms independently selected from N, S, and O, C₆₋₁₀aryl-C₁₋₁₀alkyl substituted with 0–3 R²³, C₁₋₁₀alkyl-C₆₋₁₀aryl-substituted with 0–3 R²³, and a 5–10 membered heterocyclic ring system containing 1–4 hetero atoms independently selected from N, S, and O and substituted with 0–3 $R^{23}$;

$E^9$ is $C_{1-10}$alkylene substituted with 1–3 $R^{33}$;

$R^{33}$ is independently selected at each occurrence from the group: $R^{35}$, —$PO_3H$—$R^{35}$, =O, —$CO_2R^{34}$, —C(=O)$R^{34}$, —C(=O)N($R^{34}$)$_2$, —$CH_2OR^{34}$, —$OR^{34}$, —N($R^{34}$)$_2$, $C_{1-5}$alkyl, and $C_{24}$alkenyl;

$R^{34}$ is independently selected at each occurrence from the group: $R^{35}$, H, $C_{1-6}$alkyl, phenyl, benzyl, and trifluoromethyl;

$R^{35}$ is a bond to $L_n$;

$R^{19}$ and $R^{20}$ are each independently selected from the group: a bond to $L_n$, a bond to Q, hydrogen, $C_{1-10}$alkyl substituted with 0–3 $R^{23}$, aryl substituted with 0–3 $R^{23}$, $C_{3-10}$cycloalkyl substituted with 0–3 $R^{23}$, heterocyclo-$C_{1-10}$alkyl substituted with 0–3 $R^{23}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{23}$, $C_{1-10}$alkyl-$C_{6-10}$aryl-substituted with 0–3 $R^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{21}$ and $R^{22}$ are each independently selected from the group: a bond to $L_n$, a bond to Q, —OH, $C_{1-10}$alkyl substituted with 0–3 $R^{23}$, $C_{1-10}$alkyl substituted with 0–3 $R^{23}$, aryl substituted with 0–3 $R^{23}$, $C_{3-10}$cycloalkyl substituted with 0–3 $R^{23}$, heterocyclo-$C_{1-10}$alkyl substituted with 0–3 $R^{23}$, wherein the heterocyclo group is a 5–10 membered heterocyclic ring system containing 1–4 heteroatoms independently selected from N, S, and O, $C_{6-10}$aryl-$C_{1-10}$alkyl substituted with 0–3 $R^{23}$, $C_{1-10}$alkyl-$C_{6-10}$aryl-substituted with 0–3 $R^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a bond to $L_n$, a bond to Q, =O, F, Cl, Br, I, —$CF_3$, —CN, —$CO_2R^{24}$, —C(=O)$R^{24}$, —C(=O)N($R^{24}$)$_2$, —CHO, —$CH_2OR^{24}$, —OC(=O)$R^{24}$, —OC(=O)$OR^{24a}$, —$OR^{24}$, —OC(=O)N($R^{24}$)$_2$, —$NR^{25}$C(=O)$R^{24}$, —$NR^{25}$C(=O)$OR^{24a}$, —$NR^{25}$C(=O)N($R^{24}$)$_2$, —$NR^{25}SO_2N(R^{24})_2$, —$NR^{25}SO_2R^{24a}$, —$SO_3H$, —$SO_2R^{24a}$, —$SR^{24}$, —S(=O)$R^{24a}$, —$SO_2N(R^{24})_2$, —N($R^{24}$)$_2$, —NHC(=S)NHR$^{24}$, =NOR$^{24}$, $NO_2$, —C(=O)NHOR$^{24}$, —C(=O)NHNR$^{24}R^{24a}$, —$OCH_2CO_2H$, 2-(1-morpholino)ethoxy, $C_{1-5}$alkyl, $C_{2-4}$alkenyl, $C_{3-6}$cycloalkyl, $C_{3-6}$cycloalkylmethyl, $C_{2-6}$alkoxyalkyl, aryl substituted with 0–2 $R^{24}$, and a 5–10 membered heterocyclic ring system containing 1–4 heteroatoms independently selected from N, S, and O;

wherein at least one of $A^1$, $A^2$, $A^3$, $A^4$, $A^5$, $A^6$, $A^7$, $A^8$ or $R^{23}$ is a bond to $L_n$ or Q;

$R^{24}$, $R^{24a}$, and $R^{25}$ are independently selected at each occurrence from the group: a bond to $L_n$, a bond to Q, H, $C_{1-6}$alkyl, phenyl, benzyl, $C_{1-6}$alkoxy, halide, nitro, cyano, and trifluoromethyl; and $R^{26}$ is a co-ordinate bond to a metal or a hydrazine protecting group.

34. A method according to claim 33, wherein:

R is OH;

$R^1$ is independently selected at each occurrence from the group: H, OH, $C_{1-3}$alkyl, $C_{2-3}$alkenyl, $C_{2-3}$alkynyl, and heterocycle-S—$CH_2$—;

$R^2$ is independently $C_{1-6}$alkyl;

X is C=O;

$R^4$ is independently selected at each occurrence from the group: $C_{1-6}$alkyl, phenyl, and benzyl;

$R^8$ is OH;

$R^9$ and $R^{9'}$ are independently H, $C_{1-6}$alkyl optionally substituted with a bond to $L_n$, or a bond to K, or are taken together with the carbon atom to which $R^9$ and $R^{9'}$ are attached to form a 5–7 atom saturated, partially unsaturated or aromatic ring system containing 0–1 heteroatoms selected from O, N, $SO_2$ and S, said ring system optionally substituted with a bond to $L_n$ or a bond to K;

$R^{10}$ and $R^{11}$ are independently H, or $C_{1-6}$alkyl optionally substituted with a bond to $L_n$ or a bond to K, or are taken together with the nitrogen atom to which they are attached to form a 5–7 atom saturated, partially unsaturated or aromatic ring system containing, in addition to the nitrogen atom to which $R^{10}$ and $R^{11}$ are attached, 0–1 heteroatoms selected from O, N, $SO_2$ and S, said ring system optionally substituted with 0–3 $R^{27}$, a bond to $L_n$ or a bond to K; or alternatively, $R^9$ and $R^{10}$ are taken together with the carbon atom to which they are attached to form a 5–7 atom saturated, partially unsaturated or aromatic ring system containing, in addition to the nitrogen atom to which $R^{10}$ is attached, 0–1 heteroatoms selected from O, N, $SO_2$, and S, said ring system optionally substituted with a bond to $L_n$, or a bond to K;

$R^{12}$ is independently $C_{1-6}$alkyl.

35. A method according to claim 33, wherein:

R is —OH;

$R^2$ is $C_{1-6}$alkyl;

X is C=O;

$R^3$ is $R^1$ and $R^4$ are taken together to form a bridging group of formula —($CH_2$)$_3$—O-phenyl-$CH_2$—; and $R^5$ is NH($C_{1-6}$alkyl), substituted with a bond to $L_n$, or a bond to K.

36. A method according to claim 33, wherein:

R is —OH;

$R^9$ is $C_1$alkyl substituted with a bond to $L_n$; and $R^{10}$ and $R^{11}$ taken together with the nitrogen atom to which they are attached form a 5 atom saturated ring system, said ring system substituted with 0–3 $R^{27}$.

37. A method according to claim 33, wherein:

R is —OH;

$R^1$ and $R^2$ taken together with the nitrogen and carbon atom through which they are attached form a saturated ring system containing 5–7 carbon atoms substituted with one or more substituents selected from the group consisting of: a bond to $L_n$, a bond to K, and —C(=O)—NR$^{29}R^{30}$;

$R^{29}$ and $R^{30}$ taken together with the nitrogen atom through which they are attached form a saturated ring system containing 5–7 carbon atoms substituted with $R^{31}$; and $R^{31}$ is a benzyloxy group substituted with $C_{1-4}$alkyl.

38. A method according to claim 33, wherein:

$W^1$ and $W^2$ are independently selected at each occurrence from the group: O, NH, NHC(=O), C(=O)NH, $NR^{15}C(=O)$, $C(=O)NR^{15}$, C(=O), C(=O)O, OC(=O), NHC(=S)NH, NHC(=O)NH, $SO_2$, —$(CH_2CH_2O)_{76-84}$—, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–1 $R^{16}$, $C_{3-10}$cycloalkyl substituted with 0–1 $R^{16}$, and a 5–10 membered heterocyclic ring system containing 1–4 heteroatoms independently selected from N, S, and O and substituted with 0–1 $R^{16}$;

$R^{13}$, $R^{13a}$, $R^{14}$, $R^{14a}$, and $R^{15}$ are independently selected at each occurrence from the group: H, =O, COOH, $SO_3H$, $C_{1-5}$alkyl substituted with 0–1 $R^{16}$, aryl substituted with 0–1 $R^{16}$, benzyl substituted with 0–1 $R^{16}$, and $C_{1-5}$alkoxy substituted with 0–1 $R^{16}$, NHC(=O)$R^{17}$, C(=O)NH$R^{17}$, NHC(=O)NH$R^{17}$, NH$R^{17}$, $R^{17}$, and a bond to K;

k is 0 or 1;

s is selected from 0, 1, 2, 3, 4, and 5;

s' is selected from 0, 1, 2, 3, 4, and 5;

s'' is selected from 0, 1, 2, 3, 4, and 5; and t is selected from 0, 1, 2, 3, 4, and 5.

39. A method according to claim 33, wherein:

$W^1$ is C(=O)$NR^{15}$;

h is 1;

g is 3;

$R^{13}$ and $R^{14}$ are independently H;

x is 1;

k is 0;

g' is 0;

h' is 1;

$W^2$ is NH; and x' is 1.

40. A method according to claim 33, wherein:

x is 0;

k is 1;

Z is aryl substituted with 0–3 $R^{16}$;

g' is 1;

$W^2$ is NH;

$R^{13a}$ and $R^{14a}$ are independently H;

h' is 1; and x' is 1.

41. A method according to claim 33, wherein:

$W^1$ is C(=O)$NR^{15}$;

h is 1;

g is 2;

$R^{13}$ and $R^{14}$ are independently H;

x is 1;

k is 0;

g' is 1;

$R^{13a}$ and $R^{14a}$ are independently H; or $C_{1-5}$alkyl substituted with 0–3 $R^{16}$;

$R^{16}$ is $SO_3H$;

$W^2$ is NHC(=O) or NH;

h' is 1; and x' is 2.

42. A method according to claim 33, wherein:

$W^1$ is C(=O)NH;

h is 1;

g is 3;

$R^{13}$ and $R^{14}$ are independently H;

k is 0;

g' is O;

x is 1;

$W^2$ is —NH(C=O)— or —$(OCH_2CH_2)_{76-84}$—;

h' is 2; and x' is 1.

43. A method according to claim 33, wherein:

x is 0;

k is 0;

g' is 3;

h' is 1;

$W^2$ is NH; and x' is 1.

44. A method according to claim 33, wherein x is 0;

Z is aryl substituted with 0–3 $R^{16}$;

k is 1;

g' is 1;

$R^{13a}R^{14a}$ are independently H;

$W^2$ is NHC(=O) or —$(OCH_2CH_2)_{76-84}$—; and x' is 1.

45. A method according to claim 33, wherein:

$W^1$ is C=O;

g is 2;

$R^{13}$ and $R^{14}$ are independently H;

k is 0;

g' is 0;

h' is 1;

$W^2$ is NH; and x' is 1.

46. A method according to claim 33, wherein:

h' is 1;

$W^2$ is NH; and x' is 1.

47. A method according to claim 33, wherein:

x is 0;

Z is aryl substituted with 0–3 $R^{16}$;

k is 1;

g' is 1;

$R^{13a}R^{14a}$ are independently H;

$W^2$ is NHC(=O) or —$(OCH_2CH_2)_{76-84}$—; and x' is 1.

48. A method according to claim 33, wherein:

$W^1$ is C=O;

g is 2;

$R^{13}$ and $R^{14}$ are independently H;

k is 0;

g' is 0;

h' is 1;

$W^2$ is NH; and x' is 1.

49. A method according to claim 33, wherein K is a lipid or a compound of the formula:

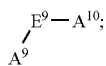

wherein:
A$^9$ is OR$^{32}$;
A$^{10}$ is OR$^{32}$;
R$^{32}$ is C(=O)C$_{1-15}$alkyl;
E$^9$ is C$_{1-4}$alkylene substituted with 1–3 R$^{33}$;
R$^{33}$ is independently selected at each occurrence from the group: R$^{35}$, —PO$_3$H—R$^{35}$, =O, —CO$_2$R$^{34}$, —C(=O)R$^{34}$, —CH$_2$OR$^{34}$, —OR$^{34}$, and C$_{1-5}$alkyl; and
R$^{34}$ is independently selected at each occurrence from the group: R$^{35}$, H, C$_{1-6}$alkyl, phenyl, and benzyl.

50. A method according to claim 33, wherein K is a compound of the formula:

A$^2$ is NH;
E$^2$ is C$_2$alkyl substituted with 0–1R$^{23}$;
A$^3$ is —O—P(O)(R$^{21}$)—O—;
E$^3$ is C$_1$alkyl;
A$^4$ and A$^5$ are each —O—;
E$^4$ and E$^6$ are each independently C$_{1-16}$alkyl substituted with 0–1R$^{23}$;
E$^5$ is C$_1$ alkyl;
A$^5$ is —O—;
R$^{21}$ is —OH; and
R$^{23}$ is =O.

51. A method according to claim 33, wherein the compound is:

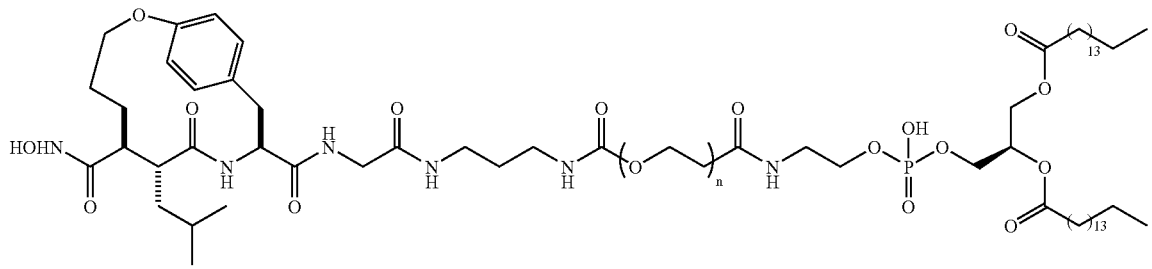

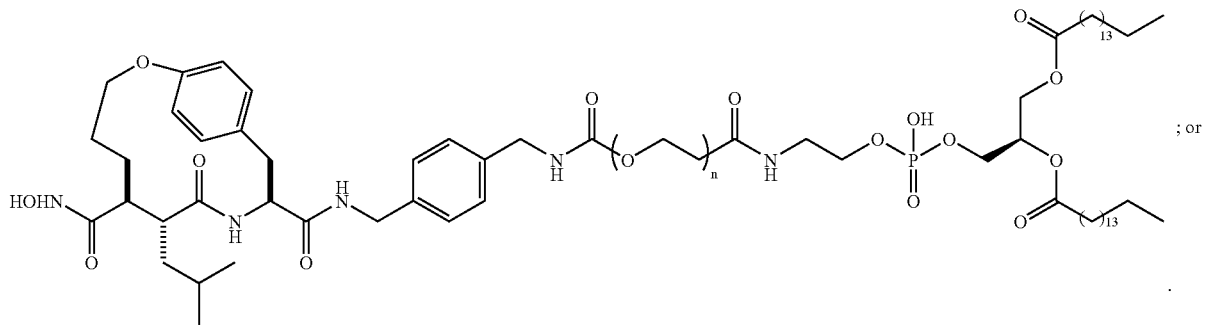

pharmaceutically acceptable salt thereof.

52. A method according to claim 33, wherein the echogenic gas is a perfluorocarbon gas or sulfur hexafluoride.

53. A method according to claim 52, wherein said perfluorocarbon gas is selected from the group consisting of perfluoromethane, perfluoroethane, perfluoropropane, perfluorobutane, perfluorocyclobutane, perfluoropentane, and perfluorohexane.

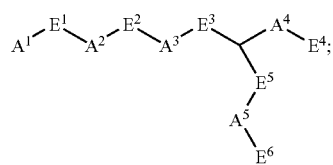

wherein:
A$^1$ is a bond to L$_n$;
E$^1$ is C$_1$ alkyl substituted by R$^{23}$;

* * * * *